(12) United States Patent
Srivastava et al.

(10) Patent No.: US 8,551,997 B2
(45) Date of Patent: *Oct. 8, 2013

(54) STRUCTURAL-BASED INHIBITORS OF THE GLUTATHIONE BINDING SITE IN ALDOSE REDUCTASE, METHODS OF SCREENING THEREFOR AND METHODS OF USE

(75) Inventors: Satish K. Srivastava, Galveston, TX (US); Kota V. Ramana, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/308,915

(22) PCT Filed: Jun. 29, 2007

(86) PCT No.: PCT/US2007/015322

§ 371 (c)(1),
(2), (4) Date: Aug. 11, 2009

(87) PCT Pub. No.: WO2008/002678

PCT Pub. Date: Jan. 3, 2008

(65) Prior Publication Data

US 2010/0016404 A1    Jan. 21, 2010

Related U.S. Application Data

(63) Continuation of application No. 11/478,069, filed on Jun. 29, 2006, now abandoned, which is a continuation-in-part of application No. 11/282,801, filed on Nov. 18, 2005, now Pat. No. 7,702,430.

(60) Provisional application No. 60/629,448, filed on Nov. 19, 2004.

(51) Int. Cl.
| *A01N 43/00* | (2006.01) |
| *A61K 31/397* | (2006.01) |
| *A61K 31/50* | (2006.01) |
| *A61K 31/501* | (2006.01) |

(52) U.S. Cl.
USPC .................. 514/252.01; 514/210.01

(58) Field of Classification Search
USPC ..................................... 514/252.01
See application file for complete search history.

(56) References Cited

U.S. PATENT DOCUMENTS

| 2004/0047919 A1 | 3/2004 | Srivastava et al. ............ 424/718 |
| 2004/0235071 A1 | 11/2004 | Lightcap et al. ............. 435/7.23 |
| 2005/0004225 A1* | 1/2005 | Balendiran .................... 514/571 |

FOREIGN PATENT DOCUMENTS

WO    WO 9207830 A1 *  5/1992

OTHER PUBLICATIONS

Kawamura et al. (1999) Anticancer Res. 19:4105-4112.*
Lee, et al. *Inhibition of aldose Reductase Enhances Hela Cell Sensitivity to Chemotherapeutic drugs and Involves Activation of Extracellular Signal-Regulated Kinases: Anti-Cancer Drugs*, 2002, vol. 13, p. 859-868.
Kang, et al. *Phorbol Ester Up-Regulates Aldose Reductase Expression in A549 Cells: a Potential Role for Aldose Reductase in Cell Cycle Modulation: CMLS Cellular and Molecular Life Scicenes*, May 2005, vol. 62, No. 10, p. 1146-1155.
Potential Kang, et al. *Phorbol Ester Up-Regulates Aldose Reductase Expression in A549 Cells: a Role for Aldose Reductase in Cell Cycle Modulation: CMLS Cellular and Molecular Life Scicenes*, May 2005, vol. 62, No. 10, p. 1146-1155.
Ramana, et al. *Mitogenic Responses of Vascular Smooth Muscle Cells to Lipid Peroxidation-derived Aldehyde 4-Hydroxy-Trans-2Nonenal (HNE): Journal of Biological Chemistry*, Jun. 30, 2006, vol. 281, No. 26, p. 17652-17660.

* cited by examiner

Primary Examiner — Sreeni Padmanabhan
Assistant Examiner — Layla Soroush

(57) ABSTRACT

Provided herein are methods of treating a pathophysiological state or symptoms thereof resulting from aldose reductase-mediated signaling in a cytotoxic pathway in a subject using an inhibitor of aldose reductase. Particularly, specific inhibitors may be a small-interfering RNA (siRNA) or may be inhibitors of glutathione-aldehyde binding to aldose reductase which are designed via at least computer modeling of the ternary AR:NADPH:DCEG structure. Also, methods of treating a cancer or suppressing metastasis thereof using the siRNAs and aldose reductase inhibitors are provided.

1 Claim, 30 Drawing Sheets

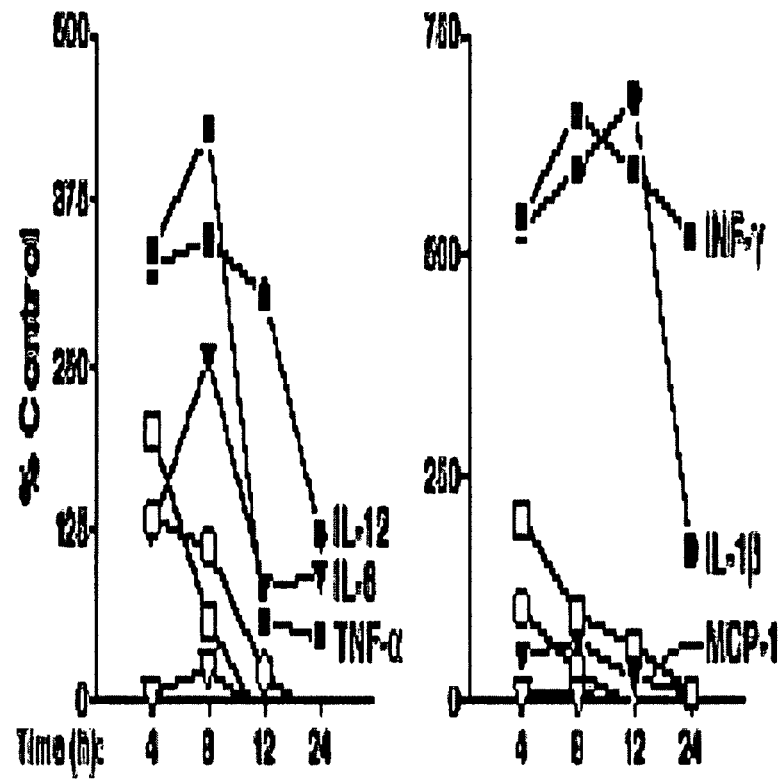
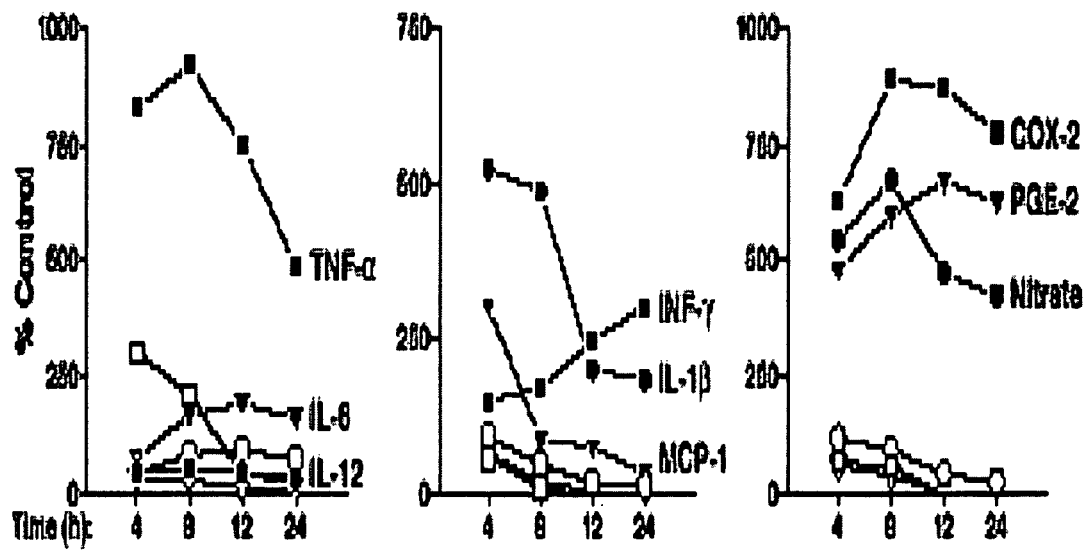
Fig. 6A    Fig. 6B
Fig. 6C    Fig. 6D    Fig. 6E

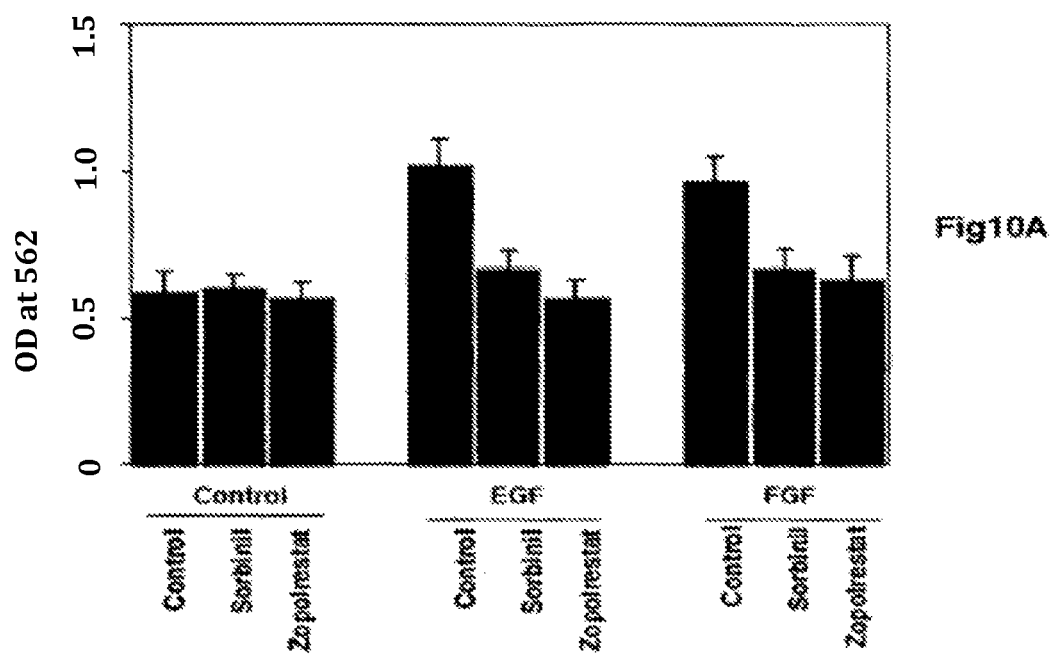
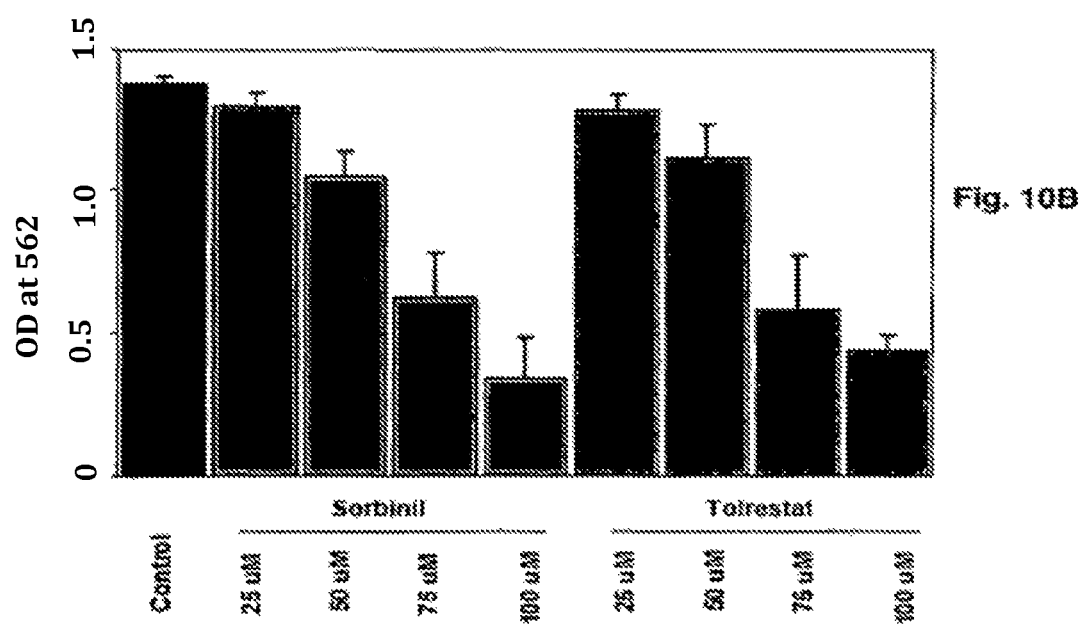

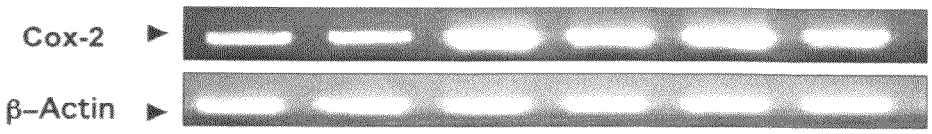
Fig. 11A
Fig. 11B
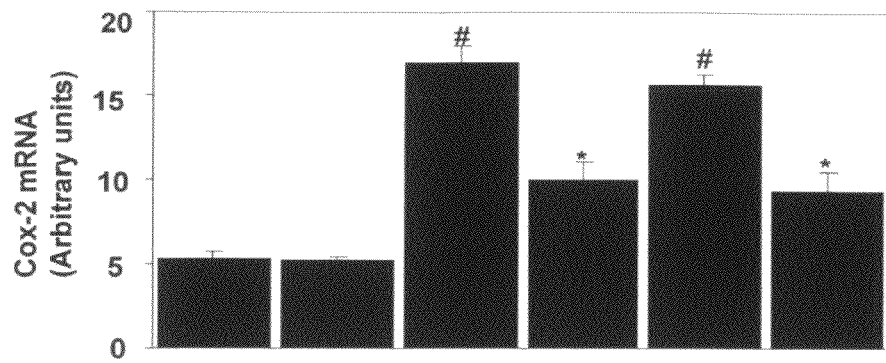
Fig. 11C
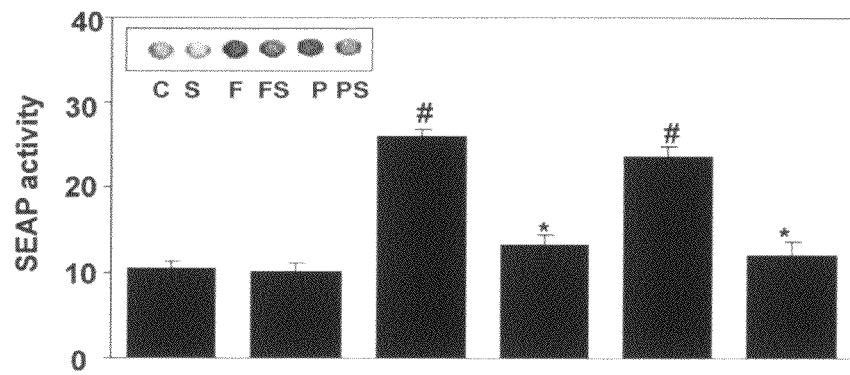
Fig. 11D
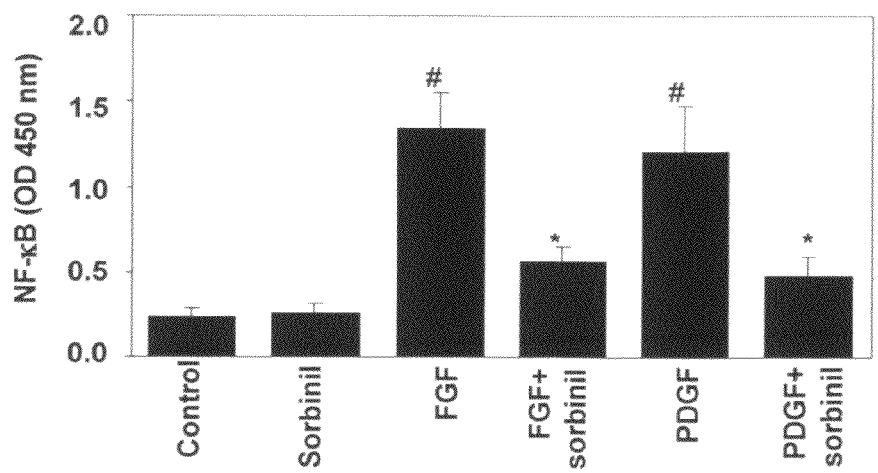
Fig. 11E

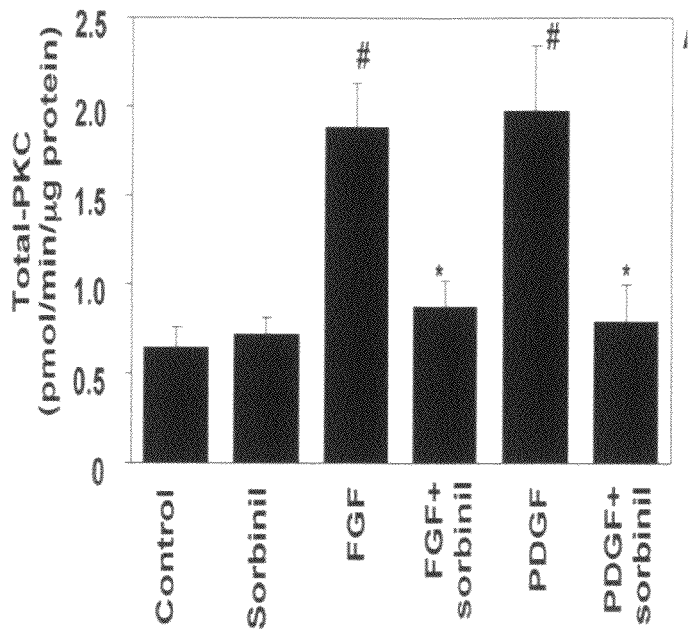
Fig. 12A
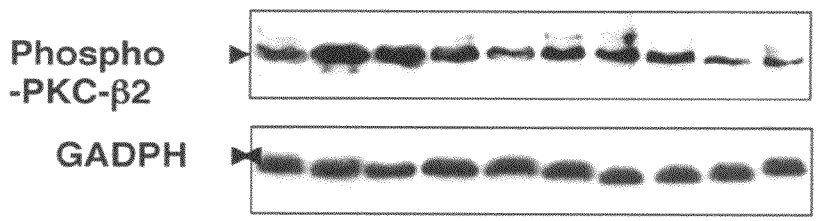
Fig. 12B
Fig. 12C
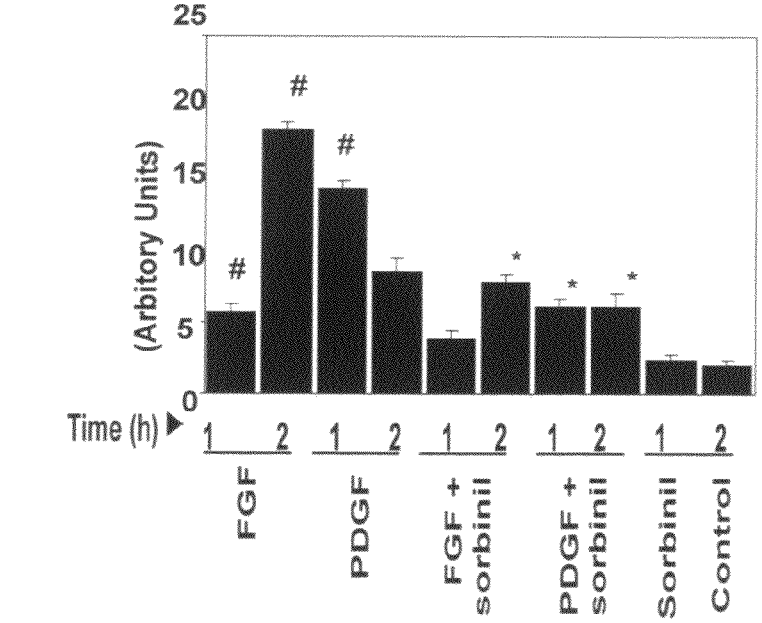
Fig. 12D

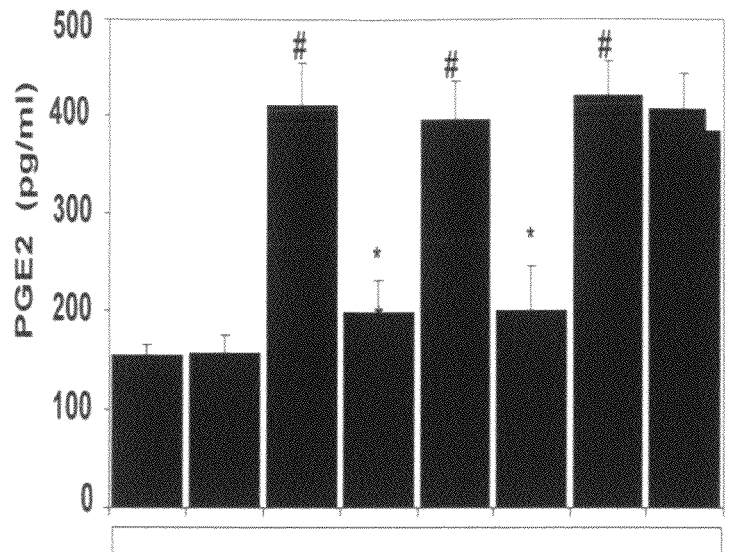
Fig. 15A
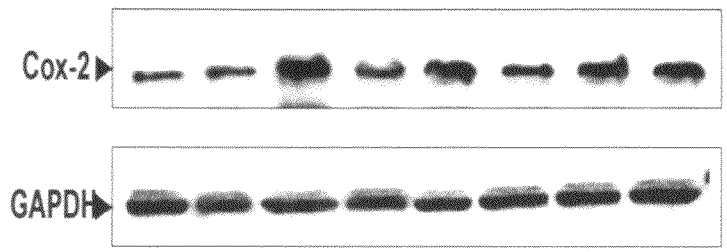
Fig. 15B
Fig. 15C
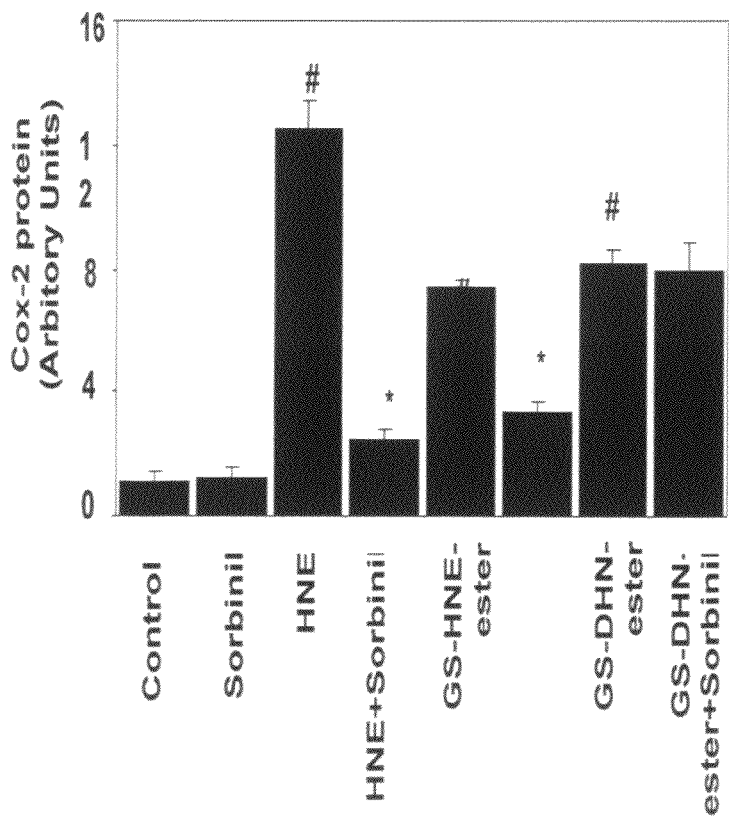
Fig. 15D

STRUCTURAL-BASED INHIBITORS OF THE GLUTATHIONE BINDING SITE IN ALDOSE REDUCTASE, METHODS OF SCREENING THEREFOR AND METHODS OF USE

CROSS-REFERENCE TO RELATED APPLICATIONS

This is a U.S. national stage application under 35 U.S.C. §371 of PCT/US2007/015322, filed Jun. 29, 2007, now expired, which is a continuation of and claims benefit of priority under 35 U.S.C. §120 of U.S. Ser. No. 11/478,069, filed Jun. 29, 2006, now abandoned, which is a continuation-in-part of and claims benefit of priority under 35 U.S.C. §120 of U.S. Ser. No. 11/282,801, filed Nov. 18, 2005, now U.S. Pat. No. 7,702,430, which is a non-provisional of and claims benefit of priority under 35 U.S.C. §119(e) of provisional U.S. Ser. No. 60/629,448, filed Nov. 19, 2004, now expired. Each above referenced application is incorporated by reference in its entirety.

FEDERAL FUNDING LEGEND

This invention was produced in part using funds obtained through Grants DK36118 and EY01677 from the National Institutes of Health. Consequently, the federal government has certain rights in this invention.

BACKGROUND OF THE INVENTION

1. Field of the Invention

The present invention relates generally to the fields of enzymology, protein structure and drug screening. More specifically, the present invention relates to the use of a crystalline structure of an aldose reductase complexed with NADPH and glutathione conjugate as a screening tool for inhibitors of aldose reductase and methods of treating a pathophysiological state involving aldose reductase signaling.

2. Description of the Related Art

Aldose reductase (AR) is a monomeric (a/b)$_8$-barrel (TIM barrel) protein belonging to the aldo-keto reductase (AKR) superfamily (1-3). Aldose reductase is a broad-specificity oxidoreductase catalyzing the reduction of a structurally-diverse range of aldehydes, including medium to long chain aldehydes, glucose and other aldo-sugars, aldehyde metabolites of neurotransmitters, isocorticosteroid hormones, and a variety of xenobiotic aldehydes to their corresponding alcohols (4). Reduction of glucose to sorbitol by aldose reductase constitutes the first and rate-limiting step of the polyol pathway that converts glucose to fructose via sorbitol dehydrogenase. Although this pathway usually represents a minor route of glucose metabolism, its activation during diabetes has been linked to the development of several clinically significant secondary complications such as nephropathy, neuropathy, retinopathy and cardiovascular related complications (4, 5). Several drugs that inhibit aldose reductase have been shown to prevent hyperglycemia-induced changes in nerve, kidney, and lens of experimental animals, although clinical trials with Type I and Type II diabetics have not been uniformly positive (4-6).

In addition to glucose, it has been shown that aldose reductase catalyzes the reduction of multiple biologically-active aldehydes generated by the peroxidation of membrane lipids and lipoproteins (7-9) or during glucose (10) and amine (11) metabolism. The aldehyde-detoxifying role of aldose reductase is supported by the observation that inhibition of the enzyme increases the accumulation of lipid peroxidation products (12, 13) that cause cytotoxicity (14, 15). The most abundant and toxic lipid peroxidation product is 4-hydroxy-trans-2-nonenal (16) which is efficiently reduced by aldose reductase in vitro and in vivo.

A primary role of aldose reductase in aldehyde detoxification is consistent with its structure. The active site of the enzyme is highly hydrophobic and contains few polar residues typically required for binding sugars with high specificity and affinity (2, 3). These features are, however, compatible with binding to hydrophobic lipid-derived aldehydes. Additionally, the substrate-specificity of aldose reductase is unusually broad, in part because the enzyme derives most of the energy required to achieve a substrate transition state from cofactor-binding (17). The active site environment exerts low stabilization on the transition state (18). Furthermore, it has been demonstrated recently that aldose reductase-catalyzed products mediate cytokine, chemokine, growth factor, and hyperglycemia-induced signaling that activates NF-kB and AP1, and regulates vascular epithelial cell (VEC) and human lens epithelial cell (HLEC) apoptosis, and vascular smooth muscle cell (VSMC) proliferation (15, 21, 22).

The range of aldehydes recognized by the aldose reductase active site is increased further by the ability of the enzyme to bind glutathione-aldehyde conjugates (19, 20), such as glutathionyl HNE. Given the high concentration of reduced glutathione in most cells and the highly electrophilic nature of several aldose reductase substrates, it is possible that reduction of aldehyde-glutathione conjugates, in addition to free aldehydes, may be a primary in vivo function of aldose reductase and that glucose may be an incidental substrate of the enzyme. Previous kinetic studies showed that glutathiolation increases the catalytic efficiency with which unsaturated aldehydes are reduced by aldose reductase (19), suggesting that the active site of aldose reductase contains a specific glutathione-binding domain (20). Nevertheless, the precise nature of glutathione binding to aldose reductase remained unclear.

There is a need in the art for three-dimensional structures of aldose reductase-glutathione-moiety binding complexes to understand the nature of glutathione-moiety binding at the active site. Also there is a need for methods incorporating computer modeling of three-dimensional structures to identify, design and test molecules with improved binding affinity. A further need for molecules that would be useful as therapeutics and/or modulators of aldose reductase-mediated physiological events is also present in the art.

The prior art is deficient in aldose reductase inhibitors useful in the treatment of cell proliferative diseases or the symptoms thereof. Specifically, the prior art is deficient in the lack of aldose reductase:NADPH:glutathione-like ligand based inhibitors that inhibit binding and reduction of glutathione-lipid aldehyde conjugates without inhibiting the detoxification of free aldehydes or inhibitors that ablate aldose reductase at the translational level. The present invention fulfills this long-standing need and desire in the art.

SUMMARY OF THE INVENTION

The present invention is directed to a crystalline structure of a ternary AR:NADPH:glutathione-like ligand complex. The crystalline structure diffracts x-rays for determining atomic co-ordinates of said complex with a resolution of about 3 Å to about 1.94 Å. The glutathione-like ligand interacts with both a glutathione binding domain and a carbonyl binding site within an active pocket formed by an AR:NADPH complex within the ternary structure. The present invention also is directed to a related crystalline structure comprising a ternary AR:NADPH:DCEG complex diffracts x-rays for determining atomic co-ordinates of the complex with a resolution of about 1.94 Å.

The present invention also is directed to a method of designing a potential inhibitor of glutathione-aldehyde conjugate binding to aldose reductase. The method comprises identifying a glutathione-like ligand that interacts with the glutathione binding domain, but does not block the carbonyl binding site, in the active pocket of an aldose reductase which has the three-dimensional conformation determined by DCEG binding to AR:NADPH. The identification of the potential inhibitor is based at least in part on a computer model of the crystalline AR:NADPH:DCEG ternary structure described herein.

The present invention is directed to a related method of screening for inhibitors of glutathione-aldehyde conjugate reduction by aldose reductase. The method comprises using the crystalline ternary structure described herein to design a potential inhibitor that binds to the glutathione binding domain in aldose reductase, but does not interfere with the carbonyl binding site. The design is based in part on computer modeling of the crystalline AR:NADPH:DCEG. The aldose reductase is complexed with the potential inhibitor and the aldose reductase:inhibitor complex is contacted with a lipid aldehyde and with the lipid aldehyde conjugated to glutathione. Detection of a reduced lipid aldehyde product, but not a reduced glutathione-lipid aldehyde product, screens for the inhibitor.

The present invention is directed further to the specific inhibitors of glutathione-aldehyde conjugate reduction designed and screened for by the methods described herein.

The present invention is directed further yet to a method of preventing a pathophysiological state or treating symptoms thereof resulting from aldose-reductase mediated signaling of a cytotoxic pathway in a subject. The method comprises administering a pharmacologically effective amount of the inhibitors of glutathione-aldehyde conjugate reduction described herein to the subject and inhibiting the reduction of a glutathione-aldehyde substrate via aldose reductase to prevent cytotoxic signaling in the subject. The cytotoxic signals could be generated by cytokines, chemokines, reactive oxygen species, endotoxins, growth factors, hyperglycemia and biologically active agents, e.g., bioterrorism agents.

The present invention is directed further still to a related method of treating a pathophysiological state or symptoms thereof resulting from aldose-reductase-mediated signaling in a cytotoxic pathway in a subject. The method comprises administering a pharmacologically effective amount of an inhibitor of aldose reductase to the subject thereby preventing aldose reductase mediated signaling. The aldose reductase inhibitor may be a small interfering RNA (siRNA) or an inhibitor that is effective to inhibit reduction of a glutathione-aldehyde conjugate by aldose reductase.

The present invention is directed further still to another related method of treating colon cancer in a subject. The method comprises administering a pharmacologically effective amount of an aldose reductase small interfering RNA (siRNA) to the subject to inhibit colon cancer cell proliferation thereby treating the colon cancer. The present invention is directed to a related method further comprising suppressing metastasis of the cancer to a metastatic cancer.

The present invention is directed further still to a method of suppressing metastasis of a cancer cell in a subject. The method comprises inhibiting aldose reductase activity within the cancer cell to prevent migration thereof through an extracellular matrix thereby suppressing metastasis of the cancer cell. Contacting the cancer cell with effective amounts of an siRNA or other aldose reductase inhibitor prevents migration of the cancer cell through an extracellular matrix.

Other and further aspects, features, and advantages of the present invention will be apparent from the following description of the embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate embodiments of the invention and therefore are not to be considered limiting in their scope.

FIG. 1A is the DCEG structure showing hydrogen bond interactions with aldose reductase and solvent as hashed lines. The dashed semi-circles denote hydrophobic interactions with the protein. FIG. 1B is a ribbon drawing of AR:NADPH (arrows) with DCEG bound (ball-n-stick), the β-strands in the $(\alpha/\beta)_8$ barrel and the mobile active loops A, B, and C.

FIG. 2A shows a top view of the human aldose reductase molecular surface (purple) with the active site occupied by DCEG (yellow). For clarity, solvent atoms have been omitted. FIG. 2B shows a close-up view of DCEG (yellow ball-stick) and the two waters bound in the aldose reductase active site. The active site residues: Tyr-48, His-110, Trp-110, and NADPH, sit at the base of the deep cleft where the DCEG dicarboxyethyl moiety is bound. Coloring is the same as for FIG. 1B.

FIGS. 6A-6E illustrate the effect of AR inhibition on LPS-induced cytokines. C57BL/6 mice (N=6 per group) were injected with sorbinil or vehicle for 3 days, then challenged with LPS (4 mg/kg). At the indicated times, TNF-a, IL-6, IL-12, interferon (IFN)-g, IL-1b, and monocyte chemo attractant protein (MCP)-1 levels in serum and in heart homogenates were determined (FIGS. 6A-6D). Prostaglandin E2 (PGE-2), cyclo-oxygenase 2 (COX-2), and nitrate levels were measured separately (FIG. 6E). Solid symbols, values from the mice injected with LPS; open symbols, values from the mice treated with LPS and sorbinil.

FIG. 7D shows the protective effect of AR inhibition on LPS-induced lethality as percent (%) survival of mice 48 h after LPS administration at increasing doses or LPS plus sorbinil administration either 24 h before LPS (pre-treatment) or 2 h after LPS (post-treatment). The LD50 for LPS alone was 14 mg/kg, that with sorbinil pre-treatment was 24 mg/kg, and with sorbinil post-treatment was 20 mg/kg (N=8 per group, *$p<0.001$).

FIG. 9G is a densitometric analysis of FIG. 9D. Bars represent mean±S.E. (n=4); # $p<0.001$ compared with treatment without the inhibitor or scrambled oligo transfected cells and * $p<0.01$; **, $p<0.001$ compared with growth factor treated cells.

FIGS. 10A-10D illustrate the effects of AR inhibitors on HT29 and A549 cell proliferation, induction of growth factors and protein expression. FIGS. 10A-10B demonstrate that sorbinil and zopolrestat and sorbinil and tolrestat inhibit HT29 and A549 cell proliferation, respectively. FIG. 10C demonstrates that sorbinil and zopolrestat inhibited production of PGE2 by HT29 cells. FIG. 10D demonstrates that sorbinil and tolrestat inhibit Cox-2 and iNOS expression in A549 cells.

FIGS. 11A-11D illustrate that inhibition of AR prevents growth factor-induced Cox-2 mRNA expression and NF-kB in colon cancer cells. Growth-arrested Caco-2 cells were pre-incubated with sorbinil or carrier for 24 h followed by stimulation with of BFGF or PDGF for 3 h. FIG. 11A-11B measure Cox-2 and β-actin expression, respectively. FIG. 11C is a densitometric analysis of FIG. 11A. FIG. 11D shows NF-kB-dependent reporter SEAP activity. The Inset in FIG. 11D shows the chemiluminescence of SEAP. FIG. 11E shows NF-kB activity. Bars represent mean±S.E. (n=4); # $p<0.01$ as compared to control cells. * $p<0.01$ compared cells treated with growth factors.

FIGS. 12A-12F illustrate that the inhibition of AR abrogates growth factor-induced PKC activation and growth in colon cancer cells. Quiescent Caco-2 cells were preincubated with sorbinil for 24 h followed by stimulation with BFGF or PDGF for 3 h. FIG. 12A shows membrane-bound PKC activity. Western blot analysis using antibodies against phsopho-PKC-b2 (FIG. 12B) and GAPDH (FIG. 12C) are depicted. FIG. 12D is a densitometric analysis of FIG. 12B. Growth-arrested Caco-2 cells were pre-incubated with or without sorbinil or tolrestat (FIG. 12E) or were transfected with AR antisense oligo followed by stimulation with BFGF or PDGF for 24 h and cell viability was measured by MTT assay (FIG. 12F). Bars represent mean±S.E. (n=4); # $p<0.01$ as compared to control cells. * $p<0.01$ compared to cells treated with growth factors.

FIGS. 13A-13B demonstrate that sorbinil prevents the synthesis S phase of the cell cycle in Caco-2 colon cancer cells and in A549 lung cancer cells, respectively. FIG. 13C demonstrates that sorbinil and tolrestat prevented the G1/S phase related proteins expression.

FIGS. 15A-15D illustrate the effect of AR-catalyzed reaction products on PGE2 and Cox-2 in colon cancer cells. The growth-arrested Caco-2 cells preincubated without or with sorbinil for 24 h were incubated with HNE, GS-HNE- or GS-DHN-esters for 24 h. FIG. 15A illustrates PGE2 production. Western blots were developed using antibodies against Cox-2 (FIG. 15B) and GAPDH (FIG. 15C). FIG. 15D is a densitometric analysis of FIG. 15B. Bars represent mean±S.E. (n=4); # $p<0.001$ Vs. control cells and * $p<0.01$ Vs. cells treated with aldehydes.

FIG. 18A demonstrates the difference between normal crypts and ACFs using light microscopy. FIG. 18B compares ACF formation in azoxymethane mice with or without sorbinil. FIG. 18C compares ACF formation in the presence of sorbinil in azoxymethane-treated mice and Knockout (KO) mice. FIG.

18D demonstrates that sorbinil inhibits azoxymethane-induced Cox-2 and iNOS expression in mice.

Figure 19A:
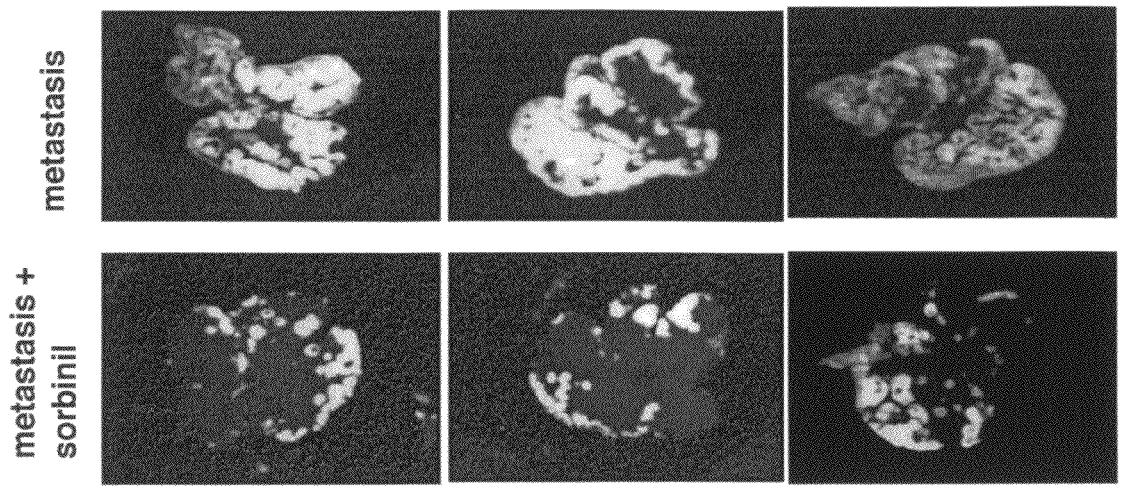
Figure 19B:
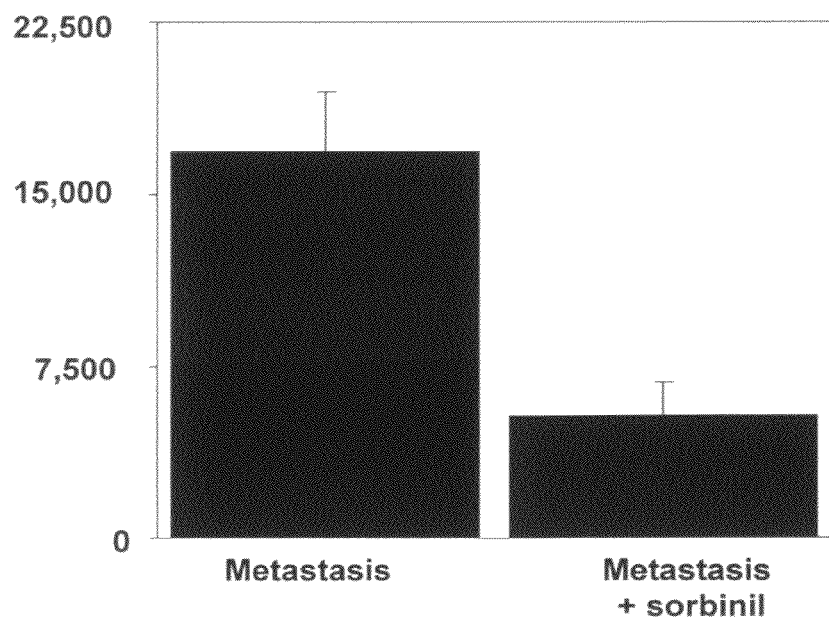

FIGS. 19A-19B illustrate the effects of sorbinil on induced HT29 metastatic tumor growth in a nude mouse liver model. FIG. 19A shows bioluminescent expression of green fluorescent protein (GFP) in metastic HT29 tumors with and without sorbinil. FIG. 19B converts the bioluminescence in FIG. 19A to pixel numbers.

Figure 20A:
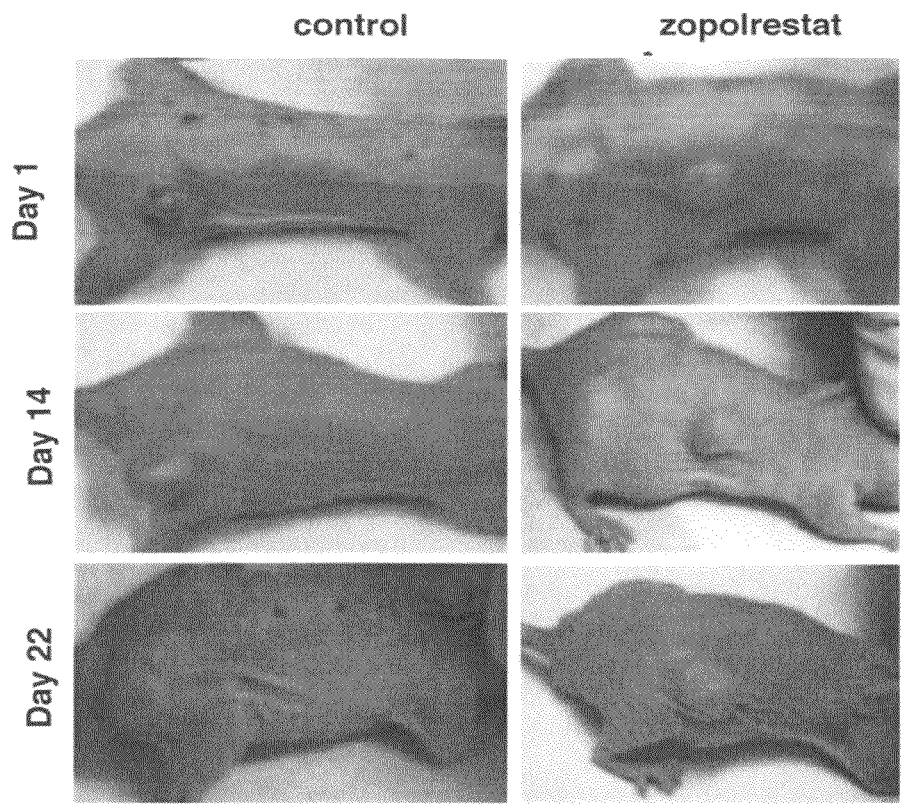
Figure 20B:
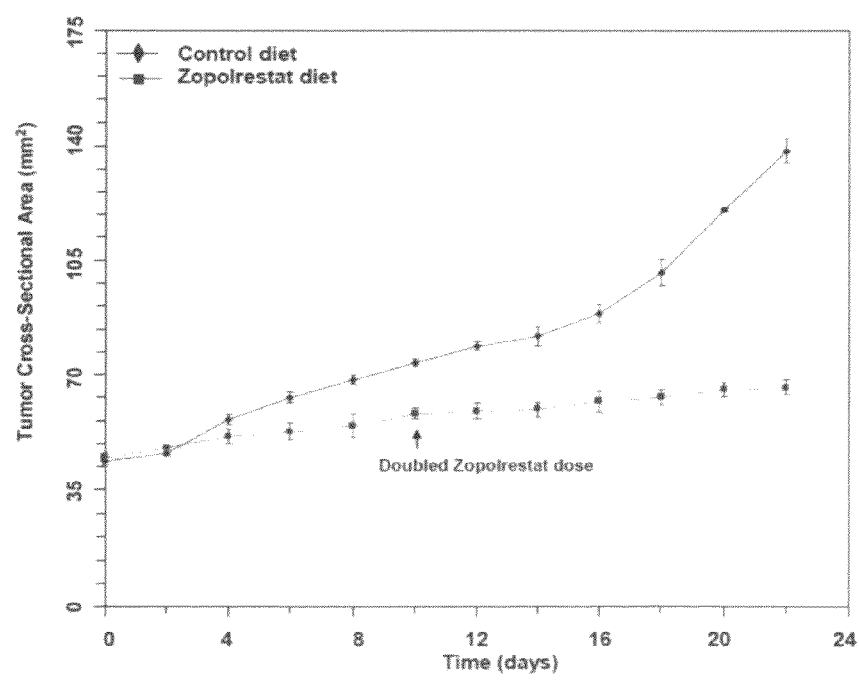

FIGS. 20A-20B illustrate that the growth of A540 xenografts in nu/nu nude mice was arrested in the presence of the AR inhibitor zopolrestat. Treatment was started when the tumor cross-sectional area was ~45 mm2 and continued for 29 days. Tumors were measured in two dimensions using calipers.

Figure 21A:
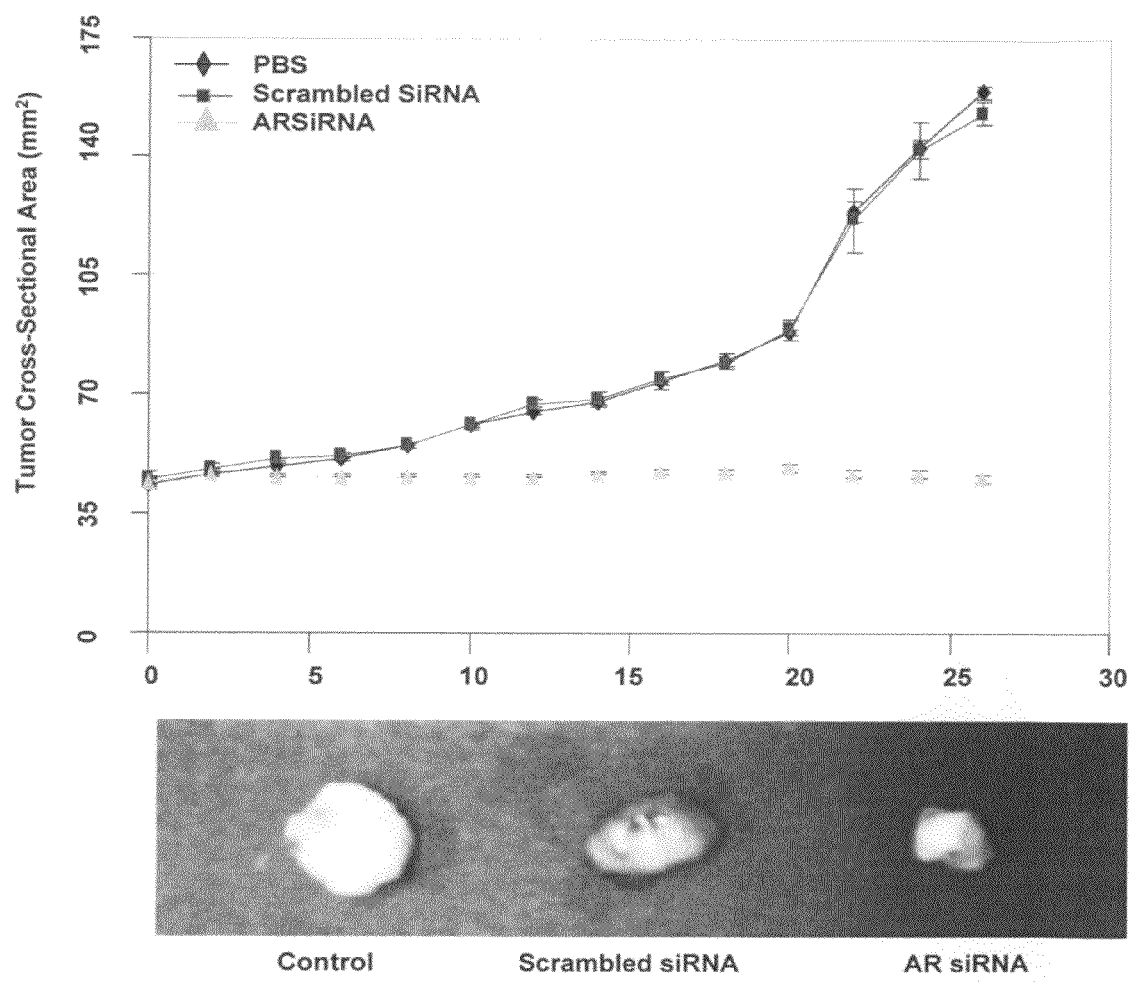
Figure 21B:
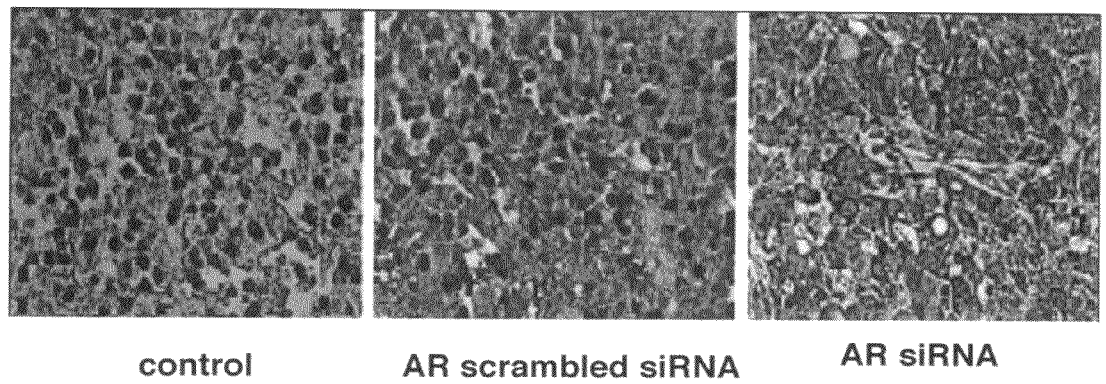
Figure 21C:
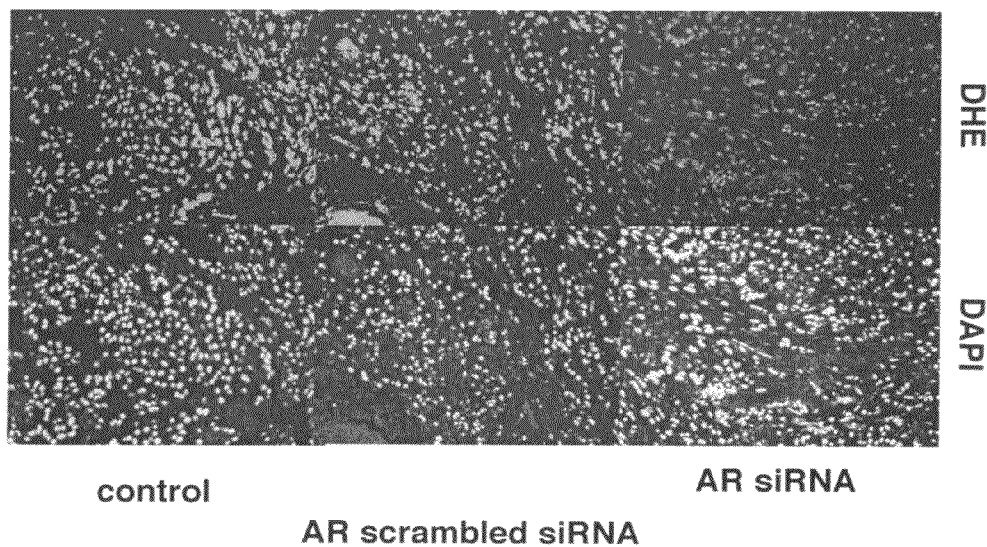

FIGS. 21A-21C illustrate that siRNA inhibition of AR prevents tumorigenesis and production of reactive oxygen species in A549 lung cancer xenografts. FIG. 21A shows the tumor cross-sectional area of At549 tumors in control and siRNA treated mice. FIGS. 21B-21C are histological sections of A549 xenografts from control and siRNA treated mice demonstrating inhibition of AR expression and ROS production, respectively.

DETAILED DESCRIPTION OF THE INVENTION

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

As used herein, the term "subject" refers to any target of the treatment.

The following abbreviations are used herein: AR: aldose reductase or human aldose reductase, ARL2, E.C. 1.1.1.21; sAR: *Sus scrofa* (Pig) aldose reductase, AR, E.C. 1.1.1.21; ARI: aldose reductase inhibitor; NADPH: dihydro-nicotinamide-adenine-dinucleotide phosphate; NADP: nicotinamide-adenine-dinucleotide phosphate; DCEG: S-(1,2-dicarboxyethyl) glutathione, γ-glutamyl-S-(1,2-dicarboxyethyl) cysteinylglycine; ROS: reactive oxygen species; CNS: Crystallography and NMR Software; GS or GSH: glutathione; γ-glutamylcysteinylglycine; GS-HNE: glutathionyl-4-hydroxynonenal; GS-DHN: glutathionyl-1,4-dihydroxynonene; PGE2: prostaglandin E2; MTT: [3-(4,5-dimethylthiazol-2-yl)-5-(3-carboxymethoxyphenyl)-2-(4-sulfophenyl)-2H-tetrazolium salt]; BFGF: basic fibroblast growth factor; Cox: cyclooxygenase; DHN: 1,4-dihydroxynonene; HNE: 4-hydroxy-trans-2-nonenal; NF-κB: nuclear factor kappa binding protein; PKC: Protein kinase C; PDGF: platelet derived growth factor; SEAP: Secretory alkaline phosphatase; LPS:lipopolysaccharide; IKK: inhibitor of kappaB kinase; PLC: phospholipase C; iNOS: inducible NO synthase; VSMC: vascular smooth muscle cells; MAPK: mitogen activated protein kinase AOM: azoxymethane; ACF: aberrant crypt foci; and KO: Knockout.

In one embodiment of the present invention there is provided a crystalline structure of a ternary AR:NADPH:glutathione-like ligand complex, wherein the crystalline structure diffracts x-rays for determining atomic co-ordinates of the complex with a resolution of about 3 Å to about 1.94 Å and wherein the glutathione-like ligand interacts with both a glutathione binding domain and a carbonyl binding site within an active pocket formed by an AR:NADPH complex within the ternary structure.

In one aspect of this embodiment, the ternary structure has a space group of P2$_1$ and a unit cell with dimensions of a=47.21 Å, b=66.72 Å and c=49.30 Å. In this aspect the crystalline structure has the protein data base accession code of 1Q9N. In a related aspect the active pocket comprises three flexible loops A, B, and C where the glutathione-like ligand interacts with at least the C loop. An example of the glutathione-like ligand is γ-glutamyl-S-(1,2-dicarboxyethyl) cysteinylglycine.

In a related embodiment there is provided a crystalline structure of a ternary AR:NADPH:DCEG complex wherein the crystalline structure diffracts x-rays for determining atomic co-ordinates of the complex with a resolution of about 1.94 Å. The crystalline structure has the protein data base accession code of 1Q9N.

In another embodiment of the present invention there is provided a method of designing a potential inhibitor of glutathione-aldehyde conjugate binding to aldose reductase, comprising identifying a glutathione-like ligand that interacts with the glutathione binding domain, but does not block the carbonyl binding site, in the active pocket of an aldose reductase having a three-dimensional conformation determined by DCEG binding to AR:NADPH, where the identification is based at least in part on a computer model of the crystalline AR:NADPH:DCEG ternary structure described supra.

Further to this embodiment the method comprises screening the potential inhibitors for inhibition of glutathione-aldehyde conjugate reduction by aldose reductase. Screening may comprise contacting aldose reductase with the potential inhibitor, contacting the AR:inhibitor complex with a lipid aldehyde and with the lipid aldehyde conjugated to glutathione and detecting only a reduced lipid aldehyde product.

In this embodiment, the glutathione-binding domain comprises residues Trp-20, Trp-79, Trp-111, Trp-219, Phe-122, Val-47, Cys-298, Ala-299, Leu-300, Ser-302 and Leu-301. In an aspect of this embodiment the residues Ser-302, Ala-299, Leu-300, and Leu-301 comprise a C loop of the active pocket. Particularly in this aspect Ser-302, Ala-299, Leu-300, and Leu-301 interact with the glutathione-like ligand via a network of water molecules within the C loop. Also in this embodiment the carbonyl binding site comprises residues Tyr-48, His-110, and Trp-111 and NADPH. A representative example of a glutathione-like ligand has a γ-glutamylcysteinylglycine backbone with an S-cysteinyl-substituted moiety.

In a related embodiment there is provided a method of screening for inhibitors of glutathione-aldehyde conjugate reduction by aldose reductase, comprising using the crystalline structure of the ternary AR:NADPH:DCEG described supra to design a potential inhibitor that binds to the glutathione binding domain in aldose reductase, but does not interfere with the carbonyl binding site, where the design is based at least in part on computer modeling; contacting aldose reductase with the potential inhibitor; contacting the AR:inhibitor complex with a lipid aldehyde and with the lipid aldehyde conjugated to glutathione; and detecting a reduced lipid aldehyde product, but not a reduced glutathione-lipid aldehyde product, thereby screening for the inhibitor.

In yet another embodiment there is provided an inhibitor of glutathione-aldehyde conjugate reduction by aldose reductase designed by the methods described supra.

In a related embodiment there is provided a method of preventing a pathophysiological state or treating symptoms thereof resulting from aldose-reductase mediated signaling of a cytotoxic pathway in a subject, comprising administering a pharmacologically effective amount of the inhibitor described supra to the subject; and inhibiting the reduction of a glutathione-aldehyde substrate via aldose reductase, thereby preventing the cytotoxic signaling in the subject. An example of a pathophysiological state is colon cancer or one comprising inflammation. An example of a cytotoxic pathways are PLC/PKC/NF-κB or other NF-κB dependent inflammatory processes, for example, due to a bacterial infection.

In another related embodiment there is provided a method of treating a pathophysiological state or symptoms thereof resulting from aldose reductase-mediated signaling in a cytotoxic pathway in a subject, comprising administering a pharmacologically effective amount of an inhibitor of aldose reductase to the subject thereby preventing aldose reductase mediated signaling.

In one aspect of this embodiment the inhibitor may be a small interfering RNA (siRNA). An example of an siRNA has the sequence of SEQ ID NO: 1. Alternatively, the siRNA may comprise a vector effective to transfect a cell characteristic of the pathophysiological state. An example of such a cell is a colon cancer cell, a lung cancer cell or a metastatic cancer cell derived therefrom.

In another aspect of this embodiment the inhibitor may be effective to inhibit reduction of a glutathione-aldehyde conjugate by aldose reductase. In this aspect the inhibitor may interact with a glutathione binding domain, but does not block a carbonyl binding site, in an active pocket of an aldose reductase having a three-dimensional conformation determined by DCEG binding to AR:NADPH. Also, the glutathione-binding domain may comprise residues Trp-20, Trp-79, Trp-111, Trp-219, Phe-122, Val-47, Cys-298, Ala-299, Ser-302, Leu-300, and Leu-301. In addition, in this aspect the active pocket may comprise three flexible loops A, B, and C such that the inhibitor interacts with at least the C loop. In a representative example, the C loop comprises residues Ser-302, Ala-299, Leu-300, and Leu-301. These residues may interact with the inhibitor via a network of water molecules within the C loop. Furthermore, in this aspect the carbonyl binding site may comprise residues Tyr-48, His-110, and Trp-111 and NADPH. In this aspect the inhibitor may have a γ-glutamylcysteinylglycine backbone with an S-cysteinyl-substituted moiety.

In a related aspect the inhibitor may be 3,4-dihydro-4-oxo-3-[[5-(trifluoromethyl)-2-benzothiazolyl]methyl]-1-phthalazineacetic acid, (S)-6-fluorospiro[chroman-4,4'-imidazolidine]-2,5'-dione, N-[(5-trifluoromethyl)-6-methoxy-1-naphthalenyl]thioxomethyl}-N-methylglycine, 3-(4-bromo-2-fluorobenzyl)-3,4-dihydro-4-oxo-1-phthalazineacetic acid, 5-[(Z,E)-.β-methylcinnamylidene]-4-oxo-2-thioxo-3-thiazolideneacetic acid, 3-(4-bromo-2-fluorobenzyl)-7-chloro-3,4-dihydro-2,4-dioxo-1(2H) quinazoline acetic acid, 3,4-dihydro-3-oxo-4-[(4,5,7-trifluoro-2-benzothiazolyl)methyl]-2H-1,4-benzothiazine-2-acetic acid, N-[3,5-dimethyl-4-[(nitromethyl)sulfonyl]phenyl]-2-methyl benzeneacetamide, (2S,4S)-6-fluoro-2',5'-dioxospiro(chroman-4,4'-imidazolidine)-2-carboxamide, 2-[(4-bromo-2-fluoro phenyl)methyl]-6-fluorospiro[isoquinoline-4(1H), 3'-pyrrolidine]-1,2',3,5'(2H)-tetrone, 2R,4R-6,7-dichloro-4-hydroxy-2-methylchroman-4-acetic acid, 2R,4R-6,7-dichloro-6-fluoro-4-hydroxy-2-methylchroman-4-acetic acid, 3,4-dihydro-2,8-diisopropyl-3-oxo-2H-1,4-benzoxazine-4-acetic acid, d-2-methyl-6-fluoro-spiro(chroman-4',4'-imidazolidine)-2',5'-dione, 2-fluoro-spiro(9H-fluorene-9,4'-imidazolidine)-2',5'-dione, 2,7-di-fluoro-spiro(9H-fluorene-9,4'-imidazolidine)-2',5'-dione, 2,7-di-fluoro-5-methoxy-spiro(9H-fluorene-9,4'-imidazolidine)-2',5'-dione, 7-fluoro-spiro(5H-indenol[1,2-b]pyridine-5,3'-pyrrolidine)-2,5'-dione, d-cis-6'-chloro-2',3'-dihydro-2'-methyl-spiro-(imidazolidine-4,4'-4'H-pyrano(2,3-b)pyridine)-2,5-dione, spiro[imidazolidine-4,5'(6H)-quinoline]-2,5-dione-3'-chloro-7,'8'-dihydro-7'-methyl-(5'-cis), 3,4-dihydro-3-(5-fluorobenzothiazol-2-ylmethyl)-4-oxophthalazin-1-yl-acetic acid, 3-(5,7-difluorobenzothiazol-2-ylmethyl)-3,4-dihydro-4-oxophthalazin-1-yl-acetic acid, 3-(5-chlorobenzothiazol-2-ylmethyl)-3,4-dihydro-4-oxophthalazin-1-yl-acetic acid, 3-(5,7-dichlorobenzothiazol-2-ylmethyl)-3,4-dihydro-4-oxophthalazin-1-yl-acetic acid, 3,4-dihydro-4-oxo-3-(5-trifluoromethylbenzoxazol-2-ylmethyl)phthalazin-1-yl-acetic acid, 3,4-dihydro-3-(5-fluorobenzoxazol-2-ylmethyl)-4-oxophthalazin-1-yl-acetic acid, 3-(5,7-difluorobenzoxazol-2-ylmethyl)-3,4-dihydro-4-oxophthalazin-1-yl-acetic acid, 3-(5-chlorobenzoxazol-2-ylmethyl)-3,4-dihydro-4-oxophthalazin-1-y-lacetic acid, 3-(5,7-dichlorobenzoxazol-2-ylmethyl)-3,4-dihydro-4-oxophthalazin-1-yl-acetic acid.

In both aspects of this embodiment the pathophysiological state may be a cancer. An example of a cancer is colon cancer, lung cancer or a metastatic cancer derived therefrom. An example of a metastatic cancer is a liver cancer. Also, in both aspects the pathophysiological state may be characterized by inflammation. In representative examples the inflammation may be associated with a lung cancer or may be induced by lipopolysaccharide (LPS). Furthermore, the cytotoxic pathway may be a PLC/PKC/NF-κB pathway. Inhibition of this pathway may inhibit signaling by one or more of NF-κB, 2 prostaglandin (PGE2) or cyclooxygenase (Cox-2).

In yet another related embodiment there is provided a method of treating a cancer in a subject, comprising administering a pharmacologically effective amount of an aldose reductase small interfering RNA (siRNA) to the subject to inhibit cancer cell proliferation thereby treating the cancer. Further to this embodiment the method may comprise suppressing metastasis of the cancer to a metastatic cancer. In this further embodiment the cancer may be a colorectal cancer and the metastatic cancer may be a liver cancer. In both embodiments the cancer may be colon cancer, lung cancer or a metastatic cancer derived therefrom. Also, the siRNA or vector comprising the same are as described supra.

In yet another embodiment of the present invention there is provided a method method for suppressing metastasis of a cancer cell in a subject, comprising inhibiting aldose reductase activity within the cancer cell to prevent migration thereof through an extracellular matrix thereby suppressing metastasis of the cancer cell. In this embodiment the cancer cell may be a colon cancer cell or a lung cancer cell.

In one aspect of this embodiment inhibiting aldose reductase activity within the cancer cell may comprise contacting the cell with an amount of a small interfering RNA effective to ablate aldose reductase RNA translation within the cancer cell. The siRNA is as described supra. In another aspect inhibiting aldose reductase activity within the cancer cell comprises contacting the cancer cell with an effective amount of an aldose reductase inhibitors described supra.

Provided herein is a crystallized ternary complex of human aldose reductase bound to NADPH and γ-glutamyl-S-(1,2-dicarboxyethyl)cysteineinylglycine, a competitive inhibitor of AR-catalyzed reaction of glutathionyl-propanal (19). The ternary structure confirms the presence of two active sites within AR:NADPH. The crystal structure was determined to 1.9 Å and revealed novel interactions between the glutathione backbone and active site residues.

The ternary structure demonstrates that DCEG binding induces a significant conformational reorganization of the active site. The carboxylate moiety of DCEG binds in the aldose reductase active site, while the GS C-terminus binds in the aldose reductase loop C. The binding of glutathione to aldose reductase significantly reorients loops A and B of the protein thereby providing an induced-fit mechanism that enables the active site to bind substrates of different sizes. This induced-fit rearrangement and the multiplicity of specific interactions at the aldose reductase active site with glutathione are indicative of a highly selective glutathione-binding domain.

Thus, the ternary structure is used in methods of developing therapeutic inhibitors that selectively prevent binding of glutathione-conjugated substrates. These structure-based inhibitors are designed using rational drug design in conjunction with computer modeling of the coordinates of the ternary crystalline structure. The coordinates indicate that structure based inhibitors could be synthesized which will inhibit the glutathione-aldehyde binding site without affecting the detoxification role of aldose reductase since it will not inhibit the carbonyl binding site. For example, the specific inhibitors would not interfere the detoxification of free aldehydes, such as 4-hydroxy trans-2 nonenal which is formed during lipid peroxidation.

Also provided are the designed structure-based inhibitors and methods of screening therefor. The aldose reductase inhibitors may function through one of two mechanisms. Either remodeling of the aldose reductase loop-C backbone or steric hindrance of the GS-specific binding site in this loop may prevent the binding of GS-conjugates and their entry into the aldose reductase active site. A designed inhibitor may comprise a γ-glutamylcysteinylglycine backbone with an S-cysteinyl-substituted moiety that does not interfere with aldehyde binding to aldose reductase at the carbonyl active site.

These designed inhibitors may be tested for selective inhibition of glutathione-aldehyde binding in a screening assay. A selective inhibitor will form a complex with aldose reductase in the presence of NADPH by binding or otherwise interacting within the glutathione-binding domain in aldose reductase. Such a specific inhibitor will exclude glutathione-aldehyde binding and prevent subsequent reduction of the glutathione-aldehyde, but will not interfere with binding and reduction of the unconjugated lipid aldehyde at the carbonyl active site. Such screening assays are standard and well within the ordinary skill of an artisan to implement without undue experimentation or burden.

It is contemplated that other AKR proteins have similar sites that are capable of high affinity interactions with glutathione or glutathione conjugates. The same or similar techniques used to elucidate the AR:NADPH:DCEG ternary structure may be used to determine the coordinates of other similar AKR:ligand three-dimensional structures. Such crystal structures may be used in the design of relevant therapeutic inhibitors.

It is further contemplated that the aldose reductase inhibitors provided herein may be used as a therapeutic to treat or modulate or otherwise alter a pathophysiological state or event or symptoms thereof mediated by reduction products of aldose reductase as part of the pathology. For example, and without being limiting, a specific inhibitor could prevent glutathione binding without affecting the carbonyl reduction necessary to detoxify lipid aldehydes. Such inhibition could regulate TNF-α, growth factor, lipopolysaccharide, and hyperglycemia-induced cytotoxicity mediated by reactive oxygen species in, for example, the PLC/PKC/NF-κB pathway. It is further contemplated that such an inhibitor may limit access of other bulky molecules, such as glucose, to the AR active site thereby reducing other adverse effects of hyperglycemia as mediated by AR's role in the osmotic stress pathway.

Also provided are methods of inhibiting cell proliferation and/or metastasis of a cancer, e.g., colon cancer or lung cancer, with one or more of aldose reductase inhibitor compounds. These aldose reductase inhibitor compounds are known in the art and can be easily synthesized by those skilled in the art using conventional methods of organic synthesis tolrestat or. These inhibitors are listed in Table 1. Other aldose reductase inhibitors will be known to those skilled in the art. Common chemical names or other designations are in parentheses where applicable.

TABLE 1

Aldose Reductase Inibitors 1. 3,4-dihydro-4-oxo-3-[[5-(trifluoromethyl)-2-benzothiazolyl]methyl]-1-phthalazineacetic acid (zopolrestat);
2. (S)-6-fluorospiro[chroman-4,4'-imidazolidine]-2,5'-dione (sorbinil);
3. N-[(5-trifluoromethyl)-6-methoxy-1-naphthalenyl]thioxomethyl}-N-methylglycine (tolrestat);
4. 3-(4-bromo-2-fluorobenzyl)-3,4-dihydro-4-oxo-1-phthalazineacetic acid (ponalrestat);
5. 5-[(Z,E)-β-methylcinnamylidene]-4-oxo-2-thioxo-3-thiazolideneacetic acid (epalrestat);
6. 3-(4-bromo-2-fluorobenzyl)-7-chloro-3,4-dihydro-2,4-dioxo-1(2H) quinazoline acetic acid (zenarestat);
7. 3,4-dihydro-3-oxo-4-[(4,5,7-trifluoro-2-benzothiazolyl)methyl]-2H-1,4-benzothiazine-2-acetic acid (SPR-210);
8. N-[3,5-dimethyl-4-[(nitromethyl)sulfonyl]phenyl]-2-methylbenzeneacetamide (ZD5522);
9. (2S,4S)-6-fluoro-2',5'-dioxospiro(chroman-4,4'-imidazolidine)-2'-carboxamide (fidarestat);
10. 2-[(4-bromo-2-fluorophenyl)methyl]-6-fluorospiro[isoquinoline-4(1H),3'-pyrrolidine]-1,2',3,5'(2H)-tetrone (minalrestat);
11. 2R,4R-6,7-dichloro-4-hydroxy-2-methylchroman-4-acetic acid;
12. 2R,4R-6,7-dichloro-6-fluoro-4-hydroxy-2-methylchroman-4-acetic acid;
13. 3,4-dihydro-2,8-diisopropyl-3-oxo-2H-1,4-benzoxazine-4-acetic acid
14. d-2-methyl-6-fluoro-spiro(chroman-4',4'-imidazolidine)-2',5'-dione;
15. 2-fluoro-spiro(9H-fluorene-9,4'-imidazolidine)-2',5'-dione;
16. 2,7-di-fluoro-spiro(9H-fluorene-9,4'-imidazolidine)-2',5'-dione;
17. 2,7-di-fluoro-5-methoxy-spiro(9H-fluorene-9,4'-imidazolidine)-2',5'-dione;
18. 7-fluoro-spiro(5H-indenol[1,2-b]pyridine-5,3'-pyrrolidine)-2,5'-dione;
19. d-cis-6'-chloro-2',3'-dihydro-2'-methyl-spiro-(imidazolidine-4,4'-4'H-pyrano(2,3-b)pyridine)-2,5-dione;
20. spiro[imidazolidine-4,5'(6H)-quinoline]-2,5-dione-3'-chloro-7,'8'-dihydro-7'-methyl-(5'-cis);
21. 3,4-dihydro-3-(5-fluorobenzothiazol-2-ylmethyl)-4-oxophthalazin-1-yl-acetic acid;
22. 3-(5,7-difluorobenzothiazol-2-ylmethyl)-3,4-dihydro-4-oxophthalazin-1-yl-acetic acid;
23. 3-(5-chlorobenzothiazol-2-ylmethyl)-3,4-dihydro-4-oxophthalazin-1-yl-acetic acid;

TABLE 1-continued

Aldose Reductase Inibitors 24. 3-(5,7-dichlorobenzothiazol-2-ylmethyl)-3,4-dihydro-4-oxophthalazin-1-yl-acetic acid;
25. 3,4-dihydro-4-oxo-3-(5-trifluoromethylbenzoxazol-2-ylmethyl)phthalazin-1-yl-acetic acid;
26. 3,4-dihydro-3-(5-fluorobenzoxazol-2-ylmethyl)-4-oxophthalazin-1-yl-acetic acid;
27. 3-(5,7-difluorobenzoxazol-2-ylmethyl)-3,4-dihydro-4-oxophthalazin-1-yl-acetic acid;
28. 3-(5-chlorobenzoxazol-2-ylmethyl)-3,4-dihydro-4-oxophthalazin-1-y-lacetic acid;
29. 3-(5,7-dichlorobenzoxazol-2-ylmethyl)-3,4-dihydro-4-oxophthalazin-1-yl-acetic acid.

Alternatively, the present invention provides methods of inhibiting expression of aldose reductase at the RNA translational level. It is contemplated that administration of aldose reductase small interfering RNAs (siRNA) is useful in the treatment of a pathophysiological state, such as a cancer, for example, but not limited to, colon cancer, lung cancer or a metastatic cancer derived therefrom. The siRNAs may be useful in the treatment of or alleviation of other pathophysiological conditions or symptoms resulting from aldose reductase-mediated signaling of a cytotoxic pathway. For example, conditions exhibiting or characterised by inflammation, e.g., lipopolysaccharide-induced inflammation, may benefit from such treatment or therapy.

In addition it is contemplated that the aldose reductase inhibitors described herein also may inhibit metastasis of a cancer cell to form a metastatic cancer, for example, but not limited to, the metastasis of a colon cancer, such as a colorectal cancer, to the liver. Contacting a cancer cell with one or more of these inhibitors is effective to prevent migration of a cancer cell through an extracellular matrix. As is apparent to one of ordinary skill in the art contact includes any known method effective to provide the aldose reductase inhibitor to the cell.

The design methodology for siRNAs is known in the art and/or they may be obtained commercially. For example, without being limiting, an siRNA effective as a therapeutic may have the sequence of SEQ ID NO: 1. siRNAs may be administered to a subject as the naked oligomer or as comprising a suitable transfection vector or with a carrier molecule or moiety as are known and standard in the art.

It is standard in the art to formulate a therapeutic compound with a pharmaceutically acceptable carrier as a pharmaceutical composition. It is also standard in the art to determine dose, dosage and routes of administration of the therapeutic or pharmaceutical compounds. Such determination is routinely made by one of skill in the art based on the individual and the particular pathophysiological state or symptoms exhibited by the patient and the patients history.

The following examples are given for the purpose of illustrating various embodiments of the invention and are not meant to limit the present invention in any fashion.

EXAMPLE 1

Aldose Reductase Crystallography and Inhibitor Design

Overexpression and Purification of Recombinant Human AR

Recombinant human AR was over expressed and purified as described previously (23). In brief, the cell extract was subjected to chromatofocusing on PBE94 (Pharmacia LKB Biotechnology Inc.) followed by hydroxylapatite column chromatography and reactive blue affinity chromatography as the final step. All purification buffers contained 1 mM dithiothretiol (DTT).

Crystallization of the Ternary Complex

Purified AR was concentrated by ultrafiltration (Amicon YM-10 membrane) to ~10 mg/ml. Prior to crystallization, 10 mg/ml AR in phosphate buffer (10 mM phosphate pH 7.1, 0.5 mM EDTA, 10 mM DTT) was incubated with NADPH and DCEG (γ-glutamyl-S-(1,2-dicarboxyethyl) glutathione) at a AR:NADPH:DCEG molar ratio of 1:2:2 for 10 min at 4° C. The ternary complex was crystallized using the vapor diffusion method at 4° C. The protein:ligand solution was mixed with an equal volume of 22% (w/v) polyethylene glycol (PEG) 4000 in 100 mM sodium citrate (pH 5.0) and 6 ml of droplets were placed above an identical well solution.

Data Collection

X-ray data were collected using a MacScience DIP 2030H area detector and a M06XHF rotating anode X-ray generator operating at 50 KV and 90 Ma and equipped with Göbel collimating optics (Bruker AXS). The first crystal, $0.1 \times 0.1 \times 0.1$ mm$^3$, was flash-cooled, without the addition of cryoprotectants to the drop, using nitrogen boil-off (Cryo Industries). Weak ice rings were observed in the diffraction pattern. The protein crystallized in the $P2_1$ monoclinic space group with cell dimensions a=47.21 Å, b=66.72 Å, c=49.30 Å, a=g=90.00°, b=92.24°. This crystal form was not observed previously for any AR crystal structures. Based upon the Matthews coefficient (24), there was predicted to be one AR molecule per au. The data were processed to 2.6 Å resolution using the programs HKL (25).

A second crystal was soaked in mother liquor containing 20% glycerol (v/v) and 25 mM of DCEG and flash cooled. Diffraction data collected from crystal 2 were processed with HKL to 1.94 Å resolution and was used for high-resolution refinements of the model. Space group and unit cell dimensions were similar to crystal 1. Data collection and processing statistics, including atomic coordinates and structure factors, for crystal 2, i.e., 1Q9N, are shown in Table 2.

TABLE 2

Summary of crystallographic statistics
PDB Accession ID

| | $P2_1$ |
|---|---|
| Space group | |
| Cell | |
| a (Å) | 47.21 |
| b (Å) | 66.72 |
| c (Å) | 49.30 |
| a (°) | 90.00 |
| b (°) | 92.24 |
| g (°) | 90.00 |
| Data Collection | |
| Resolution range, Å | 30-1.94 |
| $R_{merge}$, * % | 9.0 (30.7) |
| Unique observations | 22,256 |
| Average I/s(I) * | 13.8 (4.4) |
| Redundancy * | 5.8 (3.2) |
| Completeness * % | 97.7 (87.8) |

TABLE 2-continued

Summary of crystallographic statistics
PDB Accession ID

| | $P2_1$ |
|---|---|
| Refinement Statistics | |
| R-factor (%) * | 21.1 (26.4) |
| $R_{free}$, * % | 26.0 (34.9) |
| r.m.s. deviations | |
| Bonds (Å) | 0.006 |
| Angles (°) | 1.3 |
| Model Statistics | |
| No. residues in most favored region | 249 |
| Additional allowed | 25 |
| Generously allowed | 3 |
| Disallowed | 0 |
| No. Protein Atoms | 2517 |
| No. Ligand atoms | 76 |
| No. Waters | 165 |
| Average B factor (Å$^2$) | 20.4 |
| Protein (Å$^2$) | 19.4 |
| Waters (Å$^2$) | 25.1 |

* Values for the highest-resolution shells are in parentheses.

Structure Determination and Refinement

The $P2_1$ crystal form structure was solved by molecular replacement using the program EPMR (26) with the 1ADS (3) structure as a search model. Initial model building in CNS (27) used data collected to 2.6 Å resolution from crystal 1. Since this data set contained scattering noise from ice crystals, the initial refinement contained resolutions shells with unusually high R-factors. An alternate processing of this data, which removed all reflections in the narrow resolution range affected by the ice, also was used for model building.

The PMB suite of programs (28) was used to generate a test set using 5% of the reflections chosen in thin shells equally spaced in 1/d. The PMB suite was used as an interface to the structure refinement program CNS to simplify and partially automate the structure refinement process. The variable sigma model of B-factor restraints (29) was implemented in CNS and the parameters optimized to minimize the free R. This led to a significant reduction in the free R value. The result was a model that had the least bias without over-fitting free parameters (30,31).

An initial rigid body refinement was followed by repetitive rounds of isotropic variable sigma B-factor and positional refinement, until the free R factor (32) no longer decreased (The PMB software suite is available from the author M.A.W. (www.xray.utmb.edu/PMB)). The model was rebuilt in iterative rounds of model building (Xtalview (33)) and refinement. Structure factors were corrected for anisotropic scattering and absorption using a local scaling algorithm (28,34,35). The DCEG (FIG. 2A) inhibitor was modeled using Insight II (Accelrys, San Diego, Calif.) and energy minimized using the PRODRG web server (36), which also generated the stereochemical restraints used in the structure refinement.

The second P2$_1$ crystal structure was solved using the partially refined 2.6 Å model. The initial rigid body refinement was followed by repetitive rounds of individual atomic isotropic variable sigma B-factor and positional refinement, until the free R factor no longer decreased. Model building included the examination of waters selected by CNS. Waters with excessive B-factors (>60 Å$^2$) or poor density correlation were deleted.

Model quality was assessed after each refinement step with XtalView or PROCHECK (37). Refinement of the final model proceeded in parallel with alternate conformations of the DCEG ligand. The model with the lowest free R was chosen as the final model. The DCEG ligand of this model produced the best fit to the electron density from the two separate refinements. Multiple conformation refinement of DCEG in REFMAC (38, 39), including TLS anisotropic B-factors, with a single AR model and the two DCEG models confirmed that the chosen conformation had the highest correlation with the observations. All molecular figures were generated using PYMOL (40).

Overall Structure

Figure 1A:
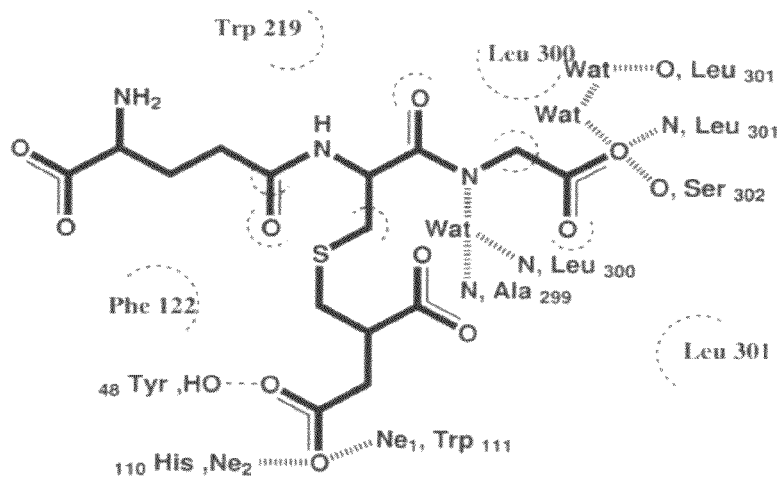
FIGS. 1A-1B depict the structure of DCEG and human aldose reductase.
Figure 2A:
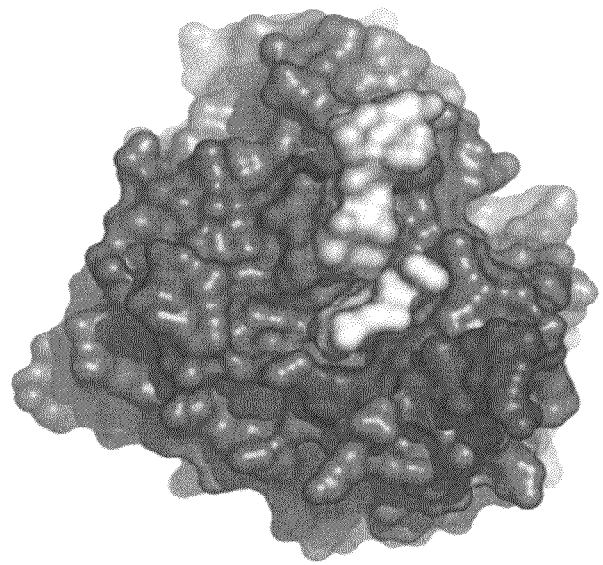
FIGS. 2A-2B depict the human aldose reductase active site with DCEG bound.
Figure 2B:
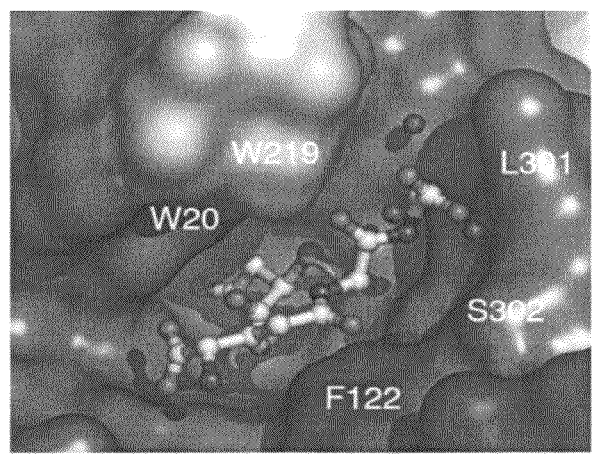

The AR:NADPH:DCEG ternary complex structure was refined to 1.94 Å resolution with a final R-factor of 21.6%. This structure showed well-defined electron density for the DCEG substrate at the "top" of aldose reductase active site pocket (FIG. 2B). The DCEG was bound between two opposing surfaces of the active site pocket, but did not completely fill the active site cleft (FIG. 1A). The DCEG substrate made ~80 contacts, defined as inter-residue distances ≤4 Å, with residues in the active site cleft (FIG. 1A). The majority of these intermolecular contacts were hydrophobic. The NADPH binding site was located at the base of the aldose reductase hydrophobic active site pocket and the NADPH cofactor was bound to the ternary complex in an orientation identical to that observed in previously reported crystal structures (3, 41, 42).

Figure 1B:
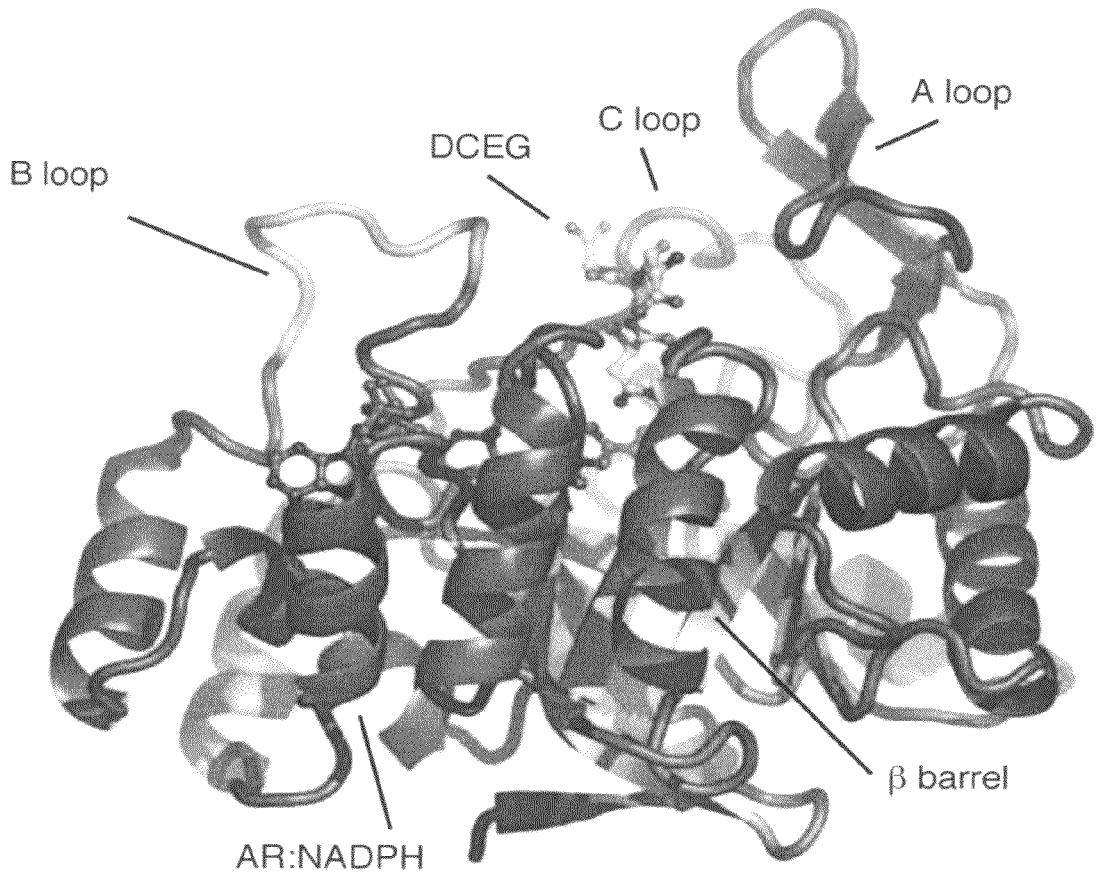

The active site of aldose reductase sat at the base of a deep cleft or binding pocket. The sides of the active site pocket were formed by three flexible loops A, B, and C (43) which sat on top of the aldose reductase $(\alpha/\beta)_8$ barrel (FIG. 1B). The active site comprises residues Tyr-48, His-110, and Trp-111. DCEG was bound in the active site almost filling the active site pocket. Trp-219 forms one side of the narrow pocket holding the inhibitor DCEG (FIG. 2B). The other residues lining this pocket included Trp-20, Trp-79, Trp-111, Phe-122, NADPH, Val-47, Cys-298, Ala-299, Leu-300, and Leu-301.

DCEG Interactions with AR

The C-terminal glycine moiety of DCEG was extensively hydrogen bonded to the backbone atoms of residues 300-302 in the flexible human aldose reductase C-terminal loop (loop-C). In addition, the ligand made several van der Waals contacts with aldose reductase. Several bound water molecules mediated the interaction between the DCEG glycine moiety and aldose reductase. The amides of Ala-299 and Leu-300 were bound indirectly to DCEG through a water molecule. The terminal carboxylate group of the DCEG interacted with the backbone of Leu-301 and Ser-302 and indirectly with Leu-301 through a network of waters (FIG. 2A). These residues were in human aldose reductase loop C which has been shown to be important for enzymatic activity. Mutations within this loop result in drastically lowered human aldose reductase activity (44).

The dicarboxyethyl group of DCEG was anchored in the conserved anion-binding site between the nicotinamide ring of the NADPH cofactor and aldose reductase residues Tyr-48, His-110, and Trp-111 similar to other known aldose reductase inhibitors (41,42). The terminal carboxylates of the dicarboxyethyl conjugate's longer arm, Oi2 and Oj2, were hydrogen bonded to active site residues His-110, Tyr-48, and Trp-111 (FIGS. 1A, 2B). The γ-glutamate of DCEG was observed to interact with the AR enzyme only through van der Waals contacts with Phe-122 that formed one side of the hydrophobic active site pocket. The lack of hydrogen bonds or extensive contacts permitted the γ-glutamate moiety significant conformational freedom.

The higher temperature factors for these atoms reflected the relative disorder in the N-terminal end of DCEG. The hydrophobic walls of the upper portion of the aldose reductase active site pocket were formed in large part by Trp-219 and Phe-122, similar to the structures observed in other AR:inhibitor complexes (41,42). These two aromatic residues tightly constrained the position of the cysteine moiety in DCEG. The Phe-122 and Trp-219 side chains could move slightly to accommodate differently sized inhibitors. The extensive van der Waals contacts with Trp-20 observed in the aromatic inhibitors tolrestat, zopolrestat, and sorbinil were completely absent in DCEG. The Trp-20 and Trp-79 residues, although still defining the active site pocket, did not interact with DCEG directly. They did, however, limit the conformational space available to the DCEG molecule.

The conformation of the glutathione (GS)-moiety of the AR-bound DCEG (FIG. 2B) was similar to the conformation of GS observed in the GS-binding proteins glutathione-S-transferase (45), sphingomonad GST (1fe2 (46)), human thioltransferase (47), yeast prion URE2P (48), and the chloride intercellular channel (49). The GS backbone conformation of DCEG was most distinct from the conformation of GS bound to glutatione reductase (1b4q (47), igra (50)). The GS conformation of AR-bound DCEG adopted the low energy Y-shape, rather than the V-form of GS observed in glutaredoxin (47), glutathione reductase (47, 50), and glutathione peroxidase (51,52) complexes.

The GS backbone of DCEG overlapped with the GS structures with root mean square deviations (rmsd) from 0.4 to 1.4 Å. The largest rmsd between the observed structures of GS bound to several different enzymes and DCEG bound to aldose reductase occurred in the N- and C-terminal atoms. In comparison with GS bound to glutathione reductase, the cysteine of DCEG bound to aldose reductase had a y angle that was rotated by ~180 degrees. The aldose reductase-bound DCEG glutathione backbone conformation was most similar to that observed in GS complexes with hematopoietic prostaglandin d synthase (53) or yeast prion URE2P (48).

DCEG binding to aldose reductase lacks the N-terminal hydrogen bonds seen in the other GS:protein complexes. The placement of the GS backbone was largely determined by the interaction of the conjugate with the active site of the enzyme and the mobile loop-C. The van der Waals interactions with the binding cleft were nonspecific and allowed for flexibility of the GS moiety.

Comparison with Other AR Structures

The structure of the human aldose reductase enzyme within the ternary complex showed significant conformational differences relative to the AR:NADPH binary complex (3). The backbone atoms of Pro-123 to Val-131 in loop A and Pro-218 to Pro-225 in loop B, which flank the active site pocket, were reoriented >5 Å upon DCEG binding relative to the binary structure. The AR:NADPH:DCEG ternary complex more closely resembled the AR:NADP:zopolrestat (54) and AR:NADP:Idd384 (41) ternary complexes than the AR:NADPH binary complex. In the ternary complexes the largest relative atomic movements, with rmsd>1 Å, occurred in the region of Ser-127, Pro-222, and Leu-300.

The conformation of loop B, residues Pro-218 to Pro-225, was very similar in all of the AR structures, with just the backbone conformation of residues Pro-222 and Asp-224 flipping in the holoenzyme. Loop A of the holoenzyme structure (3) displayed a completely different conformation for this entire loop region relative to the current complex. Loop C was observed in two different conformations, which depended on the size and shape of the inhibitor bound in the solved AR structures. The conformation of loop C in AR:NADPH:DCEG had the greatest similarity to the human aldose reductase structures found in the AR:NADPH holoenzyme (3) and AR:NADPH:Idd384 ternary complex (41). Additionally, loop C in the current structure had large positional differences with the conformation observed in the zoplorestat and tolrestat ternary complexes (42). This indicated that loop C was dynamic and could move to accommodate larger molecules such as zopolrestat and tolrestat. The smaller sorbinil inhibitor did not change this loop's conformation significantly (42).

Comparison with Molecular Dynamics Models

Based on molecular dynamics (MD) simulations on a GS-propanal conjugate binding to human aldose reductase (19), two possible alternate conformations of the bound substrate were proposed. The observed structure of DCEG in the AR:NADPH:DCEG ternary complex was very similar to the first, lowest energy model (Model 1) of our molecular dynamics simulation, i.e., 0.8 Å overall rmsd on the GS-backbone and 0.5 Å rmsd, excluding the disordered N-terminus of the substrate. The small variations between the model and DCEG structure could be attributed to the change in the active-site atoms from carbonyl in GS-propanal to a carboxylate in DCEG, and the conformational freedom of the γ-glu N-terminus.

It has been demonstrated that DCEG is a competitive inhibitor of aldehyde reduction by aldose reductase, indicating that the conjugate bound selectively to AR:NADPH and had little or no affinity for the enzyme of the AR:NADP$^+$ binary complex. The reasons for this behavior are apparent from the current structure. The non-specific interactions of DCEG with the active site cleft and loose shape complimentarily are consistent with a very low affinity of DCEG for apo AR.

The result of NADPH binding is rearrangement of the active site residues Tyr-48, His-110 and Trp-111, plus the adjacent A, B, and C loops. Thus, NADPH binding reorients these regions to form the active site pocket. It is only after these rearrangements that AR would have any significant affinity for DCEG. Therefore, DCEG binding must be preceded by formation of the holoenzyme AR:NADPH complex.

In the AR:NADPH:DCEG ternary complex, a larger percentage, i.e., 50%, of DCEG is buried by AR side chains than has been observed in structures of other GS-binding proteins (40-45%), suggesting that the strongly aliphatic nature of DCEG, which allows multiple contacts at the active site, was essential for competitive inhibition of aldehyde reduction. This was due to selective binding to the AR:NADPH binary complex. In contrast, more aromatic inhibitors, which bind to the aldose reductase active site primarily via hydrophobic interactions, bind with greater affinity to the AR:NADP+ binary complex and thus behave as non-competitive inhibitors of aldehyde reduction, but competitive inhibitors of alcohol oxidation (19).

DCEG-based Inhibitor Design

Figure 3:
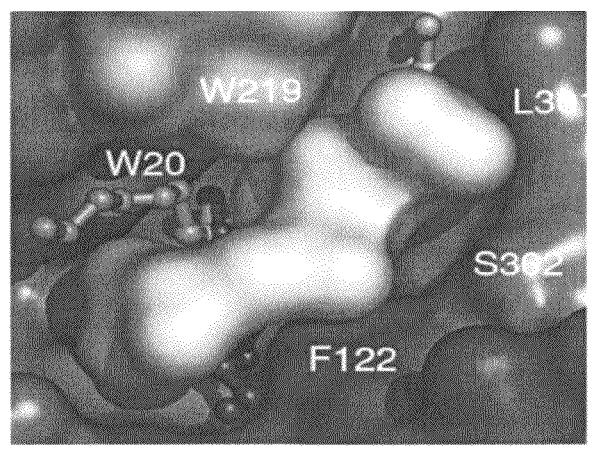
FIG. 3 is a model of a potential GS-like inhibitor with an aldehyde bound in the active site. An aldehyde chain (gold, green, or blue) may pass though one of three channels between the inhibitor (yellow) and protein (purple) to reach the AR active site. The mobile loops A, B, and C are colored as in FIGS. 1B and 2.

The structure of DCEG bound to aldose reductase provides a starting model for the design of an inhibitor of aldose reductase carbonyl metabolism which would not significantly interfere with aldose reductase detoxification of reactive aldehydes. The proposed GS-based inhibitor binding in the DCEG site would permit long alkyl chain peptides to reach the active site. Modeling of a DCEG-like selective inhibitor, based on our AR:NADPH:DCEG structure with an alkyl chain bound in the active site showed that there was more than one possible path for the alkyl chain to reach the active site (FIG. 3). Therefore, a DCEG-like inhibitor, lacking the active-site binding dicarboxyethyl moiety, could potentially block the binding of glucose and GS-conjugates while still permitting the entry and reduction of small to medium chain aliphatic aldehydes. By using such inhibitors, it might be possible to prevent the reduction of glucose to sorbitol in diabetics, conserve NADPH that can be used for the reduction of lipid peroxides and aldehydes, and regulate signaling pathways initiated by cytokines, chemokines, hyperglycemia, etc. without affecting the detoxification properties of AR that may be essential for reducing lipid aldehydes. Thus, a DCEG-based inhibitor might provide a therapeutic tool for regulating cytotoxic signals without inhibiting the detoxification role of aldose reductase.

EXAMPLE 2

Aldose Reductase Inhibition

McCoy's 5A medium, Dulbecco's modified Eagle's medium (DMEM), phosphate-buffered saline (PBS), penicillin/streptomycin solution, trypsin, and fetal bovine serum (FBS) were purchased from Invitrogen. Antibodies against Cox-1, Cox-2 and phospho PKC-b2 were obtained from Santa Cruz Biotechnology, Inc. (Santa Cruz, Calif.). Sorbinil and tolrestat were gifts from Pfizer and American Home Products, respectively. Mouse anti-rabbit glyceraldehyde-3-phosphate dehydrogenase antibodies were obtained from Research Diagnostics Inc.

Cyclooxygenase (Cox) activity assay and prostaglandin E2 (PGE2) assay kits were obtained from Cayman Chemical Company (Ann Arbor, Mich.). Platelet-derived growth factor (PDGF), basic fibroblast growth factor (BFGF), 3-(4,5-dimethylthiazol-2-yl)-2,5-diphenyltetrazolium bromide (MTT), and other reagents used in the Electrophoretic Mobility Shift Assay (EMSA) and Western blot analysis were obtained from Sigma. AR-siRNA (5'-AATCGGTGTCTCCAACTTCAA-3'; SEQ ID NO: 1) or scrambled siRNA (control) (5'-AAAATCTCCCTAAATCATACA-3'; SEQ ID NO: 2) were synthesized by Dharmacon Research. All other reagents used were of analytical grade.

Cell Culture

Human colon cancer cell lines, HCT-116 and Caco-2 were obtained from American type culture collection (ATCC). HCT-116 cells were maintained and grown in McCoy's 5A medium supplemented with 10% FBS and 1% penicillin/streptomycin and Caco-2 cells were grown in DMEM with 10% FBS and 1% penicillin/streptomycin at 37° C. in a humidified atmosphere of 5% $CO_2$. Human colon adenocarcinoma (SW480) cells were purchased from ATCC and cultured at 37° C. in a humidified atmosphere of 5% $CO_2$ in RPMI-1640 medium supplemented with 10% (v/v) heat-inactivated FBS, 1% (v/v) P/S solution, 2 mM L-glutamine, 10 mM HEPES, 1 mM sodium pyruvate, 4.5 g/L glucose, and 1.5 g/L sodium bicarbonate.

Measurement of Cytotoxicity

Caco-2 cells were grown to confluence in DMEM medium harvested by trypsinization and plated ~2500 cells/well in a 96-well plate. Subconfluent cells were growth-arrested in 0.1% FBS. After 24 h, 10 ng/ml of BFGF or PDGF without or with AR inhibitors sorbinil or tolrestat were added to the media and the cells were incubated for another 24 h. Cells incubated with the AR inhibitors alone served as control. Cell viability was determined by cell count and MTT-assay as described earlier (15, 55-56).

HT29 cells were grown to confluence in McCoy's medium and harvested and plated 2,500 per well in a 96-well plate. Subconfluent cells were growth arrested in 0.1% FBS with or without AR inhibitor sorbinil or zopolrestat (20 μM). After 24 hours, EGF (5 ng/ml) or BFGF (10 ng/ml) was added to the medium and the cells were incubated for another 24 hours. Cells incubated with the AR inhibitors alone served as control. Cell viability was determined by an MTT assay.

A549 cells were grown to confluence in Ham's F12K medium containing 10% FBS and harvested, and plated at 5000 cells per well in a 96-well plate. After 24 hrs A549 cells were treated with or without AR inhibitor sorbinil or tolrestat with various concentrations for another 24 hrs. Cells incubated without AR inhibitors served as control. Cell viability was determined by and MTT assay.

Determination of PKC Activity

PKC activity was measured using the Promega-Sigma TECT PKC assay system as described earlier (15). Briefly, aliquots of the reaction mixture (25 mM Tris-Hcl pH 7.5, 1.6 mg/mL phosphatidylserine, 0.16 mg/mL diacylglycerol, and 50 mM $MgCl_2$) were mixed with $[7-^{32}P]ATP$ (3,000 Ci/mmol, 10 μCi/μL) and incubated at 30° C. for 10 min. To stop the reaction, 7.5 M guanidine hydrochloride were added and the phosphorylated peptide was separated on binding paper. The extent of phosphorylation was detected by measuring radioactivity retained on the paper.

PGE2 Assay

Caco-2 cells were plated in 6 well plates at a density of $2 \times 10^5$ cells/well. After 24 hours, the medium was replaced with fresh medium containing 0.1% serum with or without, sorbinil (20 μM) followed by treatment with either 10 ng/ml BFGF or PDGF, for another 24 h. HT29 cells were plated in 6 well plate at a density of $2 \times 10^5$ cells/well. After 24 hours, medium was replaced with serum-free medium with or without, sorbinil or zopolrestat (20 μM) followed by treatment with either EGF (5 ng/ml) or BFGF (10 ng/ml) for another 24 h. The medium from each cell lines was collected from each well and analyzed for PGE2 by using an Enzyme Immuno Assay kit according to the manufacturer's instructions (Cayman Chemical Co., Inc.).

Briefly, 50 μl of diluted standard/sample were pipetted into a pre-coated goat polyclonal anti-mouse IgG 96-well plate. Aliquots (50 μl) of a PGE2 monoclonal antibody and PGE2 acetylcholine esterase (AchE) conjugate, (PGE2 tracer) were added to each well and allowed to incubate at 4° C. for 24 h. After incubation, the wells were washed five times with wash buffer containing 0.05% Tween-20, followed by the addition of 200 μl of Ellman's reagent containing acetylthiocholine and 5,5'-dithio-bis-(2-nitrobenzoic acid). Samples were read after 60 min at 412 nm with an ELISA reader. In this procedure the intensity of yellow color, is proportional to the amount of PGE2 tracer bound to the well and is inversely proportional to the amount of free PGE2 present in the well during incubation.

Cyclooxygenase Activity Assay

For determination of Cox activity growth-arrested Caco-2 cells were treated with either 10 ng/ml BFGF or PDGF in the absence and presence of sorbinil (20 mM) for 24 h. The cells were harvested and homogenized in cold (4° C.) buffer containing 0.1M Tris-Hcl, pH 7.8 and 1 mM EDTA and the activity was measured in 96 well plate according to the manufacturer's (Cayman Chemical Co., Inc.) instructions. Briefly, 10 μl of standard/sample were incubated in the presence of arachidonic acid and substrate, N,N, N,N-tetra methyl-p-phenylenediamine (TMPD) in a total reaction volume of 210 μl. The Cox peroxidase activity was measured colorimetrically by monitoring appearance of oxidized TMPD at 590 nm by using ELISA reader.

NF-kB-dependent reporter Secretory Alkaline Phosphatase (SEAP) Expression Assay.

Caco-2 cells ($1.5 \times 10^5$ cells/well) were plated in six-well plates and after attachment overnight, were serum-starved in optiMEM medium for 24 h with or without aldose reductase inhibitor, sorbinil (20 μM) and were transiently transfected with pNF-kB-SEAP construct or control plasmid pTAL- SEAP DNA (Clontech, USA) using the lipofectamine plus reagent. After 6 h of transfection, cells were treated either with 10 ng/ml BFGF or PDGF for 48 h in DMEM medium containing 0.1% FBS. The cell culture medium was then harvested and analyzed for SEAP activity, essentially as described by the manufacturer (Clontech Laboratories, Palo Alto, Calif.), using a 96-well chemiluminescence plate reader and Kodak Image Station 2000R.

Determination of NF-kB Activation

The cytosolic as well as nuclear extracts were prepared as described earlier (15) and the NF-kB activity was determined by using the colorimetric non-radioactive NF-kB p65 Transcription Factor Assay kit (Chemicon Intl.) as per the supplier's instructions. Briefly, a double stranded biotinylated oligonucleotide containing the consensus sequence for NF-kB binding (5'-GGGACTTTCC-3'; SEQ ID NO: 3) was mixed with nuclear extract and assay buffer. After incubation, the mixture (probe+extract+buffer) was transferred to the streptavidin-coated ELISA kit and read at 450 nm using an ELISA plate reader. For each experiment, triplicate samples were measured for statistical significance.

RT-PCR

Total RNA was isolated from Caco-2 cells by using Rnaeasy micro isolation kit (Qiagen). Total RNA (1.5 µg) sample was reverse transcribed with Omniscript and Sensiscript reverse transcriptase one-Step RT PCR system with HotStar-Taq DNA polymerase (Qiagen) at 55° C. for 30 min followed by PCR amplification. The oligonucleotide primer sequences were as follows: 5'-AAACCCACTCCAAACACAG-3' (sense; SEQ ID NO: 4) and 5'-TCATCAGGCACAGGAG-GAAG-3' (antisense; SEQ ID NO: 5) for Cox-2, and 5'-TGAGACCTTCAACACCCCAG-3' (SEQ ID NO: 6) and 5'-TTCATGAGGTAGTCTGTCAGGTCC-3' (SEQ ID NO: 7) for β-actin. PCR reaction was carried out in a GeneAmp 2700 thermocycler (Applied Biosystems, Foster City, Calif.) under the following conditions: initial denaturation at 95° C. for 15 min; 35 cycles of 94° C. 30 s, 62° C. 30 s, 72° C. 1 min, and then 72° C. 5 min for final extension (57). PCR products were electrophoresed in 2% Agarose-1™ TAE gels containing 0.5 µg/ml ethidium bromide.

Flowcytometric Analysis of Cell Cycle

The Caco-2 and A549 cells were grown separately in 6 well plates at a density of approximately $1.5 \times 10^5$ cells/well. Growth-arrested Caco-2 cells were pre-incubated with or without sorbinil 20 µM or carrier for 24 h and then stimulated with either 10 ng/ml BFGF or PDGF for another 24 h. After 24 hrs A549 cells were incubated with or without sorbinil at different concentrations for another 24 h.

The Caco-2 and A549 cells were then washed with PBS and harvested by trypsinization. Cellular DNA was stained with low and high salt solutions. Briefly, cells were resuspended in 250 µl of solution A, low salt stain, containing polytheleneglycol (30 mg/ml), propidium iodide (0.05 mg/ml), triton-x-100 (1 µl/ml), sodium citrate 4 mM, RNAse A 10 µg/ml and incubated at 37° C. for 20 min followed by the addition of 250 µl of solution B, high salt stain containing 400 mM NaCl instead of 4 mM sodium citrate in solution A, and incubated overnight at 4° C. Cell cycle analysis was performed with a minimum of 10,000 events per analysis by using FACScan flow cytometer (Becton, Dickinson and Co., San Jose, Calif., USA).

Measurement of Reactive Oxygen Species

Caco-2 cells were plated in a 24-well plate at a density of $1.5 \times 10^4$ cells/well in DMEM and then serum-starved at 60-70% confluence in the absence and presence of 20 µM sorbinil or tolrestat for overnight in phenol red-free DMEM supplemented with 0.1% FBS. Cells were then pre-incubated for 30 min with the ROS-sensitive fluorophore 2',7'-dichlorofluorescein diacetate (DCFH-DA), which is taken up and oxidized to the fluorescent dichlorofluorescein by intracellular ROS. After incubation with DCFH-DA, the cells were exposed to FGF or PDGF 10 ng/ml for 60 min and fluorescence was measured with a CytoFluorII fluorescence plate reader (PerSeptive Biosystems, Inc., Framingham, Mass.) at excitation of 485 nm and emission of 528 nm.

The levels of ROS in sections of A549 xenografts was determined using dihydroethidium (Het; Molecular Probes, Eugene, Oreg.). The Het dye gives red fluorescence when oxidized to EtBr in the presence of ROS such as $O_2$. Serial sections (5 µM) of para-formaldehyde fixed xenografts were deparafinized and rehydrated and incubated with Het dye (5 µM in PBS) for 30 min at 37° C. followed by acquisition of images using a fluorescence microscope 200× magnification.

Preparation of GS-aldehyde Esters

HNE was synthesized as described previously (14). The glutathione monoethyl-ester (GS-ester) obtained from Sigma was purified by HPLC using a reverse phase column (14) and the conjugate of GS-ester and HNE was made by incubating 1 µmol of $[4-^3H]$-HNE with 3-fold excess of GS-ester and 0.1 M potassium phosphate, pH 7.0, at 37° C. The reaction was followed by monitoring absorbance at 224 nm. Approximately 90% of HNE was conjugated with GSH over a period of 60 min. The GS-HNE-ester thus formed was purified by HPLC (14) and its concentration was calculated on the basis of radioactivity. For synthesis of GS-DHN-ester, 1 µmol of GS-HNE-ester was incubated with 1 unit of recombinant human AR and 0.1 mM NADPH in 0.1 M potassium phosphate, pH 7.0, at 37° C. The reaction was followed by monitoring the decrease in absorbance at 340 nm. More than 85% of the conjugate was reduced in 30 min. The enzyme was removed by ultrafiltration using an Amicon Centriprep-10, and GS-DHN-ester in the filtrate was purified on HPLC and confirmed by ESI/MS.

Antisense Ablation of AR

Caco-2 cells were grown to 50-60% confluence in DMEM supplemented with 10% FBS and washed four times with Opti-MEM, 60 min before the transfection with oligonucleotides (15). The cells were incubated with 2 µM AR antisense or scrambled control oligonucleotides using LipofectAMINE Plus (15 µg/ml) as the transfection reagent as suggested by the supplier. After 12 h, the medium was replaced with fresh DMEM (containing 10% FBS) for another 12 h followed by 24 h of incubation in serum-free DMEM (0.1% FBS) before growth factor stimulation. Changes in the expression of AR were estimated by Western blot analysis using anti-AR antibodies.

Cell Invasion Assay

HT29 cells were serum starved in McCoy's medium with or without sorbinil for 24 hrs. HT29 cells and A549 cells each were plated $0.8 \times 10^5$ cells per well in a 96 well plate containing culture inserts of an 8.0-µm polycarbonate membrane which is coated with a thin layer of ECMatrix. HT29 cells then were treated with 5% FBS or EGF (5 ng/ml) with or without sorbinil or zopolrestat (75 µM). A549 cells then were treated with 5% FBS in Ham's F12K medium with or without sorbinil or zopolrestat (100 µM). Both HT29 and A549 plates were transferred to a feeder tray with McCoy's medium (HT29) or Ham's F12K medium (A549) each containing 5% FBS. The HT29 and A549 cells were incubated at 37° C. under a 5% $CO_2$ atmosphere. After 24 hrs invaded cells at bottom of the culture inserts were rinsed with PBS and incubated for in a detachment solution for 30 min at 37° C. Then cells were incubated in lysis buffer/fluorescence dye for 15 min and fluorescence was read at 480/520 nm.

Azoxymethane-induced Colon Carcinogenesis and ACF Analysis

Approximately six weeks old mice were divided into 4 groups (5 mice/group). Mice in groups 3 and 4 were treated with azoxymethane in sterile saline, at a dose of 10 mg/kg body weight i.p. once a week, for 3 weeks. In group 4, mice were treated with AR inhibitor sorbinil (25 mg/kg body weight per day) for entire period after 1 week from the first azoxymethane injection. Mice in groups 1 and 2 received equal volumes of sterile saline and sorbinil, respectively. Similarly AR knock out mice also were treated with azoxymethane (10 mg/kg body weight i.p.) once a week for 3 weeks. After 9 weeks all mice were killed by $CO_2$ euthanasia. The colons were removed, flushed with saline and opened from anus to cecum and fixed flat between two pieces of filter paper in 10% buffered formalin for 24 h. Colons were stained with 0.2% methylene blue dissolved in saline and the numbers of aberrant crypts foci (ACF) were counted under a microscope at 200× magnification.

In Vivo Metastasis

For in vivo metastasis studies, 4- to 6-weeks-old male nude$^{nu/nu}$ mice were obtained from Harlan Sprague Dawley (Indianapolis, Ind.) and housed in clean, pathogen-free rooms in an environment with controlled temperature (22° C.), humidity and a 12 hours light/dark cycle. The mice were fed standard chow (Formula Chow 5008; Purina Mills, St. Louis, Mo.), given tap water ad libitum and were allowed to acclimate for 1 week. Metastatic HT29-GFP cells were injected intrasplenically by known methods.

Briefly, mice were anesthetized with halothane, a small left abdominal flank incision was created and the spleen was exteriorized. HT29-GFP cells were harvested using only trypsin and were resuspended as a single-cell suspension in Hanks Balanced Salt Solution, free of $Mg^{2+}$ and $Ca^{2+}$. HT29-GFP cells ($5 \times 10^6$ cells/400 µl) were injected into the spleen with a 27-gauge needle. The spleen was returned to the abdomen and the wound was closed in one layer with wound clips. After 24 hrs spleen was removed and animals were randomized into metastatic control and AR inhibitor, sorbinil group. Control group was fed with normal diet and AR inhibitor group fed with sorbinil (40 mg/kg body weight) in the diet. Mice were killed after 35 days, and metastasis in the liver was evaluated by using the Illumatool TLS (Lightools Research, Encinitas, Calif.).

Effect of AR Inhibition or Ablation on Tumor Growth in Nude Mice

Athymic nude nu/nu mice were obtained from Harlan (Indianapolis, Ind.). Nine mice (20 weeks old) were divided into three groups of three animals and were treated with PBS, scrambled AR siRNA, and AR-siRNA, respectively. All nine animals were injected with $2 \times 10^6$ A549 human lung carcinoma cell suspensions in 100 µl PBS s.c. Animals were examined daily for signs of tumor growth. Treatment was given two times (day 1 and day 14) when the tumor surface area approximately 45 mm$^2$ (day 25). Treatment consisted of 200 µg AR-siRNA in 100 µl PBS. Control groups were treated with 200 µg/100 µl scrambled siRNA or diluent (PBS) alone. For the determination of effect of AR inhibitor, animals were fed with zopolrestat (40 mg/kg body weight) in the diet. Tumors were measured in two dimensions using calipers.

Measurement of AR Expression in Sections of Tumor Xenografts

Serial sections (5 µM) of para-formaldehyde fixed xenografts were deparafenized and rehydrated and incubated with peptide specific AR antibodies and developed using DakoCytomation LSAB+System-HRP kit. The intensity of staining was observed under light microscope with 200× magnification.

Western Blot Analysis

To examine expression of any of Cox-1, Cox-2, phospho-PKC-2, GAPDH, E2F1, Cyclin D1, Cyclin E, and iNOS proteins, Western blot analyses were carried by known methods (15). Equal amounts of protein from cell extracts were subjected to 12% SDS-PAGE followed by transfer of proteins to nitrocellulose filters, probing with the indicated antibodies, and the antigen-antibody complex was detected by enhanced chemiluminescence (Pierce, Piscataway, N.J., USA).

Data are presented as mean±SE and P values were determined by unpaired Student's t test. P values of <0.01 were considered significant.

EXAMPLE 3

Effect of AR Inhibition on TNF-a Generation in High Glucose

Figure 5A:
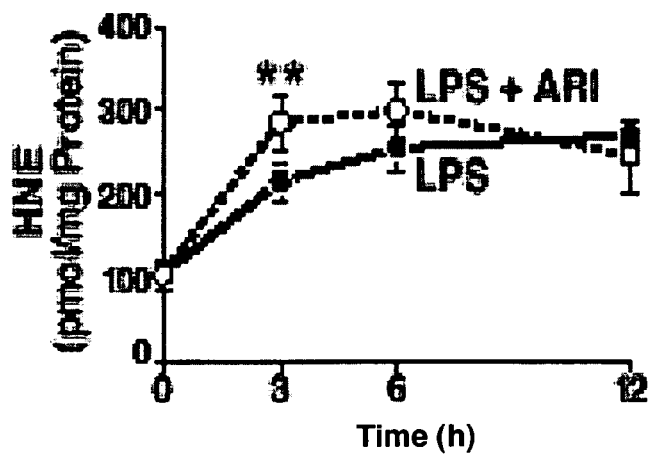
FIGS. 5A-5F illustrate the effect of AR inhibition/ablation on LPS- and lipid aldehyde-induced signaling in RAW264.7 cells. Cells were growth-arrested in Dulbecco's modified Eagle's medium containing 0.1% serum with or without sorbinil (10 mM) and challenged with LPS (1 mg/ml). At the indicated times, cells were harvested for measurement of HNE (FIG. 5A), protein-HNE adducts (FIG. 5B), NF-kB (FIG. 5C), and TNF-a and IL-6 (FIG. 5D) as described in the methods. Cells were growth arrested as described above or transfected with control or AR siRNA oligonucleotides, incubated with GS-HNE-ester, or GS-DHN-ester (1 mM), and harvested for determination of NF-kB (FIG. 5E), membrane-bound total PKC (FIG. 5F).

The effects of inhibiting PLC, NADPH oxidase and aldose reductase on the production of TNF-a in a culture medium (rat VSMC cells) are demonstrated. Growth-arrested VSMC in 5.5 mM glucose (NG) were preincubated for 1 h without or with apocyanin (25 mM), D609 (100 mM), calphostin C (0.2 mM), N-acetyl cysteine (10 mM) and NF-kB inhibitor (18 mM) respectively, followed by the addition of 19.5 mM glucose, after which the cells were incubated for 12 and 24 hrs. As shown in FIG. 5A, incubation with the PC-PLC inhibitor (calphostin C) markedly decreased TNF-a secretion. A similar decrease in TNF-a was observed in cells treated with the NADPH oxidase inhibitor apocyanin and the antioxidant N-acetylcysteine. Collectively, these observations support a mechanism in which high glucose increases TNF-a secretion by stimulating an intracellular signaling pathway that depends upon the activation of PLC and NADPH oxidase and the resultant change in the redox state of the cells.

Figure 4A:
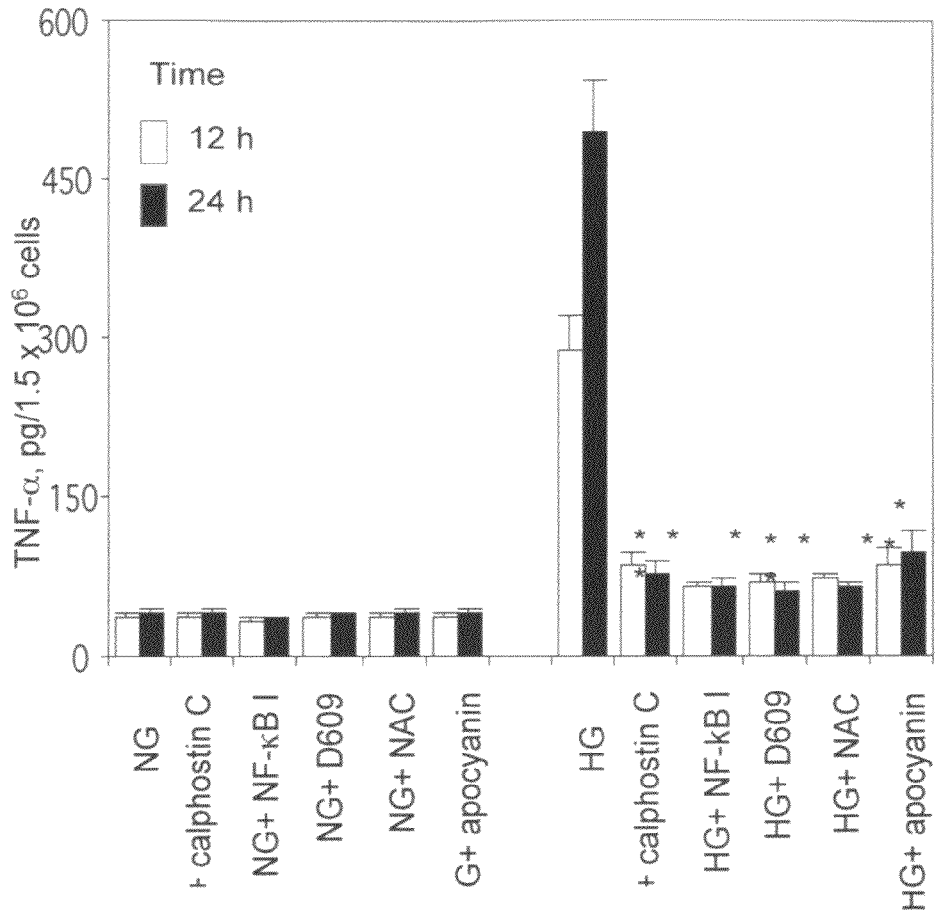
FIGS. 4A-4C illustrate the regulation of high glucose-induced TNF-a production by aldose reductase. Growth-arrested VSMC in 5.5 mM glucose (NG) were preincubated for 1 h without or with apocyanin (25 mM), D609 (100 mM), calphostin C (0.2 mM), N-acetyl cysteine (10 mM) and NF-kB inhibitor (18 mM) (FIG. 4A) and without or with sorbinil or tolrestat (10 mM each) (FIG. 4B) followed by the addition of glucose (19.5 mM) and incubation for the indicated times. AR antisense ablated VSMC were incubated with HG for the indicated times (FIG. 4C). The data represent mean±SEM (n=4). **P<0.001 versus cells incubated in high glucose.
Figure 4B:
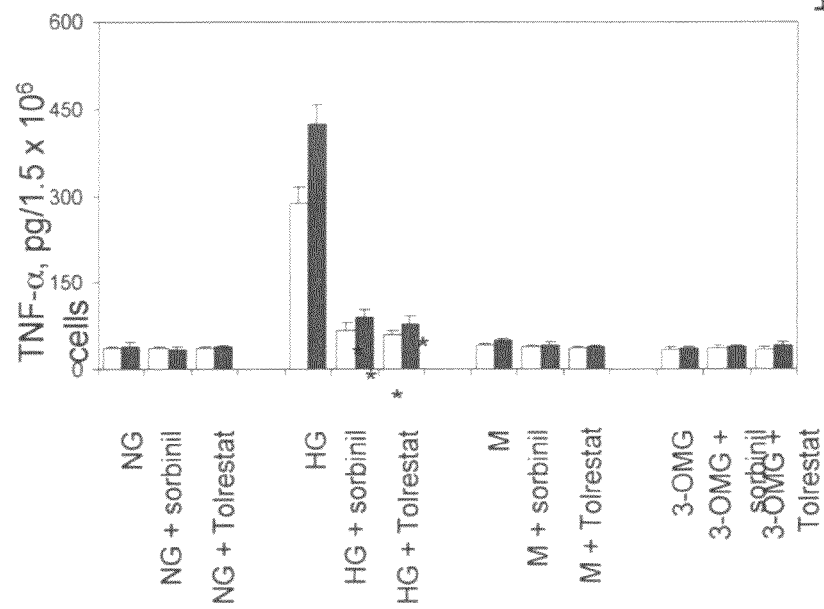
Figure 4C:
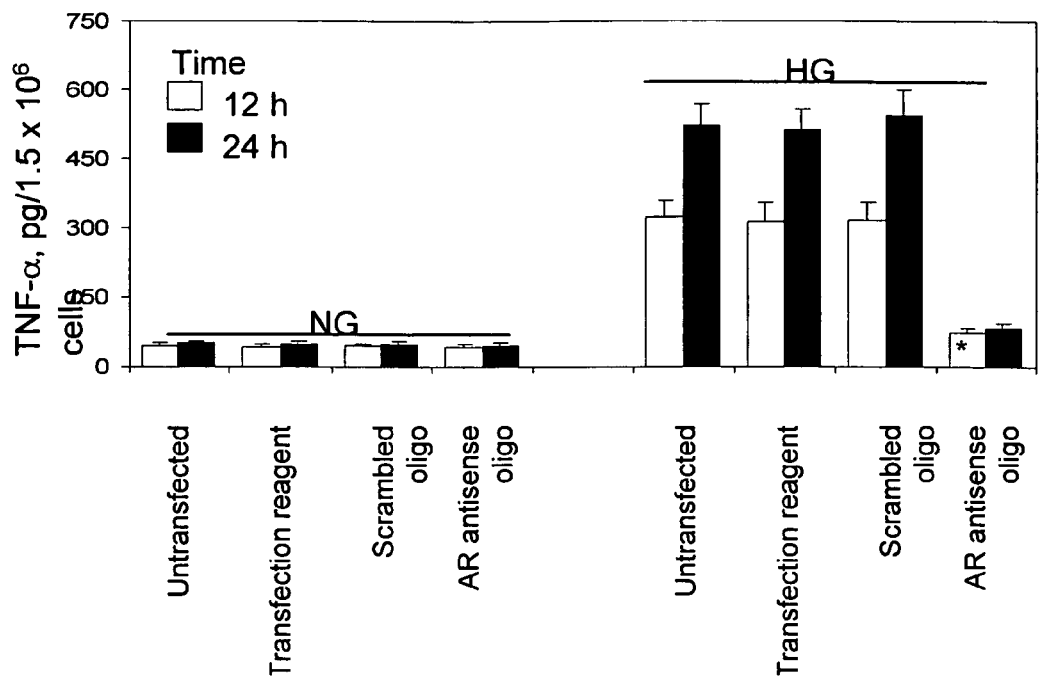

That this mechanism requires aldose reductase is suggested by data presented in FIGS. 4B-4C, which show that either pharmacological inhibition of AR by treating cells with AR inhibitors sorbinil or tolrestat or antisense ablation of the AR gene prevents high glucose-induced TNF-a secretion. Treatment with AR inhibitors did not affect basal levels of TNF-a in media containing 5.5 mM glucose, mannitol, or 3-OMG. Moreover, high glucose-induced TNF-a production was not prevented in untransfected cells or cells incubated with the transfection medium or transfection medium containing scrambled oligonucleotides. These observations attest to the specificity of TNF-a generation on AR activity. Taken together, the signaling studies described above suggest that high glucose increases TNF-a secretion, by increasing aldose reductase and phospholipase C. These processes stimulate PKC and then NF-κB, which in turn increases transcription of the TNF-a gene.

EXAMPLE 4

Effect of AR Inhibition on NF-κB Mediated Inflammatory Response Induced by Bacterial Infection NF-κB is a central transcriptional regulator of inflammatory mediators. Reactive oxygen species (ROS) can stimulate nuclear localization and activation of NF-κB however the exact mechanism is unknown. A model of NF-κB activation induced by bacterial infection was used to study how ROS might activate NF-κB.

Figure 5B:
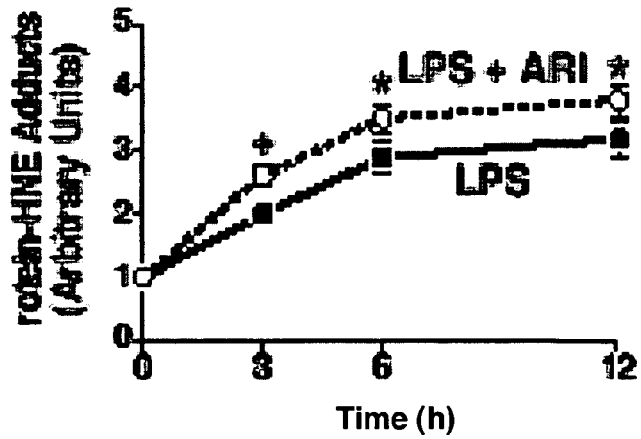
Figure 5C:
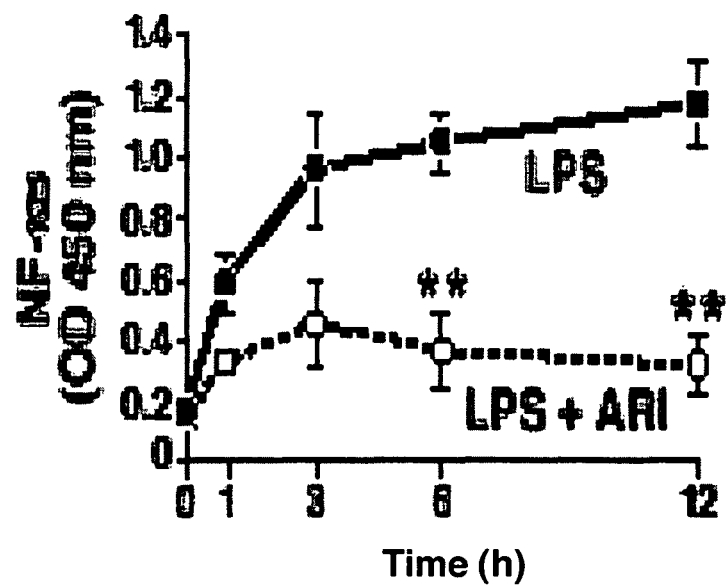
Figure 5D:
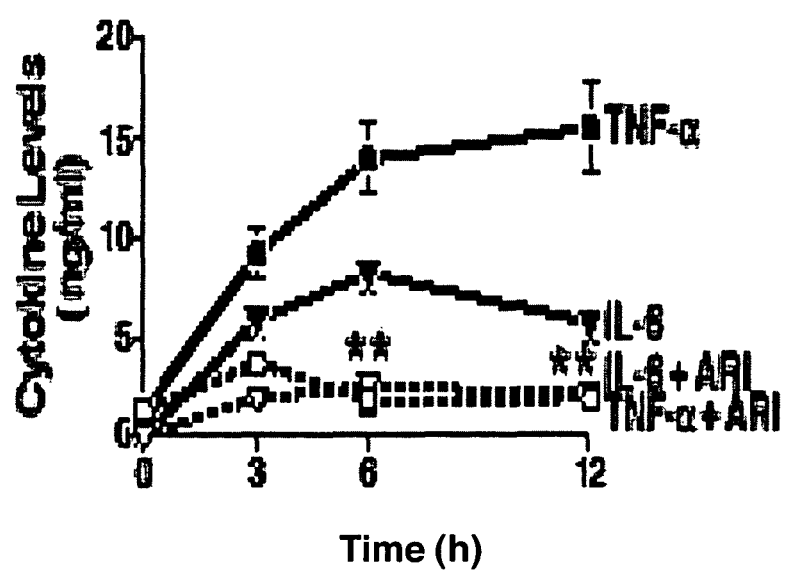
Figure 5E:
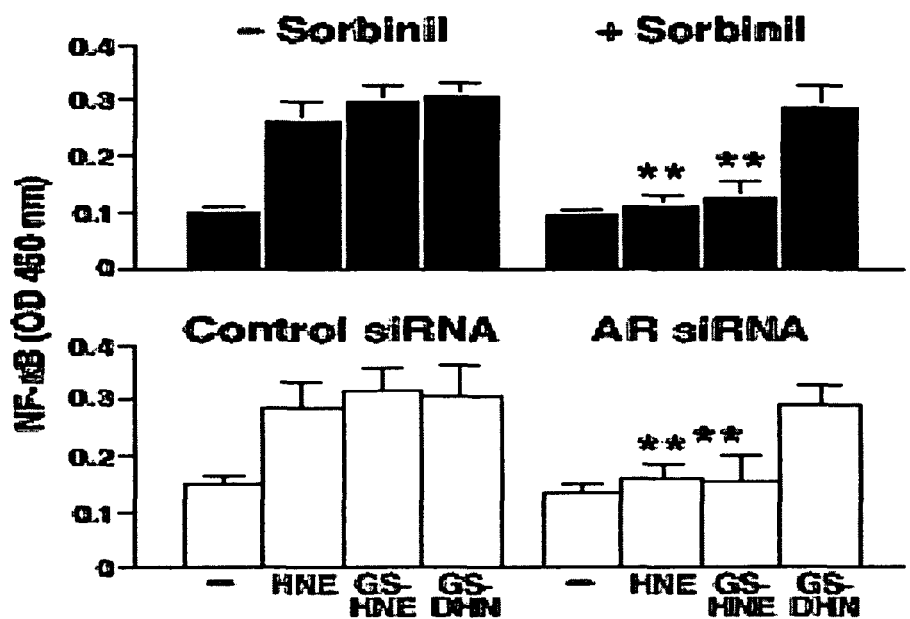

The effect of AR inhibition on 4-hydroxy-trans-2-nonenol (HNE) induction by bacterial lipopolysaccharide (LPS) was evaluated in RAW264.7 macrophages. LPS was found to increase HNE and protein-HNE adducts by nearly 3-fold within 6 h (FIGS. 5A-5B). When AR was pharmacologically inhibited with sorbinil, HNE and protein-HNE adduct levels increased, consistent with a role for AR in reducing HNE. Inhibition of AR significantly decreased LPS-induced NF-κB and cytokine activation (FIG. 5C-5D). In macrophage cells, treatment with HNE/Glutathione (GS)—HNE or glutathione conjugate of 1,4-dihydroxynonene (GS-DHN) resulted in phosphorylation of IKK-a/b and translocation of NF-κB to the nucleus (FIG. 5E). Inhibition of AR with sorbinil or small interfering RNA (siRNA) targeting AR mRNA significantly blunted the effects of HNE/GS-HNE on IKK-a/b phosphorylation and NF-kB translocation, but had no effect on the ability of GS-DHN, the already reduced form of GS-HNE, to activate NF-κB (FIG. 5E), suggesting that GS-DHN is sufficient for NF-κB translocation and is involved in IKK-a/b phosphorylation.

Figure 5F:
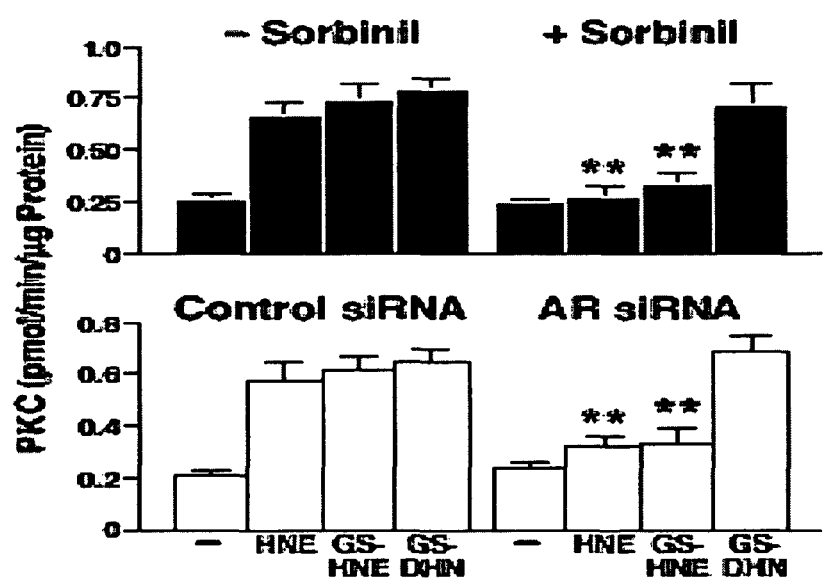

To determine if GS-DHN serves as a cellular sensor of ROS-induced insults, its effects on phosphorylation events upstream of IKK/NF-κB activation in RAW264.7 macrophages was examined. After GS-DHN challenge, the activity of protein kinase C(PKC), a kinase upstream of IKK increased by ~2.5 fold within 60 min (FIG. 5F). GS-DHN also induced phosphorylation of PLC-b3 and PLC-g1, which activate PKC but did not affect total PLC protein levels (not shown). HNE and GS-HNE had similar effects on the phosphorylation of the kinases upstream of NF-κB (FIG. 5F). However, pharmacologic inhibition of AR decreased the phosphorylation of PLC, PKC, and IKK induced by HNE and GS-HNE, but had no effect on GS-DHN-initiated phosphorylation of PLC and its downstream kinases (FIG. 5F). siRNA-mediated ablation of AR produced similar effects (FIG. 5F). These findings suggest that AR activity results in the production of reduced lipid aldehyde-glutathione conjugates that initiate an inflammatory cascade via PLC.

To investigate whether AR mediates the LPS signal in vivo, examined the effects of AR inhibition on NF-κB signaling pathways and myocardial dysfunction in a mouse model of overwhelming sepsis was examined. After pretreatment with sorbinil or vehicle alone, mice were injected peritoneally with a sub-lethal dose (4 mg/kg body wt) of LPS, and serum levels of inflammatory cytokines and chemokines were measured (FIGS. 6A-6B). In controls, TNF-a, IL-6, IL-12, and interferon-g levels increased 3- to 6-fold within 8 h after LPS exposure and began declining by 24 h but remained elevated. In sorbinil-treated mice, however, serum cytokine levels increased only 2-fold, began declining within 4 h, and returned to baseline levels within 12 h. Remarkably, treatment with sorbinil 2 h after LPS exposure also blunted the maladaptive systemic inflammatory response in serum. Similar effects of AR inhibitor on cytokine and chemokine activation within the myocardium after LPS challenge was also observed (FIGS. 6A, 6C).

Figure 7A:
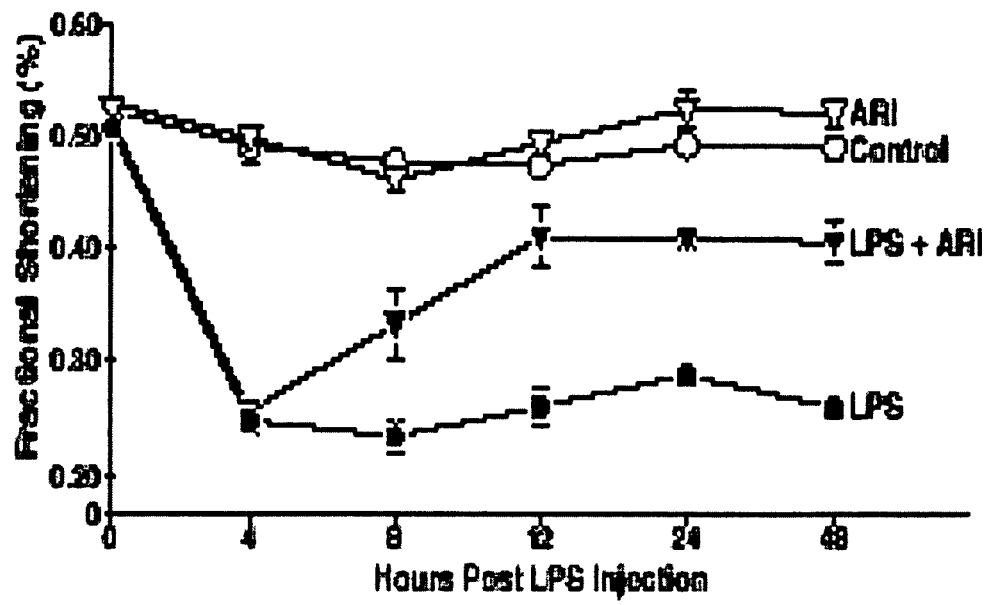
FIGS. 7A-7D illustrate the effect of AR inhibition on LPS-induced cardiac dysfunction. C57BL/6 mice (N=6 per group) were treated as described in FIG. 9, and fractional shortening percent (FS %) was determined by M-mode echocardiography 0-48 h after LPS injection (FIG. 7A). Values are means of SD. The data were analyzed by one-way repeated-measures ANOVA. Cardiac function in isolated mouse hearts (Langendorff preparation) was determined at various times after LPS challenge as a function of increasing Ca2+ concentration (FIG. 7B) or coronary flow rate (FIG. 7C). Values are means±SEM of six independent experiments.

To determine if AR inhibition could also rescue the cardiac dysfunction associated with the inflammatory response, serial echocardiography in LPS-challenged mice pretreated with sorbinil or vehicle and in unchallenged controls injected with vehicle or sorbinil was performed. In all LPS-challenged mice, percent fractional shortening (FS %) was depressed at 4 h after the injection; however, at 8 h, FS % had recovered significantly in the mice pretreated with sorbinil, but had deteriorated further in vehicle-injected controls (FIG. 7A). The functional recovery in the sorbinil group persisted at 12, 24, and 48 h, but FS % in the LPS challenged animals remained profoundly depressed. The FS % was not affected in unchallenged controls. Similar results were observed in mice given sorbinil 2 h after LPS challenge. The general activity level of LPS-exposed mice was consistent with the echocardiographic findings: sorbinil-treated mice exhibited normal grooming and other activities within 24 h, while LPS-treated mice remained inactive and huddled close to one another.

Figure 7B:
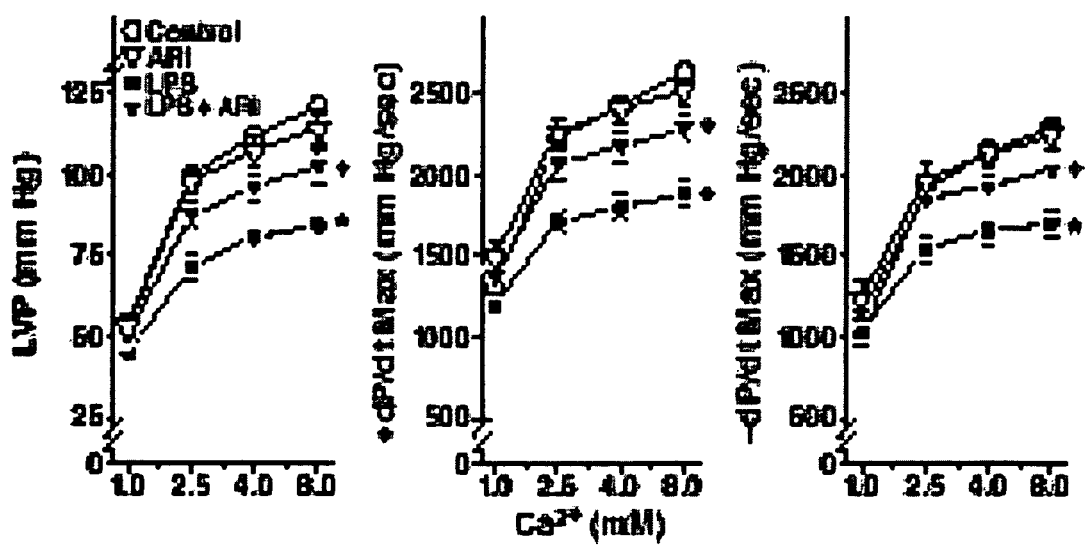
Figure 7C:
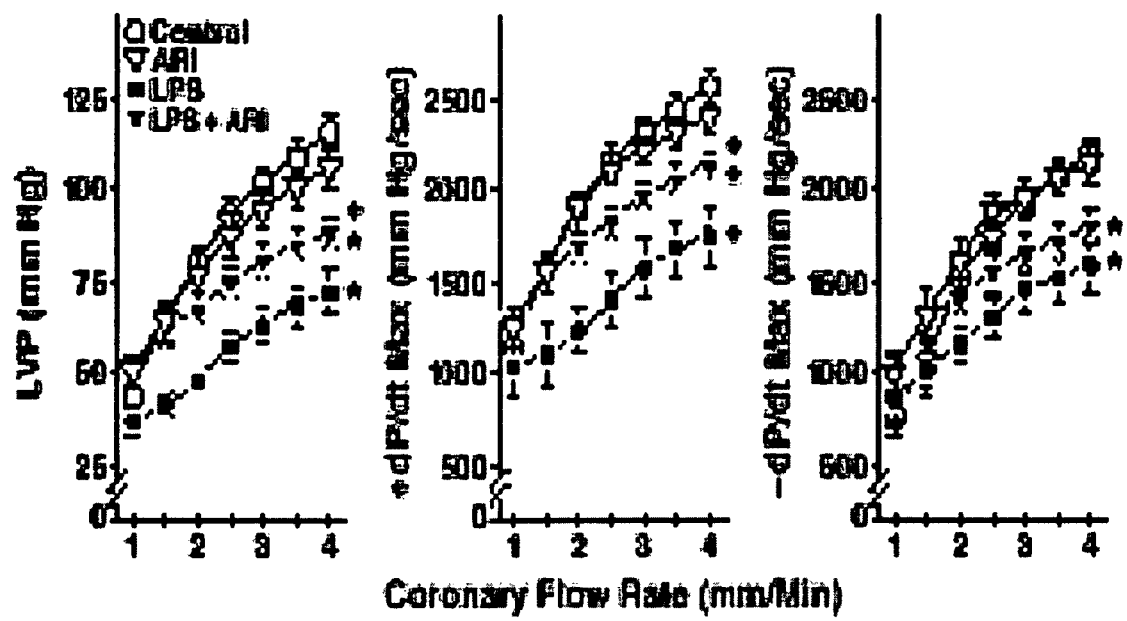

To more rigorously assess the effect of AR inhibition on cardiac function, spontaneously beating isolated mouse hearts (Langendorff preparation) were perfused with the AR inhibitor and challenged with LPS (FIGS. 7B-7C). In the presence of LPS, perfusion with sorbinil significantly increased left ventricular pressure (LVP), the velocity of ventricular contraction (+dP/dtmax), and the velocity of ventricular relaxation (−dP/dtmax) compared to vehicle; the time to maximal ±dP/dt, coronary perfusion pressure, coronary vascular resistance, and heart rate were unaffected. When calcium concentration or coronary flow rate was increased, the differences in sorbinil-treated mice were further magnified (FIGS. 7B-7C). These findings demonstrate that inhibition of AR activity rapidly improved the systolic and diastolic cardiac dysfunction induced by LPS.

Figure 7D:
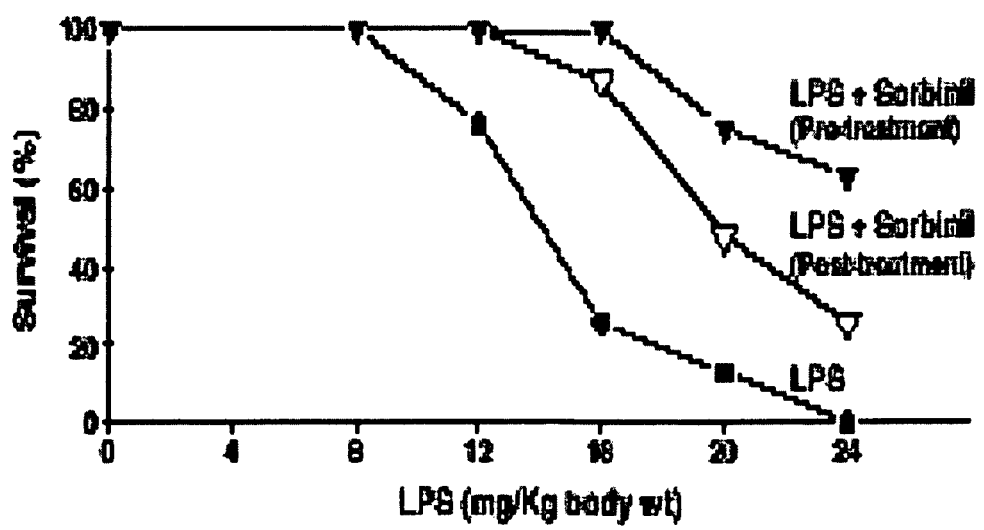

The above studies were performed with sublethal doses of LPS in order to assess effects on cardiac function. However, levels of LPS after bacterial sepsis often cause lethality in humans despite antibiotic therapy. Therefore increasing doses of LPS was administered to determine the dose at which fifty percent lethality occurred (LD50) in the presence or absence of aldose reductase inhibitor (ARI) in order to determine if ARI protected mice for LPS-induced death (FIG. 7D). It was found that the LD50 in control mice was 14 mg/kg LPS as previously reported. Remarkably, pre-treatment of mice with sorbinil resulted in approximately 90% survival at the same LPS dose and over 60% survival even with LPS doses as high as 24 mg/kg, which was a 100% lethal dose in controls by 48 hours. Administration of sorbinil two hours after LPS exposure, without pretreatment, still resulted in improved mortality compared to controls with an LD50 of 20 mg/kg (FIG. 7D). Thus, inhibition of AR prevented mortality associated with lethal doses of LPS.

Figure 8A:
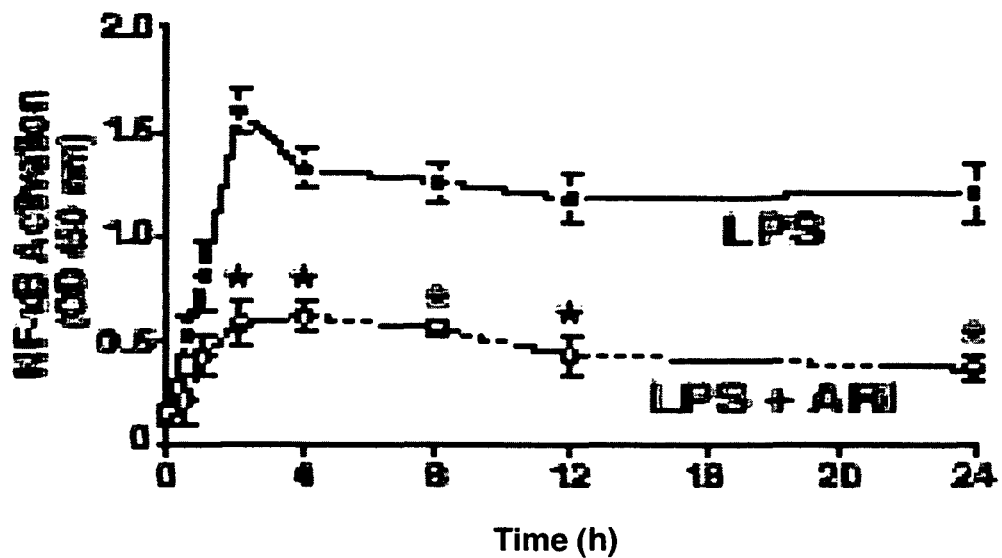
FIGS. 8A-8D illustrate the effect of AR inhibition on LPS signaling in the heart. C57BL/6 mice (N=6 per group) were treated as described in FIG. 6E. At the indicated times, NF-kB activation (FIG. 8A), AP1 activation with an electrophoretic mobility shift assay (FIG. 8B), iNOS expression by western blotting (FIG. 8C), or PKC activation with a total PKC assay system (FIG. 8D) (SignaTect, Promega), or phosphorylated forms of the indicated kinases by western blotting (FIG. 8E), was detected. Values are means±SEM (N=4). *$P<0.001$ versus LPS-treated mice. OD, optical density.
Figure 8B:
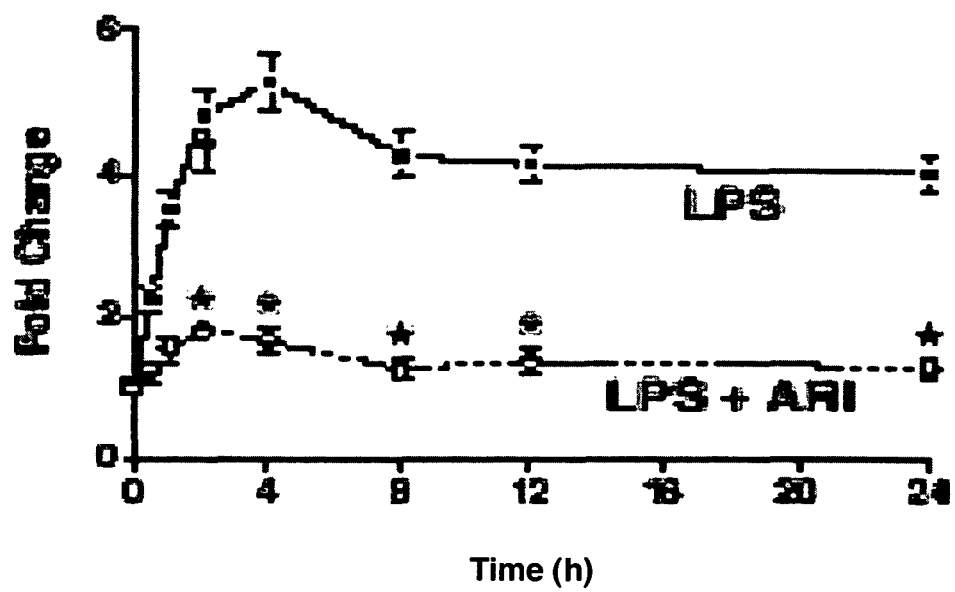
Figure 8C:
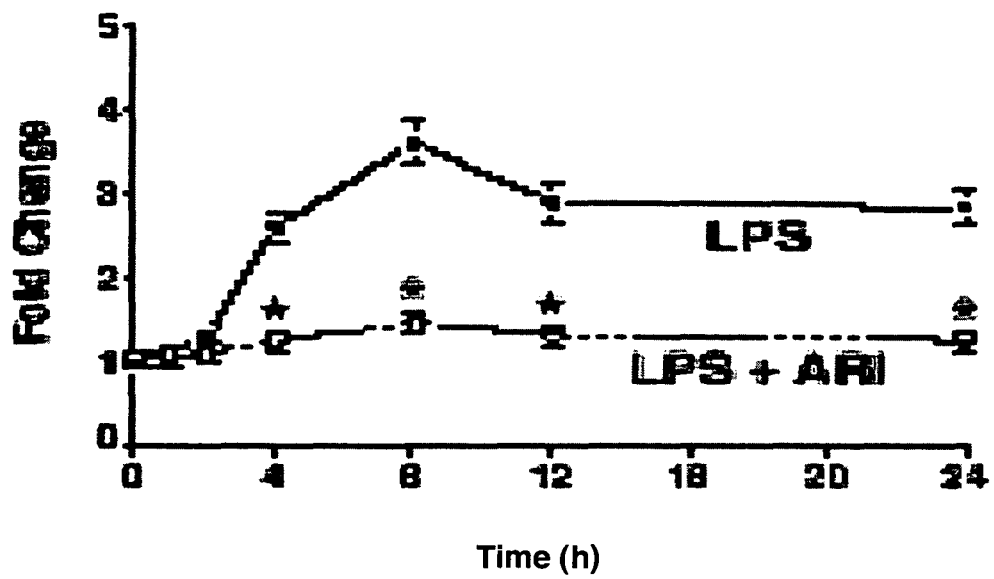
Figure 8D:
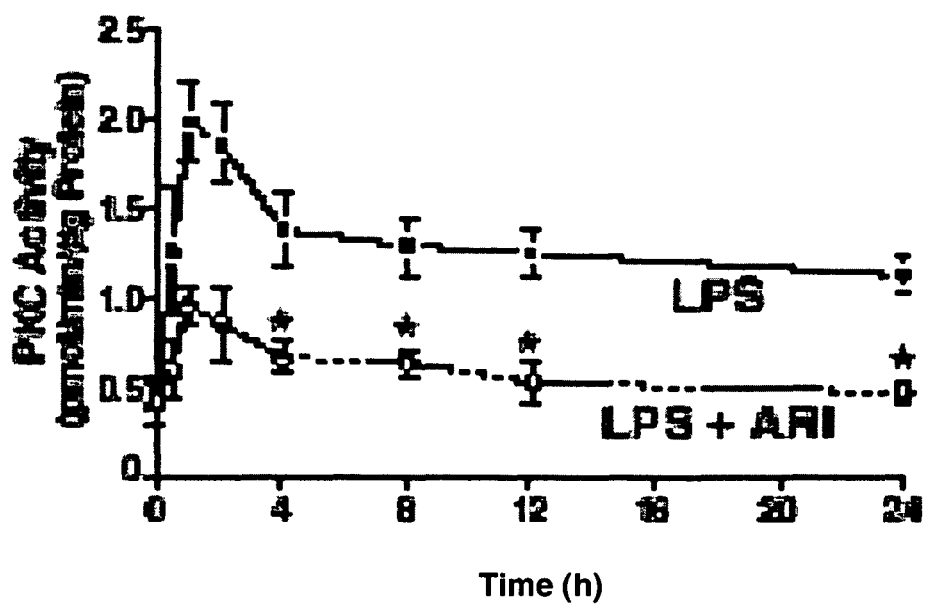

In untreated mice, LPS increased cardiac NF-κB activation by 16-fold and AP1 activation by 5-fold within 2 h, and the levels remained elevated even after 24 h (FIGS. 8A-8B). In sorbinil-treated mice, however, activation of NF-κB and AP1 decreased by ~70% at 2 h, and the levels returned to baseline by 24 h. Similar results were observed in mice treated with sorbinil before or 2 h after LPS exposure. These findings are consistent with the downregulation of inflammatory cytokines and chemokines in the serum and heart upon AR inhibition (FIGS. 8A-8D). Further, in response to LPS, cardiac iNOS levels increased by ~3-fold at 8 h and remained elevated at 24 h; however, in sorbinil-treated mice, iNOS levels increased only slightly and returned nearly to baseline levels by 24 h (FIG. 8C). As in macrophages, LPS significantly increased the phosphorylation of upstream kinases of NF-κB and AP1 (e.g., MAPK, IKK, PKC, and PLC) in the heart. AR inhibition attenuated the phosphorylation of almost all members of this cascade (FIG. 8D-8E). Thus, AR appears to inhibit the inflammatory cascade by regulating the activation of NF-κB, thereby protecting against cardiovascular collapse in the setting of overwhelming sepsis.

EXAMPLE 5

Figure 9A:
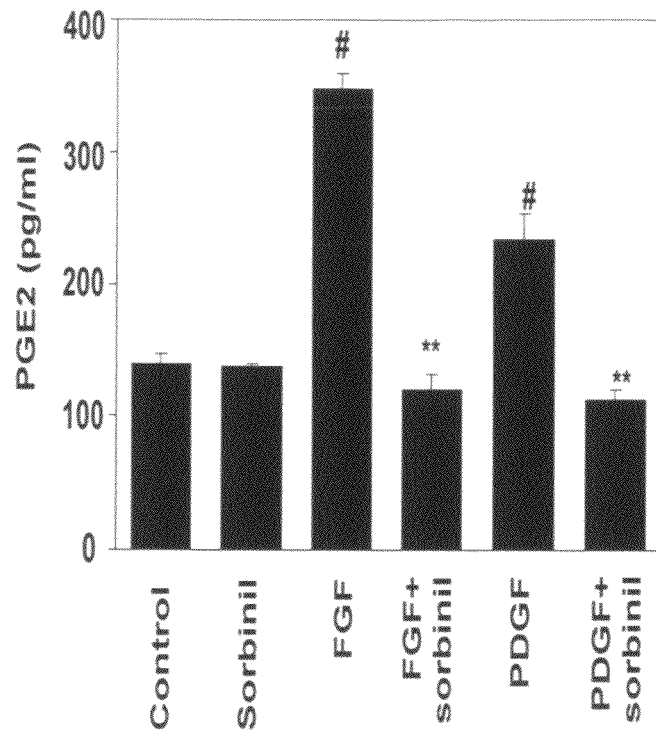
FIGS. 9A-9G illustrate that Inhibition or ablation of AR prevents growth factor-induced PGE2 production and Cox-2 expression in colon cancer cells. Growth-arrested Caco-2 cells were pre-incubated with sorbinil or carrier for 24 h (FIG. 9A) and with AR antisense or scrambled oligos (FIG. 9B). The inset in FIG. 9B represents Western blot analysis for AR protein in untransfected (c), scrambled (s) and AR antisense (a) oligo transfected cell extracts. The AR inhibited and ablated cells were stimulated with BFGF or PDGF as in FIG. 10A except that Cox activity was measured by a Cox activity assay kit (FIG. 9C). Western blots were developed using antibodies against Cox-2 (FIG. 9D), Cox-1 (FIG. 9E) and GAPDH (FIG. 9F).
Figure 9B:
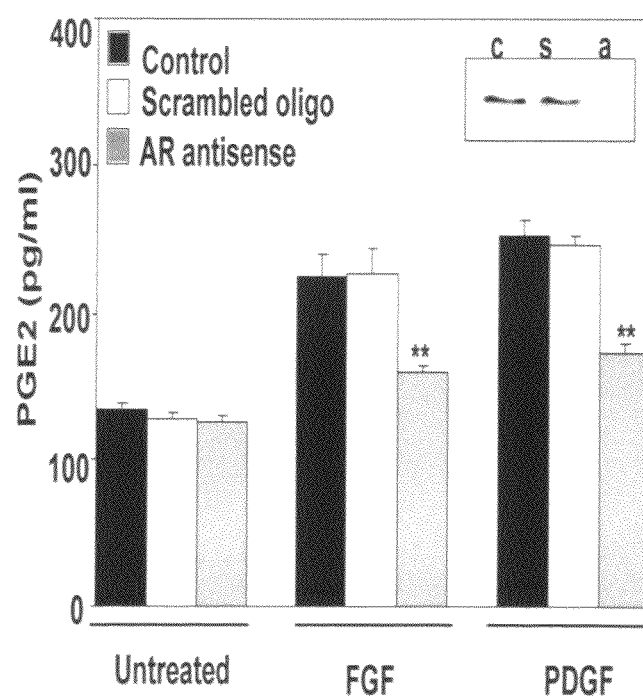

In Vitro Effects of Aldose Reductase Inhibition on Caco-2, Ht-29 and A549 Cell Lines
AR Inhibition Prevents PGE2 Production and Cox Activity Caco-2 Cells The growth factors are known to induce PGE2 production by activating inducible Cox-2 in colon cancer (58), but the mechanism is not well understood. Inhibition of AR significantly (>90%) prevented the production of PGE2 by Caco-2 cells induced by BFGF and PDGF (FIG. 9A). However, sorbinil alone did not inhibit constitutive levels of PGE2. Since the non-specificity of AR inhibitors could not be rigorously excluded, parallel studies were performed by transfecting Caco-2 cells with antisense AR oligonucleotides that decreased AR protein expression by >95% (FIG. 9B, inset) and also the enzyme activity by >90% (data not shown). In contrast to the cells transfected with scrambled oligonucleotides, cells transfected with antisense AR displayed markedly attenuated PGE2 production upon stimulation with BFGF or PDGF (FIG. 9B). PGE2 generation in Cox-2 negative cells (HCT-116) by growth factors was non-significant (data not shown).

Figure 9C:
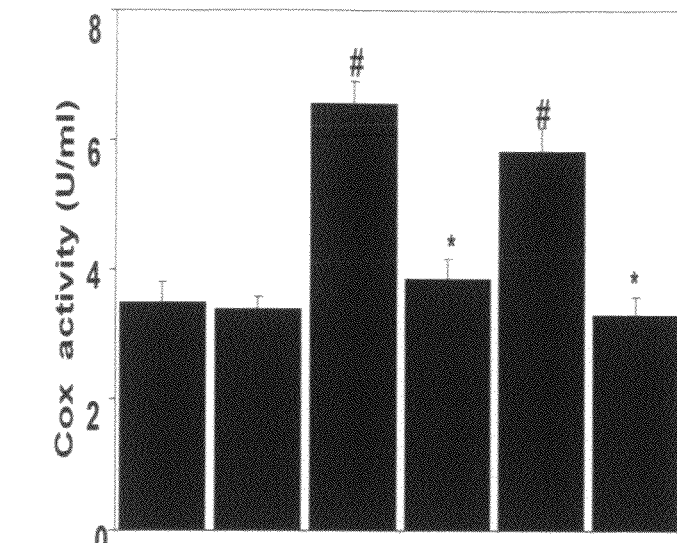
Figure 9D:
Figure 9E:
Figure 9F:
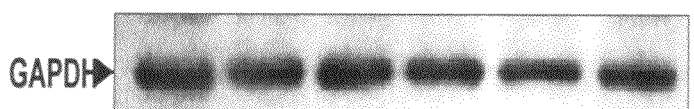
Figure 9G:
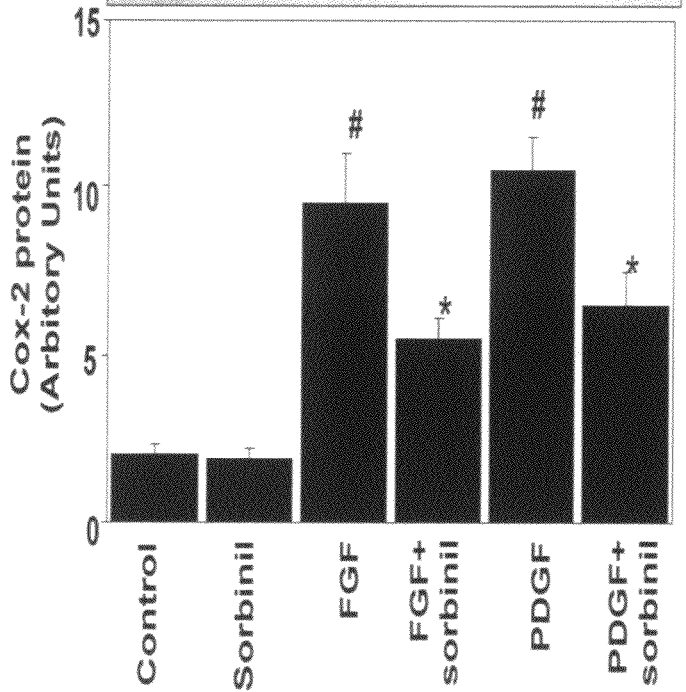

Since PGE2 is synthesized from its precursor arachidonic acid catalyzed by cyclooxygenases, whether or not inhibition of AR prevents growth factor-induced expression of Cox enzymes was examined. Treatment of Caco-2 cells with BFGF and PDGF significantly (60-80%) increased Cox activity (FIG. 9C). Pre-incubation with sorbinil abolished both BFGF and PDGF-induced Cox activity. Since Cox activity is contributed by two isozymes, constitutive Cox-1 and inducible Cox-2, the affect of AR inhibition on Cox-1 and Cox-2 isozymes was examined by Western blot analysis using specific antibodies. The levels of constitutive Cox-1 protein were not affected by growth factors or sorbinil (FIG. 9E), whereas Cox-2 protein significantly increased and was attenuated by sorbinil (FIGS. 9D,9G).

AR Inhibition Prevents HT-29 and A549 Cell Proliferation

The effect of AR inhibitors sorbinil and zopolresta on the role of AR in the signal transduction pathway of growth factors leading to HT29 cells proliferation is examined. The extent of HT29 cells proliferation was determined by MTT assay. FIG. 10A demonstrates that treatment of HT29 cells with EGF and BFGF for 24 h significantly (>40%) stimulated growth. The increase in HT29 cell growth was significantly attenuated (>60%) by AR inhibitors, sorbinil or zopolrestat. However, sorbinil or zopolrestat alone did not cause any effect on HT29 cells proliferation. It is contemplated that AR is an obligatory mediator of growth factors-induced colon cancer cell proliferation.

The extent of A549 cells proliferation was determined by MTT assay. FIG. 10B demonstrates that treatment of A549 cells with various concentrations of sorbinil and tolrestat resulted into concentration dependent inhibition of proliferation. The maximum 100 μM concentration of sorbinil or tolrestat caused more than 75% inhibition of A549 cells proliferation. It is contemplated that AR is an obligatory mediator in the lung cancer cells proliferation.

Figure 10C:
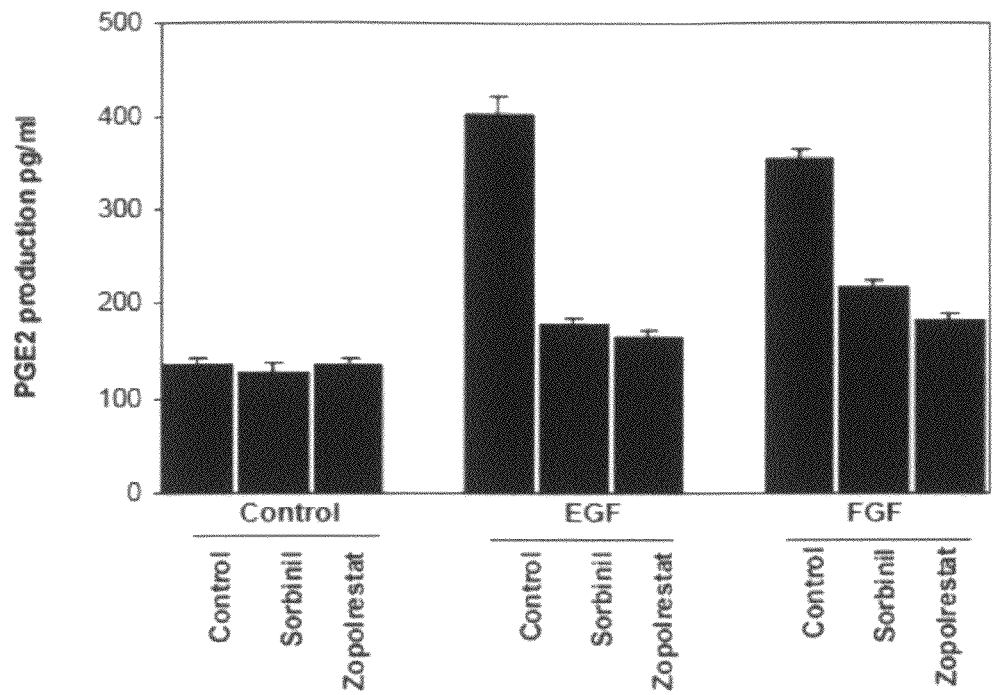

The role of AR in the induction PGE2 production by growth factors in HT29 cells also is examined. FIG. 10C shows that both EGF and BFGF significantly induced the production of PGE2 by HT29 cells and AR inhibitors significantly (>90%) prevented it. However, sorbinil or zopolrestat alone did not inhibit constitutive levels of PGE2. It is contemplated that AR inhibition prevents growth factors-induced PGE2 production in HT29 cells.

Figure 10D:
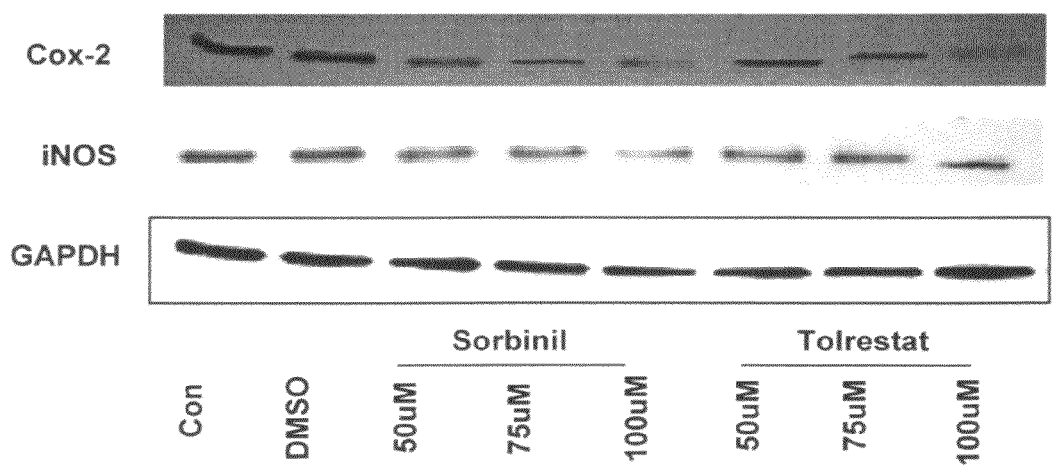

To determine the role of AR in inflammatory markers expression of Cox-2 and iNOS in A549 cells is measured. FIG. 10D shows that inhibition of AR significantly prevents the expression of Cox-2 and iNOS proteins in a concentration dependent manner. It is contemplated that AR inhibitors could be used as therapeutic drugs in inflammation related cancers such as lung cancer.

Inhibition of AR Prevents Growth Factor-Induced NF-κB Activation in Caco-2 Cells The effect of AR inhibitors on growth factor-induced NF-κB activation was examined, because it is known that redox sensitive transcription factor NF-κB transcribes Cox-2 DNA (59) and it has been demonstrated that AR inhibition prevents growth factors and cytokine-induced NF-κB activation (15). Treatment of caco-2 cells with BFGF or PDGF significantly (2-3 fold) increased the mRNA levels of Cox-2 and sorbinil prevented it by 55-65% (FIGS. 11A-11C) suggesting that AR could regulate the transcriptional activation of Cox-2 DNA. Both BFGF and PDGF significantly (~3 fold) induced NF-κB-dependent reporter (SEAP) activation in Caco-2 cells and sorbinil caused >60% inhibition (FIG. 11D). However, sorbinil alone did not affect the NF-κB-SEAP activity. Stimulation of Caco-2 cells with BFGF or PDGF resulted in a pronounced (~10 fold) activation of NF-kB DNA binding activity as determined by colorimetric, non-radioactive NF-κB p65 transcription assay method (FIG. 11E) and sorbinil caused >70% inhibition.

These results validate previous measurements of NF-κB activity and substantiate that the specific activity observed in SEAP and colorimetric methods is due to NF-κB activation. It is contemplated that inhibition of AR prevents growth factor-induced activation of NF-κB in Caco-2 cells, which transcriptionally may activate Cox-2 expression.

Inhibition of AR Prevents Growth Factors-Induced PKC Activation in Caco-2 Cells

Figure 12E:
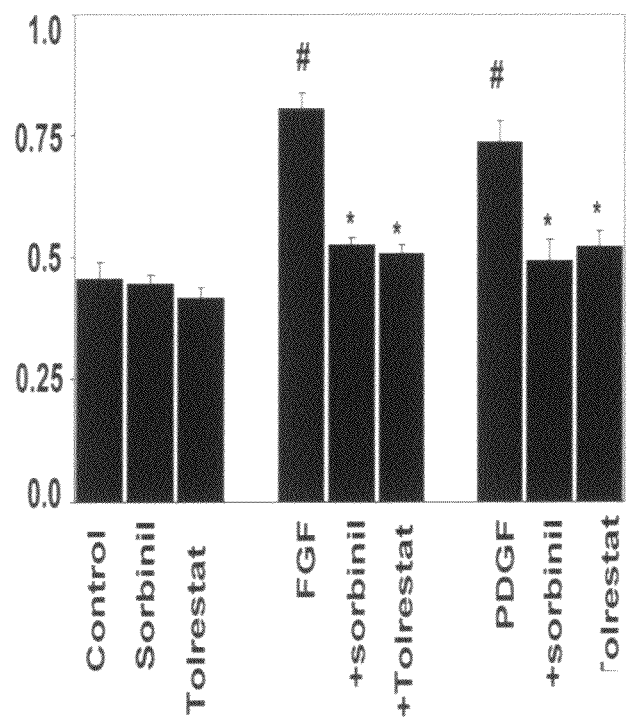

Since PKC is an upstream kinase for the activation of NF-κB and activation of PKC-b2 has been implicated in colon carcinogenesis (60), the effect of growth factors on total PKC activity in Caco-2 cells in the absence and presence of AR inhibitor was examined. Stimulation with growth factors led to a significant (~3 fold) increase in membrane-bound PKC activity (FIG. 12A) and sorbinil significantly prevented it. However, sorbinil by itself did not alter the total PKC activity in these cells. Both BFGF and PDGF activated PKC-β2 in Caco-2 cells (FIGS. 12B-12D). BFGF caused maximal PKC phosphorylation at 2 h whereas PDGF caused maximal phosphorylation at 1 h and increase in PKC-β2 phosphorylation was significantly (>70%) attenuated by sorbinil.

Attenuation of Growth Factors-induced Caco-2 Cell Line Proliferation

Figure 12F:
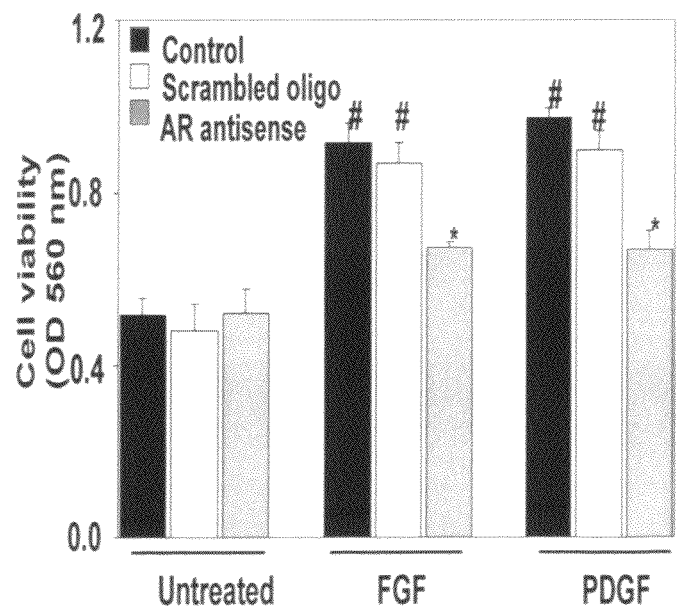

Since increased Cox-2 expression has been shown to facilitate colon cancer progression by stimulating cell proliferation and survival (61), the role of AR in growth factors-induced Caco-2 cell growth was examined. Treatment of Caco-2 cells with BFGF and PDGF for 24 h significantly (>40%) stimulated growth (FIG. 12E) which was significantly attenuated (>80%) by sorbinil or by antisense ablation of AR (FIG. 12F) indicating that AR is an obligatory mediator of growth factors-induced colon cancer cell proliferation.

Figure 13A:
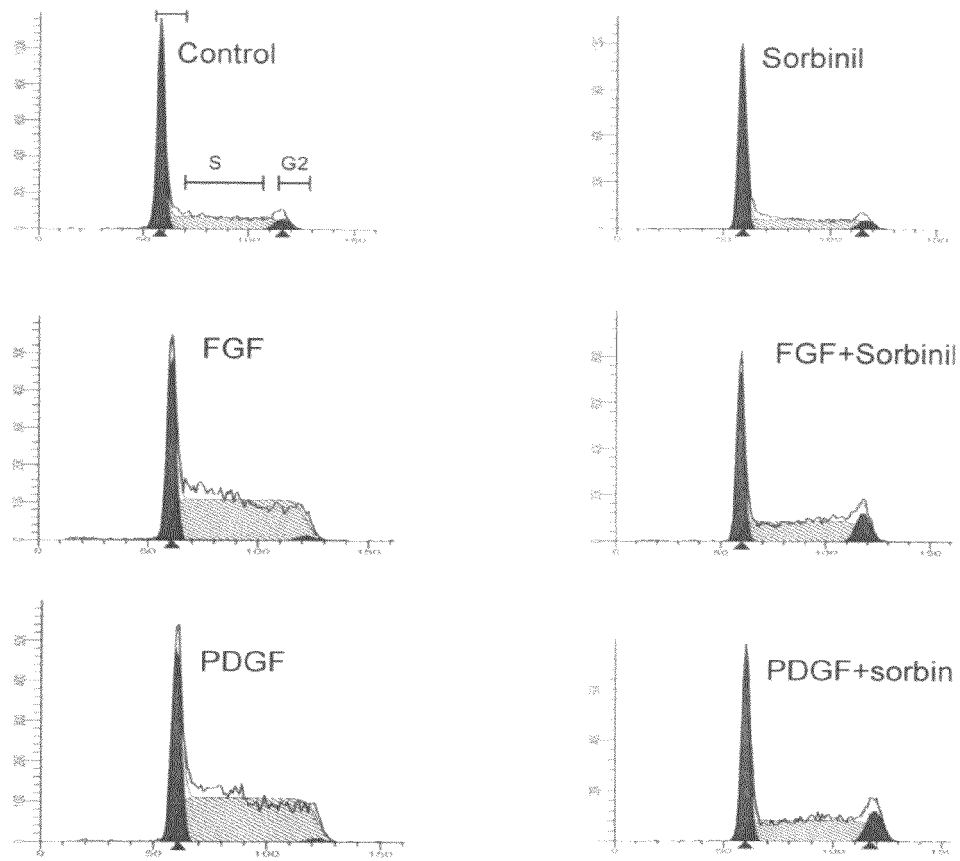
FIGS. 13A-13C illustrate the effects of sorbinil on the cell cycles of Caco-2 cells and A549 cells.

AR Inhibition Affects Cell Cycle and/or Cell Proliferation in Caco-2 and A549 Cells Treatment of Caco-2 cells with growth factors significantly induced synthetic (S)-phase of the cell cycle (FIG. 13A) suggesting that the cells were undergoing proliferation. Inhibition of AR prevented growth factor-induced accumulation of cells in S-phase and the cells accumulated at G2/M phase and G1 phase, suggesting that AR inhibition prevents synthetic phase of cell cycle which is an important stage required for cell growth. Table 3 shows the percentage of Caco-2 cells in the G1, G2 and S phases in the presence of sorbinil.

TABLE 3

| Cell Cycle Analysis | | | | | | |
|---|---|---|---|---|---|---|
| | G1 | | S | | G2 | |
| | EXP | SOR | EXP | SOR | EXP | SOR |
| Control | 52.61 | 54.97 | 41.66 | 39.71 | 5.73 | 5.32 |
| FGF | 26.87 | 36.31 | 71.66 | 52.15 | 1.47 | 1.54 |
| PDGF | 27.36 | 36.18 | 71.49 | 51.71 | 1.15 | 12.10 |

Treatment of A549 cells with 10% FBS in the medium significantly induced synthetic (S) phase of cell cycle (FIG. 13B), suggesting that the cells were undergoing proliferation. Inhibition of AR prevented accumulation of cells in S phase and the cells accumulated at G2-M phase and G1 phase, suggesting that AR inhibition prevents synthetic phase of cell cycle, which is an important stage required for cell growth. Table 4 shows the percentage of A549 cells in the G1, G2 and G2 phases in the presence of sorbinil.

TABLE 4

Cell Cycle Analysis

| Medium | G1 | G2 | S |
|---|---|---|---|
| 10% FBS | 56.54 | 4.53 | 38.93 |
| Sorbinil (25 µM) | 58.79 | 6.06 | 35.14 |
| Sorbinil (50 µM) | 59.24 | 5.47 | 35.29 |
| Sorbinil (75 µM) | 64.21 | 5.55 | 30.24 |
| Sorbinil (100 µM) | 65.55 | 4.8 | 29.75 |

Figure 13C:
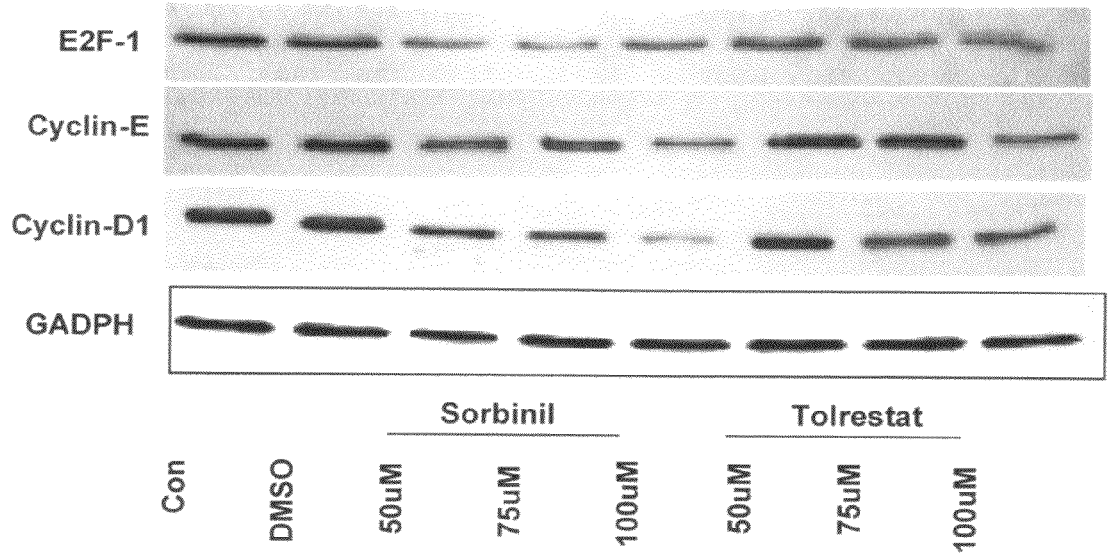
Figure 13B:
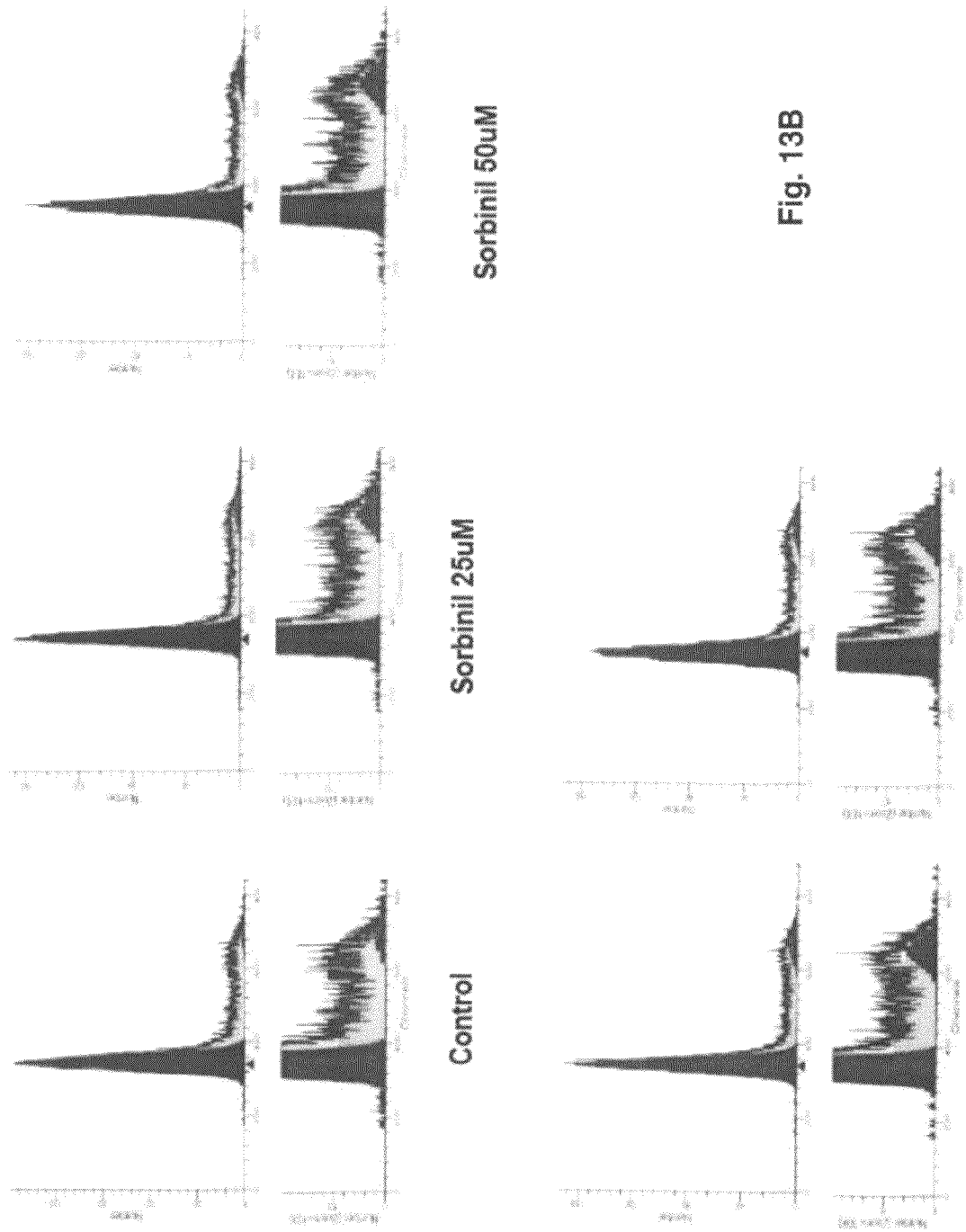

Treatment of A549 cells with various concentrations of sorbinil or tolrestat caused significant inhibition of important cell cycle regulatory proteins such as E2F-1, Cyclin E and Cyclin D1 expression (FIG. 13C). These results indicate that inhibition of AR prevents G1 to S phase transition.

Figure 14A:
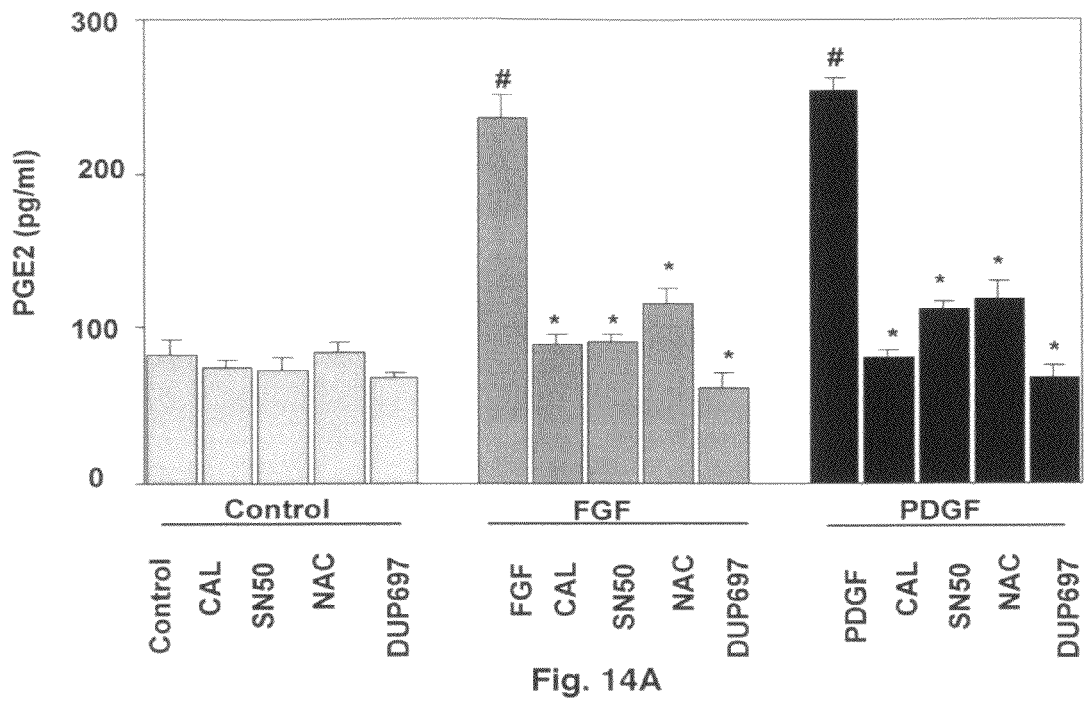
FIGS. 14A-14B illustrate the effect of PKC, NF-kB and Cox-2 inhibitors and AR inhibitors on growth factor-induced PGE2 and ROS production, respectively in colon cancer cells. Growth-arrested Caco-2 cells were pre-incubated with PKC, NF-kB and Cox-2 inhibitors or ROS scavenger for 30 min (FIG. 14A) or AR inhibitors for 24 h (FIG. 14B). The growth-arrested Caco-2 cells were incubated further with BFGF or PDGF for 24 h (FIG. 14A) and 1 h (FIG. 14B). Bars represent mean±S.E. (n=4); # $p<0.001$ Vs. control cells and * $p<0.01$ Vs. cells treated with growth factors.
Figure 14B:
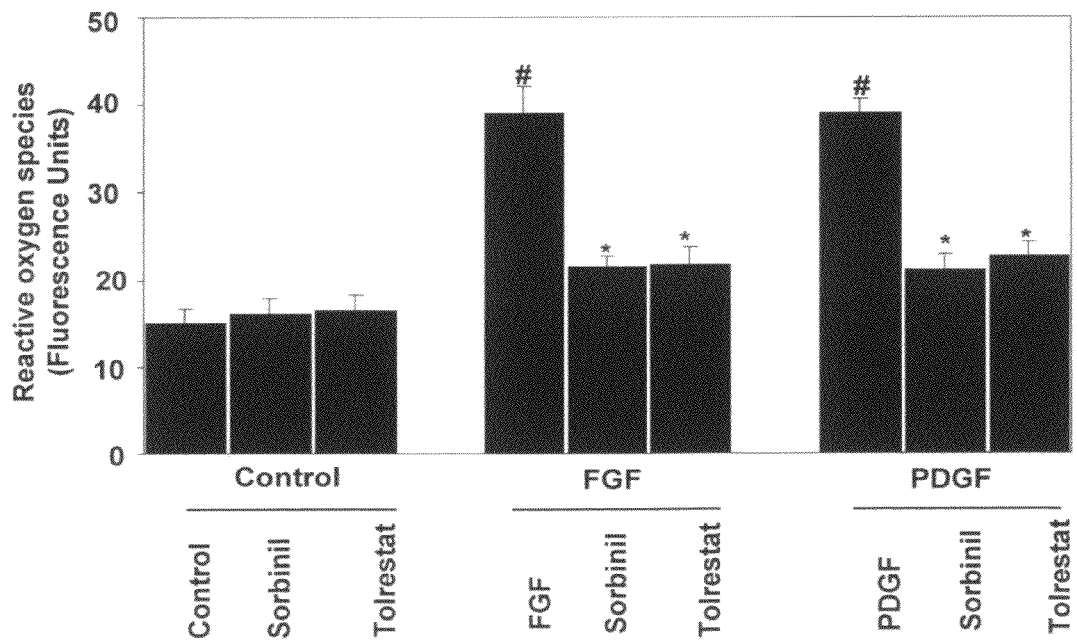

Attenuation of Growth Factors-induced Upregulation of PGE2 Production by Inhibitors of Signaling Cascade for NF-κb Activation In order to understand the role of NF-κB in the growth factor-induced upregulation of PGE2, inhibitors of PKC (Calphostin c), Cox-2 (DUP697), reactive oxygen species scavenger (N-acetyl cysteine), and NF-κB (SN50) were utilized. Growth factors caused a pronounced increase in the production of PGE2 and preincubation of Caco-2 cell with the above inhibitors attenuated, indicating that signaling events that lead to activation of NF-κB and its dependent Cox-2 expression are involved in the production of PGE2 (FIG. 14A). Further, growth factors caused pronounced increase in ROS which was inhibited by sorbinil and tolrestat (FIG. 14B).

Effect of AR Inhibition on Lipid Aldehyde-induced Signaling in Caco-2 Cells

It has been demonstrated that AR is an excellent catalyst for the reduction of lipid peroxidation-derived aldehydes, such as HNE and their conjugates with glutathione to corresponding alcohols (4, 20). Since, it is contemplated that AR inhibition or ablation prevents growth factor-induced expression of Cox-2 and production of PGE2, AR-catalyzed reduction of lipid aldehydes involvement in this mechanism was determined. Treatment of cells with HNE or cell permeable esters of GS-HNE or GS-DHN resulted in increased PGE2 production (FIG. 15A) and also Cox-2 expression (FIGS. 15B-15D). Inhibition of AR by sorbinil significantly prevented the HNE and GS-HNE-induced Cox-2 expression and PGE2 production but had no effect on GS-DHN-induced expression of these inflammatory markers. These results indicate that growth factors-induced mitogenic signaling in colon cancer cells could be mediated by the reduced form of lipid aldehyde-glutathione conjugates catalyzed by AR.

Inhibition of AR Prevents Invasion of HT29 and A549 Cells

Figure 16A:
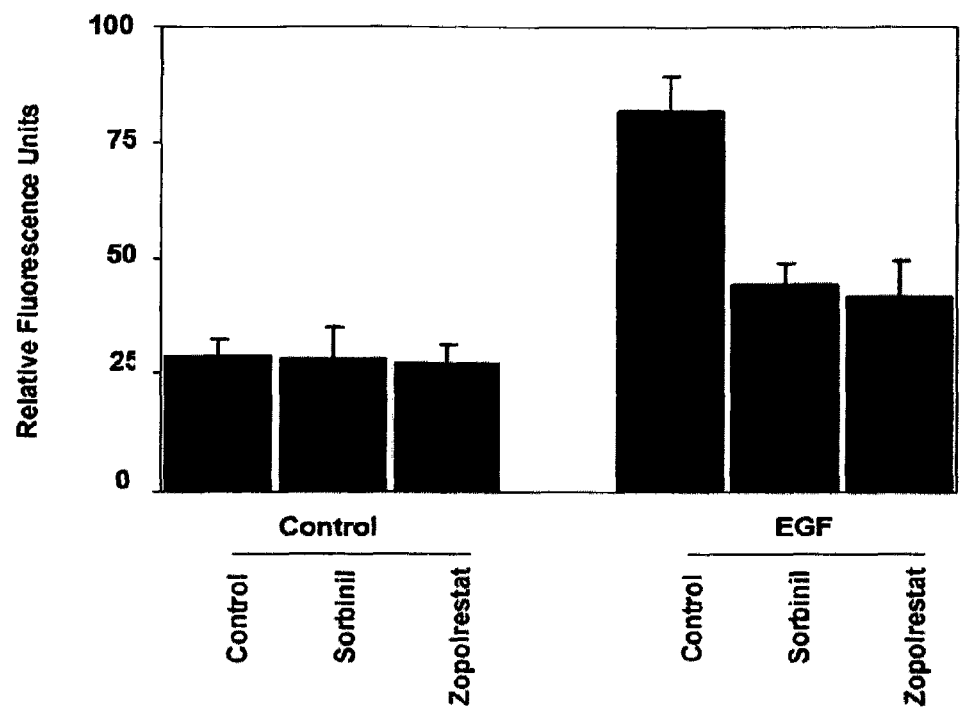
FIGS. 16A-16B illustrate that sorbinil and zopolrestat separately inhibit penetration of an extracellular matrix material by HT29 cells (FIG. 16A) and by A549 cells (FIG. 16B).
Figure 16B:
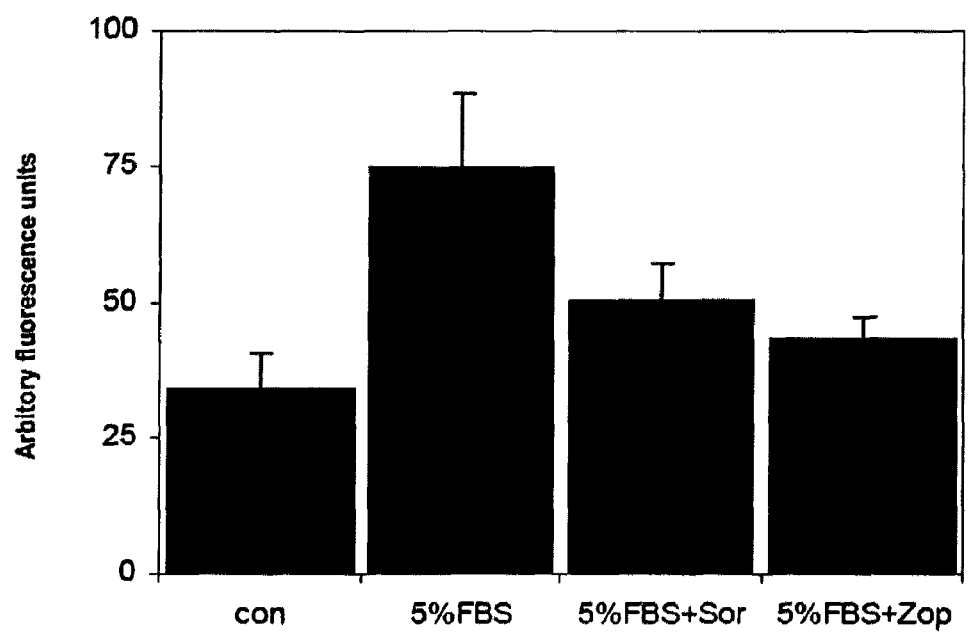

The ability of HT29 cells and A549 cells to penetrate extracellular matrix material (Matrigel) in vitro was assessed by inhibiting AR in presence of sorbinil or zopolrestat (75 µM, HT29 or 100 µM, A549). FIG. 16A shows that stimulation of HT29 cells with EGF (5 ng/ml) for 24 hrs caused significant invasion through matrigel. Inhibition of AR prevented invasion of HT29 cells by more than 70%. FIG. 16B shows that treatment of A549 cells with 5% FBS for 24 hrs caused significant invasion through matrigel. Inhibition of AR prevented invasion of A549 cells by more than 60%.

EXAMPLE 6

In Vivo Effects of Aldose Reductase and its Inhibition in Mouse Models of SW480, HT29 and A549 Cancers Effect of Aldose Reductase siRNA on SW480 Xenografts Athymic nude nu/nu mice were obtained from Harlan, Indianapolis, Ind. Nine 20-weeks-old athymic nu/nu nude mice were divided into three groups of 3 animals (Group 1: treated with PBS; Group 2: treated with scrambled siRNA and Group 3: treated with aldose-reductase siRNA). An aliquot of $2 \times 10^6$ SW480 human colon adenocarcinoma cell suspensions in 100 µl PBS was injected subcutaneously into one flank of each nu/nu nude mouse. Animals were examined daily for signs of tumor growth. Treatment was administered when the tumor surface area exceeded 45 mm$^2$, i.e., day 25. Treatment consisted of 200 mg aldose-reductase siRNA in 100 ml PBS administered intraperitoneally. Control groups were treated with 200 mg/100 ml scrambled siRNA, or diluent (PBS) alone. Mice were treated on days 1 and 14. Tumors were measured in two dimensions using calipers over 40 days.

Figure 17A:
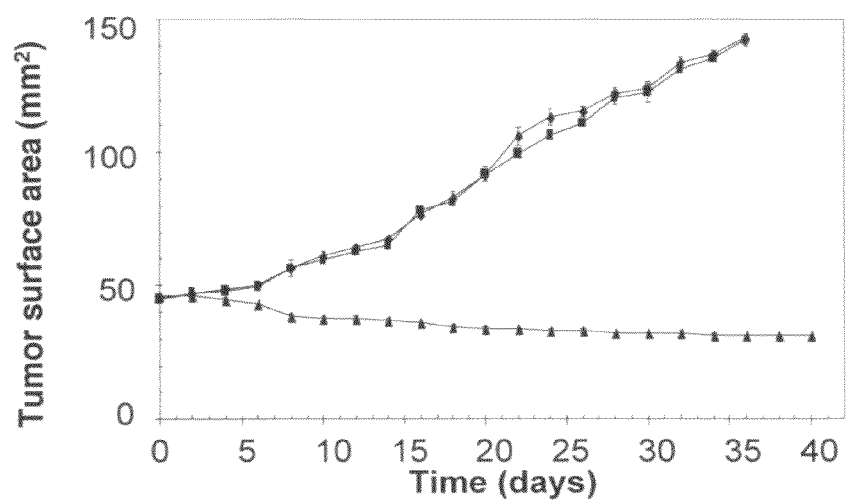
FIGS. 17A-17B illustrate the effect of AR siRNA on tumor size of SW480 xenografts (FIG. 17A) and on body weight (FIG. 17B). At different days tumors were measured in two dimensions using calipers.
Figure 17B:
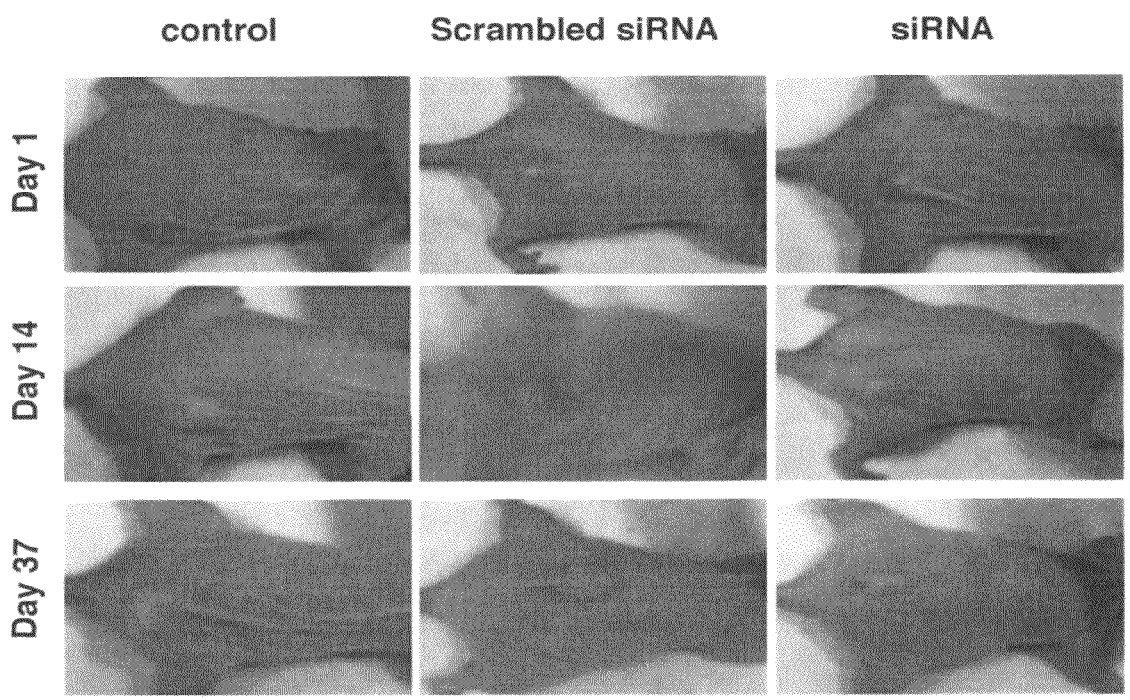

Results presented in FIG. 17A clearly demonstrate that the tumor progression was completely arrested in the animals treated with AR-siRNA, whereas uncontrolled growth was observed in the control as well as in scrambled siRNA treated mice. None of the treatments interfered with the normal weight gain of animals during the experiments. FIG. 17B are photographs of animals taken at 1, 14 and 37 days. These findings indicate that AR inhibition completely halts the colon cancer progression without interfering with the normal weight gain of the animals after its administration.

Role of AR in the Prevention of Colon Cancer in AOM-treated Wild Type and AR Knock Out Mice Azoxymethane-induced colon carcinogenesis was studied in a mouse model. Similar to humans, azoxymethane-induced aberrant crypt foci (ACF) formation in rodent models is the earliest identifiable preneoplastic lesions in the progression of normal colonic epithelium. In addition, azoxymethane reproducibly induces aberrant crypt foci and colon tumors formation in rodents with many of the same genetic and signal transduction defects identified in human colon carcinomas.

Figure 18A:
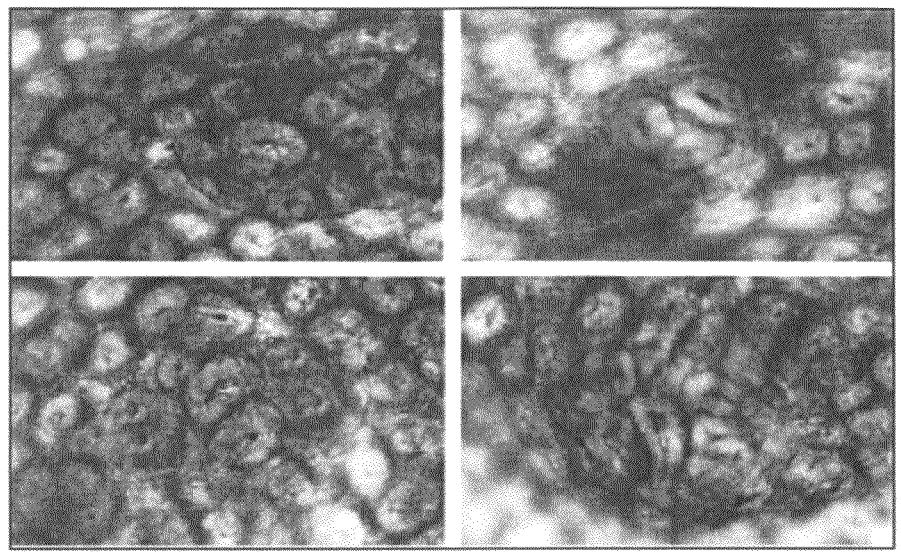
FIGS. 18A-18D illustrate the effects of sorbinil on the number of aberrant crypt foci (ACF) in azoxymethane (AOM) treated wild type and knock out mice.

BALB/C mice were injected with azoxymethane or saline and treated with and with out AR inhibitor, sorbinil as described in Example 2. At the early preneoplastic stage (9 weeks after first azoxymethane injection), mice were sacrificed and their colons were removed and analyzed microscopically for the presence of ACF. ACF were distinguished from the surrounding normal crypts by increased thickening of the crypt walls and aberrant change in the shape of the crypt lumen (FIG. 18A). The parameters used to assess the aberrant crypt foci were their occurrence/colon and number of aberrant crypts foci. All the colons were scored by three blind observers azoxymethane did not know the identity of the samples.

Figure 18B:
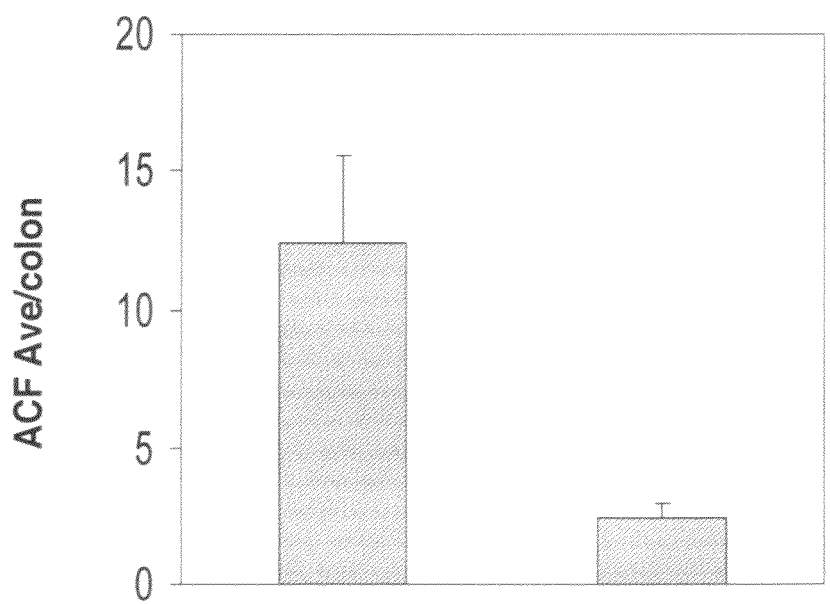
Figure 18C:
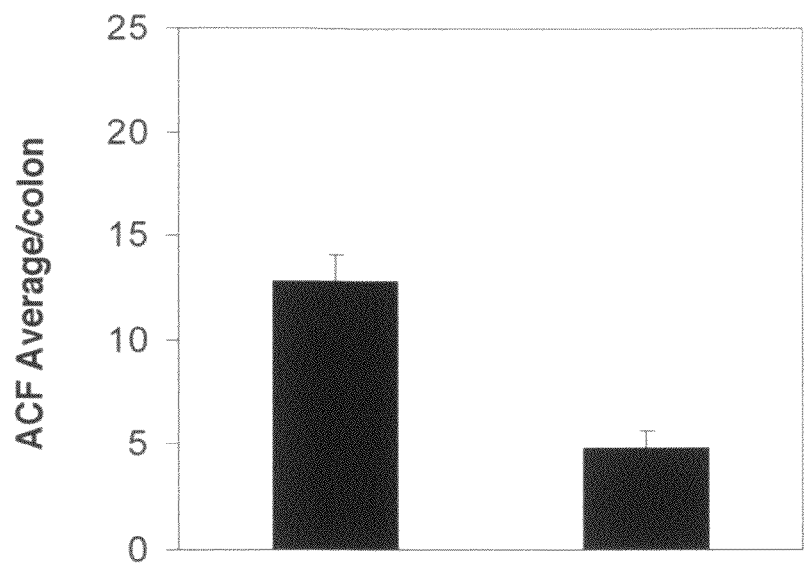

FIG. 18B shows that in azoxymethane group the number of average ACF/colon were 12.4±3.2, whereas in azoxymethane+sorbinil treated mice the formation of aberrant crypt foci was significantly less (2.4±0.5), suggesting that inhibition of AR prevents azoxymethane-induced aberrant crypt foci formation. No aberrant crypt foci were observed in saline treated control animals. To rule out the non specificity of pharmacological AR inhibitor, sorbinil genetically AR gene knocked out (KO) mice were used for azoxymethane-induced aberrant crypt foci formation. FIG. 18C shows that AR KO mice had low number of aberrant crypt foci (5.2±0.8) as compared wild type mice (12±1.4). These results support the inhibition of AR preventing azoxymethane-induced aberrant crypt foci formation in wild type mice as well as AR KO mice.

Figure 18D:
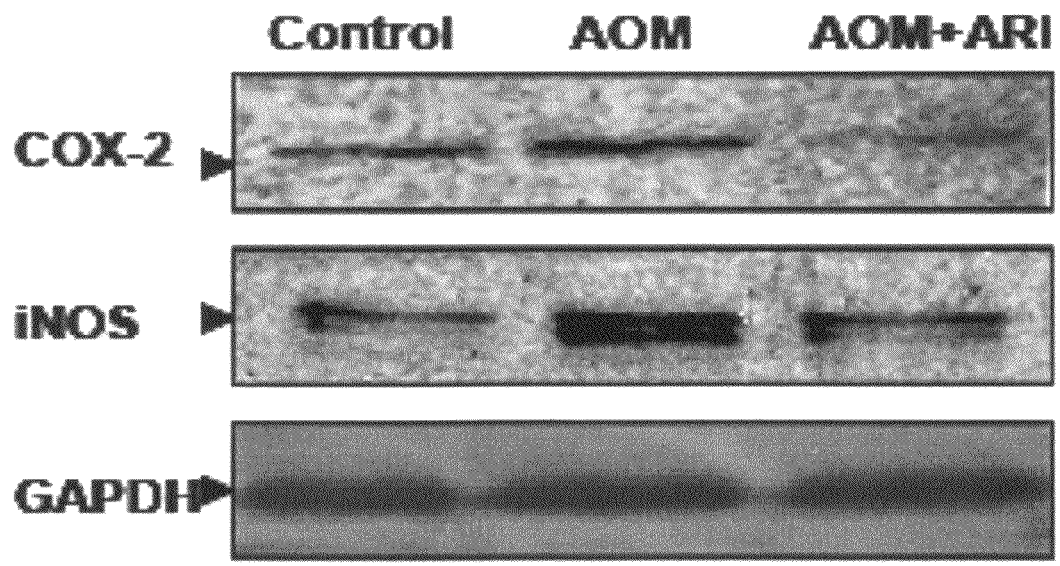

To determine the role of AR in AOM-induced inflammatory markers expression the expression of Cox-2 and iNOS in mice colons after 9 weeks of AOM induction were measured. FIG. 18D shows that inhibition of AR significantly prevents AOM-induced inflammatory markers such as Cox-2 and iNOS. It is contemplated that AR inhibitors could be excellent chemopreventive drugs to treat colon cancer.

Inhibition of AR Prevents Metastatic Tumor Growth in a Mouse Model

Liver is the common site for systemic metastasis during advanced stage of colorectal cancer. The effect of AR inhibition in tumor cell migration was examined using a mouse liver metastasis model. HT29 cells ($5 \times 10^6$), which are transfected with a plasmid containing GFP, were injected intrasplenically into the athymic mice. Animals were randomized into 2 experimental groups (5 animals per group) to receive control and sorbinil (40 mg/kg/body weight) diet. Metastasis to the liver was followed up periodically using Illumatool TLS. Detectable levels of liver metastasis were observed 4 weeks after splenic injection of HT29 cells.

After 34 days mice were killed and development of liver metastasis was monitored by a qualitative assessment of GFP fluorescence using bioluminescent imaging. Mice fed with control diet increased metastases significantly compared to diet containing AR inhibitor, sorbinil (FIG. 19A). The results were further quantified by measurement of fluorescence and values expressed as pixel numbers (FIG. 19B). Results demonstrate a significant decrease in tumor metastasis in the sorbinil fed animals compared with control diet which correlates with the qualitative assessment. It is contemplated that inhibition of AR represents a unique strategy for the suppression of colorectal cancer metastasis.

AR Inhibition Prevents Progression of Lung Cancer Tumor Growth

The results obtained from in vitro studies were confirmed by in vivo nude mice model bearing human lung carcinoma A549 cells. A549 ($2 \times 10^6$) cells were implanted s.c. and allowed to grow in nu/nu nude mice to ~45 mm$^2$ over a period of 25 days. Animals were grouped into control and experimental groups. Control group were fed with regular diet and experimental group was fed with AR inhibitor, Zopolrestat (after 10 days dose increased from 20 mg to 40 mg/kg/body weight) for until end of the experiment. Tumor growth was measured every two days using calipers. The photographs of animals were taken at days 1, 14, and 37 (FIGS. 20A-20B).

FIG. 20B clearly shows that the tumor progression was completely arrested in the animals fed with AR inhibitor, zopolrestat, whereas uncontrolled growth was observed in the control animals. None of the treatments interfered with the normal weight gain of animals during the experiments.

Inhibition of AR by siRNA Prevents Tumor Growth and ROS Production

Although the pharmacological AR inhibitor zopolrestat selectively inhibits AR, the nonspecificity of this drug could not be rigorously excluded. Therefore, the role AR in lung cancer tumor progression was confirmed by ablating AR with SiRNA. FIG. 21A shows that mice which received i.p, injection of 200 µg AR-siRNA in 100 µl PBS on days 1 and 14 the progression of tumor growth was inhibited completely compared to animals which received an injection PBS, scrambled siRNA.

To confirm that AR inhibition prevents AR protein expression in the xenografts, serial sections of the xenograft were taken and fixed in para-formaldehyde as in Example 4. Cross sections of control, scrambled and SiRNA injected nude mice tumors were stained with antibodies against peptide specific AR. FIG. 21B demonstrate animals treated with ARSiRNA showed significantly prevention of AR protein expression compared to control and scrambled siRNA as evidenced by dark brown color. These results indicate that inhibition of AR prevents tumors progression in lung cancer xenografts.

Since progression of tumorigenesis is usually induced by reactive oxygen species (ROS) generation, whether inhibition of AR prevents ROS production was measured in nude mice xenograft sections. The tumor sections were prepared and red fluorescence in the presence of HEt dye was measured as described in Example 4. FIG. 21C shows sections of animals treated with AR siRNA showed significantly reduced red fluorescence compared to control and scrambled siRNA indicating that inhibition of AR prevented the ROS production there by inhibiting the progression of tumor growth.

The following references were cited herein:
1. Jez et al. (1997) *Biochem. J.* 326: 625-636.
2. Rondeau et al. (1992) *Nature* 355:469-72.
3. Wilson et al. (1992) *Science* 257:81-84.
4. Bhatnagar et al. (1992) *Biochem. Med. Metab. Biol.* 48:91-121.
5. Nishikawa et al. (2000) *Kidney Int. Suppl.* 77:S26-30.
6. Parry, G. J. (1999) *Am J Med* 107:27 S-33S.
7. Srivastava et al. (1995) *Biochem. Biophys. Res. Commun.* 217:741-746.
8. Srivastava et al. (1998) *Biochem. J.* 329:469-475.
9. Srivastava et al. (1999) *Biochemistry* 38:42-54.
10. van der Jagt et al. (1992) *J. Biol. Chem.* 267:4364-4369.
11. Kawamura et al. (1999) *Biochem Pharmacol* 58:517-24.
12. Rittner et al. (1999) *J Clin Invest* 103:1007-13.
13. Shinmura et al. (2002) *Circ Res* 91:240-6.
14. Ruef et al. (2000) *Arterioscler Thromb Vasc Biol* 20:1745-52.
15. Ramana et al. (2002) *J Biol Chem* 277(35):32063-70.
16. Uchida, K. (2003) *Prog Lipid Res* 42:318-43.
17. Grimshaw, C. E. (1992) *Biochemistry* 31:10139-45.
18. Varnai et al. (1999) *Proteins* 37:218-27.
19. Dixit et al. (2000) *J. Biol. Chem.* 275:21587-21595.
20. Ramana et al. (2000) *Biochemistry* 39:12172-12180.
21. Ramana et al. (2004) *FASEB J* 18:1209-18.
22. Ramana et al. (2004) *Diabetes* 53:2910-2920.
23. Petrash et al. (1992) *J. Biol. Chem.* 267:24833-24840.
24. Matthews, B. W. (1962) *J. Mol. Biol.* 33:491-7.
25. Otwinowski, Z. & Minor, W. (1997) *Meth. Enz.* 276:307-326.
26. Kissinger et al. (2001) *Acta Crystallogr D Biol Crystallogr* 57:1474-9.
27. Brunger et al. (1998) *Acta Crystallogr D Biol Crystallogr* 54(Pt 5):905-21.
28. Scott, et al. (2004) *J Biol Chem* 279:27294-301.
29. Tickle et al. (1998) *Acta Crystallogr D Biol Crystallogr* 5 (Pt 2):243-52.
30. Tickle et al. (1998) *Acta Crystallogr D Biol Crystallogr* 54(Pt 4):547-57.
31. Tickle et al. (2000) *Acta Crystallogr D Biol Crystallogr* 56(Pt 4):442-50.
32. Brunger A. T. (1992) *Nature* 355:472-474.
33. McRee D. E. (1999) *J Struct Biol* 125:156-65.
34. Matthews et al. (1975) *Acta Crystallogr A* 31:480-487.

35. Hynes T. R. & Fox, R. O. (1991) *Proteins* 10:92-105.
36. van Aalten et al. (1996) *Journal of Computer Aided Molecular Design* 10:255-262.
37. Laskowski et al. (1996) *J Biomol NMR.* 8:477-86.
38. Murshudov et al. (1999) *Acta Crystallogr D Biol Crystallogr* 55(Pt 1):247-255.
39. (1994) *Acta Cryst. D* 50:760-763.
40. Delano W. L. (2003) (Delano Scientific, San Carlos, Calif.).
41. Calderone et al. (2000) *Acta Crystallogr D Biol Crystallogr* 56(Pt 5):536-40.
42. Urzhumtsev et al. (1997) *Structure* 5:601-12.
43. El-Kabbani et al. (1998) *Mol V is* 4:19.
44. Bohren et al. (1992) *J Biol Chem* 267:20965-70.
45. Prade et al. (1997) *Structure* 5:1287-.
46. Sussman et al. (1998) *Acta Crystallogr D Biol Crystallogr* 54:1078-84.
47. Yang et al. (1998) *Biochemistry* 37:17145-56.
48. Bousset et al. (2001) *Biochemistry* 40: 13564-.
49. Harrop et al. (2001) *J. Biol. Chem.* 276:44993-5000.
50. Becker et al. (1998) *Nat Struct Biol* 5:267-71.
51. Epp et al. (1983) *Eur J Biochem* 133:51-69.
52. Karplus et al. (1989) *Eur J Biochem* 178:693-703.
53. Kanaoka et al. (1997) *Cell* 90:1085-95.
54. Wilson et al. (1993) *PNAS* 90:9847-51.
55. Ramana et al. (2004) *FEBS Lett.,* 570(1-3):189-194.
56. Ramana et al. (2003) *FASEB J.* 17(2):315-317.
57. Smith et al. (2000) *Eur. J. Cancer,* 36(5):664-674.
58. Liu et al. (2003) *Cancer Res.* 63(13):3632-3636.
59. Chen et al. (2005) *J Biol. Chem.,* 280(16): 16354-16359.
60. Gokmen-Polar et al. (2001) *Cancer Res.,* 61(4):1375-1381.
61. Tsujii et al. (1998) *Cell,* 93(5):705-716.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A method of treating lung cancer comprising administering a pharmacologically effective amount of an inhibitor of aldose reductase to a subject having lung cancer, wherein the aldose reductase inhibitor is fidarestat.

* * * * *

SEQUENCE LISTING

```
<160> NUMBER OF SEQ ID NOS: 7

<210> SEQ ID NO 1
<211> LENGTH: 21
<212> TYPE: DNA
<213> ORGANISM: artificial sequence
<220> FEATURE:
<223> OTHER INFORMATION: aldose reductase siRNA

<400> SEQUENCE: 1
aatcggtgtc tccaacttca a                                             21

<210> SEQ ID NO 2
<211> LENGTH: 21
<212> TYPE: DNA
<213> ORGANISM: artificial sequence
<220> FEATURE:
<223> OTHER INFORMATION: scrambled sequence of siRNA control

<400> SEQUENCE: 2
aaaatctccc taaatcatac a                                             21

<210> SEQ ID NO 3
<211> LENGTH: 10
<212> TYPE: DNA
<213> ORGANISM: artificial sequence
<220> FEATURE:
<223> OTHER INFORMATION: NF-kappaB binding consensus sequence

<400> SEQUENCE: 3
gggactttcc                                                          10

<210> SEQ ID NO 4
<211> LENGTH: 19
<212> TYPE: DNA
<213> ORGANISM: artificial sequence
<220> FEATURE:
<223> OTHER INFORMATION: Cox-2 sense primer
```

-continued

```
<400> SEQUENCE: 4
aaacccactc caaacacag                                          19

<210> SEQ ID NO 5
<211> LENGTH: 20
<212> TYPE: DNA
<213> ORGANISM: artificial sequence
<220> FEATURE:
<223> OTHER INFORMATION: Cox-2 antisense primer

<400> SEQUENCE: 5
tcatcaggca caggaggaag                                         20

<210> SEQ ID NO 6
<211> LENGTH: 20
<212> TYPE: DNA
<213> ORGANISM: artificial sequence
<220> FEATURE:
<223> OTHER INFORMATION: beta-actin sense primer

<400> SEQUENCE: 6
tgagaccttc aacaccccag                                         20

<210> SEQ ID NO 7
<211> LENGTH: 24
<212> TYPE: DNA
<213> ORGANISM: artificial sequence
<220> FEATURE:
<223> OTHER INFORMATION: beta-actin antisense primer

<400> SEQUENCE: 7
ttcatgaggt agtctgtcag gtcc                                    24
```